(12) United States Patent (10) Patent No.: US 10,781,489 B2
Samavati et al. (45) Date of Patent: Sep. 22, 2020

(54) SYSTEMS AND METHODS TO DIAGNOSE SARCOIDOSIS AND IDENTIFY MARKERS OF THE CONDITION

(71) Applicants: WAYNE STATE UNIVERSITY, Detroit, MI (US); HENRY FORD HEALTH SYSTEM, Detroit, MI (US)

(72) Inventors: Lobelia Samavati, Beverly Hills, MI (US); Harvinder S. Talwar, Ypsilanti, MI (US); Rita Rosati, Troy, MI (US); Felix Fernandez-Madrid, Royal Oak, MI (US); Jia Li, Northville, MI (US)

(73) Assignees: WAYNE STATE UNIVERSITY, Detroit, MI (US); HENRY FORD HEALTH SYSTEM, Detroit, MI (US)

( * ) Notice: Subject to any disclaimer, the term of this patent is extended or adjusted under 35 U.S.C. 154(b) by 11 days.

(21) Appl. No.: 15/555,419

(22) PCT Filed: Mar. 4, 2016

(86) PCT No.: PCT/US2016/021035
§ 371 (c)(1),
(2) Date: Sep. 1, 2017

(87) PCT Pub. No.: WO2016/141347
PCT Pub. Date: Sep. 9, 2016

(65) Prior Publication Data
US 2019/0055602 A1 Feb. 21, 2019

Related U.S. Application Data

(60) Provisional application No. 62/128,436, filed on Mar. 4, 2015.

(51) Int. Cl.
*G01N 33/53* (2006.01)
*C12Q 1/6883* (2018.01)
*G01N 33/569* (2006.01)
*G01N 33/68* (2006.01)
*C12Q 1/68* (2018.01)

(52) U.S. Cl.
CPC ....... *C12Q 1/6883* (2013.01); *G01N 33/5695* (2013.01); *G01N 33/6893* (2013.01); *C12Q 2600/158* (2013.01); *G01N 2800/7095* (2013.01)

(58) Field of Classification Search
None
See application file for complete search history.

(56) References Cited

U.S. PATENT DOCUMENTS

| | | |
|---|---|---|
| 2004/0224408 A1 | 11/2004 | Girard et al. |
| 2005/0032062 A1 | 2/2005 | Chibout et al. |
| 2007/0099239 A1 | 5/2007 | Tabibiazar et al. |

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Barnett, et al., "Treatment of sarcoidosis-associated pulmonary hypertension. A two-center experience," Chest, vol. 135, No. 6, 2009, pp. 1455-1461.
Berry, et al., "An interferon-inducible neutrophil-driven blood transcriptional signature in human tuberculosis," Nature, vol. 466, No. 7309, 2010, pp. 973-977.
Bons, et al., "Potential biomarkers for diagnosis of sarcoidosis using proteomics in serum," Respir. Med., vol. 101, No. 8, 2007, pp. 1687-1695.
Chen, et al., "Expression profiling in granulomatous lung disease," Proc. Am. Thorac. Soc., vol. 4, No. 1, 2007, pp. 101-107.
Dragonieri, et al., "An electronic nose discriminates exhaled breath of patients with untreated pulmonary sarcoidosis from controls," Respir. Med., vol. 107, No. 7, 2013, pp. 1073-1078.
Dubaniewicz A., "Mycobacterium tuberculosis heat shock proteins and autoimmunity in sarcoidosis," Autoimmun. Rev., vol. 9, No. 6, 2010, pp. 419-424.
Eishi, et al., "Quantitative analysis of mycobacterial and propionibacterial DNA in lymph nodes of Japanese and European patients with sarcoidosis," J. Clin. Microbiol., vol. 40, No. 1, 2002, pp. 198-204.
Hajizadeh, et al., "*Mycobacterium tuberculosis* Antigen 85A induces Th-1 immune responses in systemic sarcoidosis," J. Clin. Immunol., vol. 27, No. 4, 2007, pp. 445-454.
Hunninghake, et al., "ATS/ERD/WASOG statement on sarcoidosis. American Thoracic Society/European Respiratory Society/World Association of Sarcoidosis and other Granulomatous Disorders," Sarcoidosis Vasc. Diffuse Lung Dis., vol. 16, No. 2, 1999, pp. 149-173.
Koth, et al., "Sarcoidosis blood transcriptome reflects lung inflammation and overlaps with tuberculosis," Am. J. Respir. Crit. Care Med., vol. 184, No. 10, 2011, pp. 1153-1163.
Lin, et al., "Autoantibody approach for serum-based detection of head and neck cancer," Cancer Epidemiol. Biomarkers Prev., vol. 16, No. 11, 2007, pp. 2396-2405.
Maertzdorf, et al., "Common patterns and disease-related signatures in tuberculosis and sarcoidosis," Proc. Natl. Acad. Sci. U.S.A., vol. 109, No. 20, 2012, pp. 7853-7858.
Oswald-Richter & Drake, "The etiologic role of infectious antigens in sarcoidosis pathogenesis," Semin. Respir. Crit. Care Med., vol. 31, No. 4, 2010, pp. 375-379.
Richter, et al., "Analysis of the Kveim-Siltzbach test reagent for bacterial DNA," Am. J. Respir. Crit. Care Med., vol. 159, No. 6, 1999, pp. 1981-1984.

(Continued)

*Primary Examiner* — James Martinell
(74) *Attorney, Agent, or Firm* — Lee & Hayes, P.C.; Tanya M. Harding; C. Rachal Winger

(57) ABSTRACT

Systems and methods to diagnose sarcoidosis are described. In addition to diagnosing sarcoidosis, the systems and methods can distinguish sarcoidosis from tuberculosis. Further disclosed is a cDNA library and methods of its use for reliably identifying sarcoidosis markers.

13 Claims, 24 Drawing Sheets

Specification includes a Sequence Listing.

(56) References Cited

OTHER PUBLICATIONS

Song, et al., "Mycobacterial catalase-peroxidase is a tissue antigen and target of the adaptive immune response in systemic sarcoidosis," J. Exp. Med., vol. 201, No. 5, 2005, pp. 755-767.

Stone, et al., "RNA-Seq for enrichment and analysis of IRF5 transcript expression in SLE," PLoS One, vol. 8, No. 1, 2013, e54487, pp. 1-16.

Talwar, et al., "Development of a T7 Phage Display Library to Detect Sarcoidosis and Tuberculosis by a Panel of Nove Antigens," EBioMedicine, vol. 2, No. 4, 2015, pp. 341-350.

Talwar, et al., "Novel T7 Phage Display Library Detects Classifiers for Active *Mycobacterium tuberculosis* Infection," Viruses, vol. 10, No. 375, 2018, pp. 1-13.

Talwar, et al., "T7 Phage Display Library a Promising Strategy to Detect Tuberculosis Specific Biomarkers," Mycobact. Dis., vol. 6, No. 2, 2016, pp. 1-8.

Zhang, et al., "Preliminary characterizations of a serum biomarker for sarcoidosis by comparative proteomic approach with tandem-mass spectrometry in ethnic Han Chinese patients," Respir. Res., vol. 14, No. 18, 2013, pp. 1-9.

Fridlender, et al., "Association between CD14 gene polymorphisms and disease phenotype in sarcoidosis", Respiratory Medicine, Science Direct, vol. 104, No. 9, 2010, pp. 1336-1343.

Ueda-Hayakawa, et al., "Elevated serum BAFF levels in patients with sarcoidosis: association with disease activity," Rheumatology, vol. 52, No. 9, 2013, pp. 1658-1666.

Invitation to Pay Additional Fees dated May 25, 2016 for International Application No. PCT/US16/21035.

Search Report and Written Opinion dated Aug. 26, 2016 for International Application No. PCT/US2016/021035.

Salmela, et al., "Algorithms for Weighted Matching", International Symposium on String Processing and Information Retrieval, 2007, pp. 276-286.

\* cited by examiner

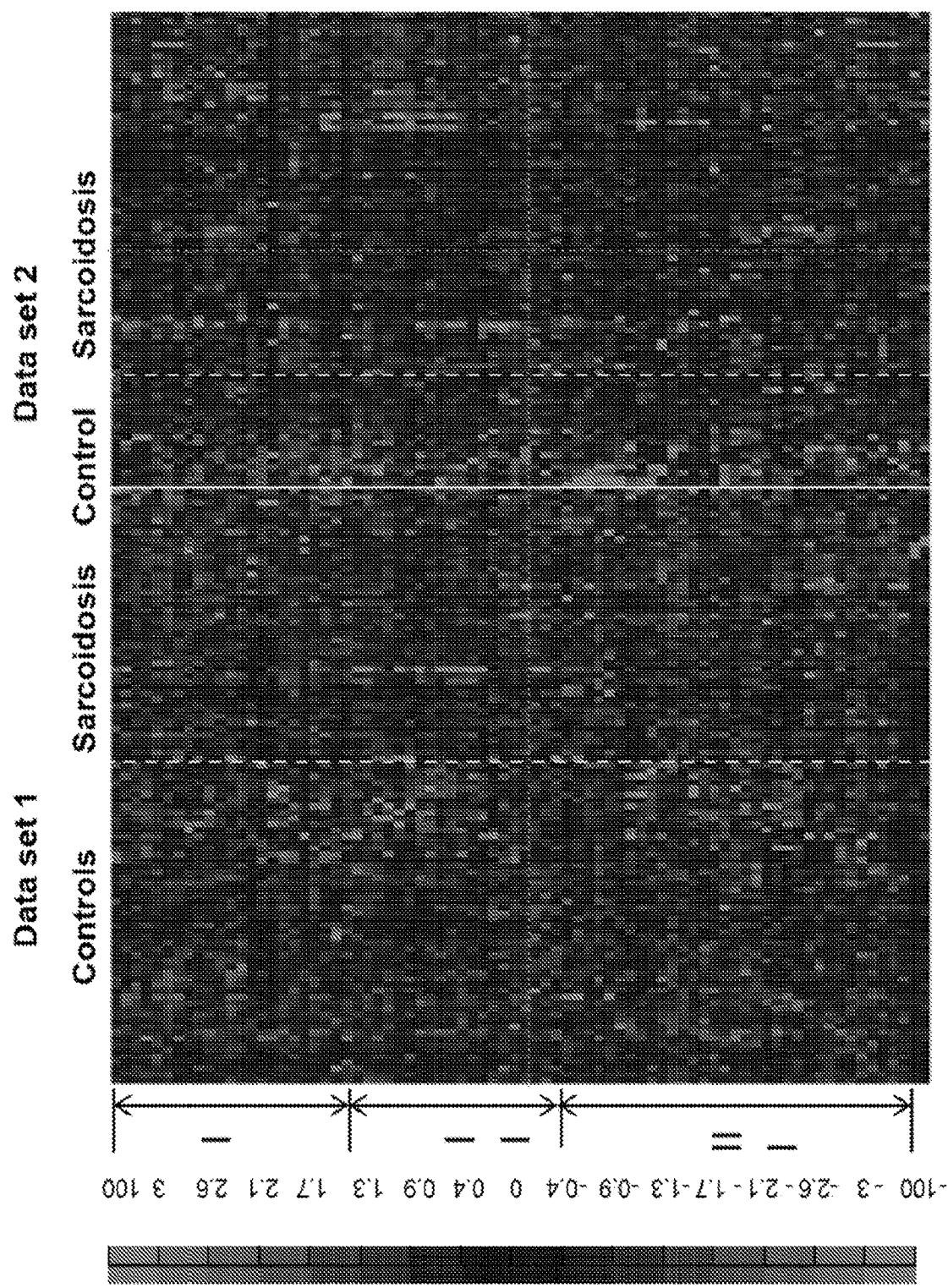

P51BP4-566 (TNFRSF21)

BAL: EcoRI-HindIII linkers
(SEQ ID NO: 1)

| cDNA | AA / TT | GCTTGAATTCAAGC / CGAACTTAAGTTCG | SEQ ID NO: 1 |

GCTTGAATTCAAGC
CGAACTTAAGTTCG

WBC: ALA modified (SEQ ID NO: 2)

| cDNA | AA / TT | GCTTGCTGAATTCAGCAAGC / CGAACGACTTAAGTCGTTCG | SEQ ID NO: 2 |

GCTTGCTGAATTCAGCAAGC
CGAACGACTTAAGTCGTTCG

MRC5: LEU modified (SEQ ID NO: 3)

| cDNA | AA / TT | GCTTAGTGAATTCACTAAG / CGAATCACTTAAGTGATTCG | SEQ ID NO: 3 |

GCTTAGTGAATTCACTAAG
CGAATCACTTAAGTGATTCG

EL-1 THR modified (SEQ ID NO: 4)

| cDNA | AA / TT | GCTTGTTGAATTCAACAAGC / CGAACAACTTAAGTTGTTCG | SEQ ID NO: 4 |

GCTTGTTGAATTCAACAAGC
CGAACAACTTAAGTTGTTCG

FIG. 8

| Rank | Clone and peptide size | Peptide sequences of mimotopes in-frame with T7 10B gene | Description of the sequences that Mimotopes mimic | Region of similarity of peptide |
|---|---|---|---|---|
| 1 | P53BP3_287 (9aa) | IQHQHLGQI (SEQ ID NO: 5) | Small inducible cytokine A21 precursor [Osmerus mordax] Sequence ID: gb\|ACI33984.1\| (SEQ ID NO: 6) | Id=7/7 (100%) Gaps=0/7 (0%) Length=110<br>Query 2  QHQHLGQ 8     (SEQ ID NO: 5, Amino Acids 2-8)<br>         QHQHLGQ        (SEQ ID NO: 8)<br>Sbjct 46 QHQHLGQ 52    (SEQ ID NO: 6, Amino Acids 46-52)<br><br>Id=7/9 (78%) Gaps=0/9 (0%) Length=333<br>Query 1  IQHQHLGQI 9   (SEQ ID NO: 5, Amino Acids 1-9)<br>         IQH HL Q       (SEQ ID NO: 9)<br>Sbjct 325 IQIHHLEQI 333 (SEQ ID NO: 7, Amino Acids 325-333) |
| 2 | P53BP3_281 (16aa) | AGISRELVDK LAAALE (SEQ ID NO: 10) | Chain A, Human Mecp1 Sequence ID: pdb\|5FUA (SEQ ID NO: 11) | Id=11/11 (100%) Gaps=0/11 (0%) Length=326<br>Query 6   ELVDKLAAALE 16  (SEQ ID NO: 10, Amino Acids 6-16)<br>          ELVDKLAAALE      (SEQ ID NO: 12)<br>Sbjct 310 ELVDKLAAALE 320 (SEQ ID NO: 11, Amino Acids 310-320) |
| 3 | P53BP4_388 (42aa) | SEYWMDPEG EMKPQRKGIS LNPEQWSQLK EQSDIDDAV RKL (SEQ ID NO: 13) | activated RNA polymerase II transcription cofactor 4 variant [Homo sapiens] Sequence ID: dbj\|BAD92611.1 (SEQ ID NO: 14) | Id=41/41 (100%) Gaps=0/41 (0%) Length=134<br>Query 2  EYWMDPEGEMKPQRKGISLNPEQWSQLKEQSDIDDAVRKL 42  (SEQ ID NO: 13, Amino Acids 2-42)<br>         EYWMDPEGEMKPQRKGISLNPEQWSQLKEQSDIDDAVRKL      (SEQ ID NO: 15)<br>Sbjct 94 EYWMDPEGEMKPQRKGISLNPEQWSQLKEQSDIDDAVRKL 134 (SEQ ID NO: 14, Amino Acids 94-134) |

FIG. 8 cont.

| | | | |
|---|---|---|---|
| 4 | P53BP4_596 (19aa) SENTKISRVK LAGRGGVCL (SEQ ID NO: 16) | RNA methyltransferase [Clostridium botulinum] Sequence ID: ref\|WP

FIG. 8 cont.

| | | | |
|---|---|---|---|
| 7 | P51BP3_47 (1768aa) | SARYKETRLK EKEDALTRTE LETLQKQKKV AKPKPEPVVY TPLETTYIQS YDHGTSEEIE EQMDDWLENR KNETQKKQAP EWTEEDLSQL TRSMVKFPCG TPGRWEKIAH ELGRSVTDVT TKAKLAAALE (SEQ ID NO: 31) | DnaJ (Hsp40) homolog, subfamily C, member 1 [Homo sapiens] Sequence ID: _____ (SEQ ID NO: 32) | Id=123/123 (100%) Gaps=0/123 (0%) Length=554<br><br>AKYKETRLKEEDALTRIELTLQKQKAVAKPKPEPVVYTPLETTYIQSYDHGTSEEIE query 61<br>AKYKETRLKEEDALTRIELTLQKQKKVAKPKPEPVVYTPLETTYIQSYDHGTSEEIE<br>AKYKETRLKEEDALTRIELTLQKQKKVAKPKPEPVVYTPLETTYIQSYDHGTSEEIE sbjct<br><br>EQMDDWLENRKNETQKKQAPEWTEEDLSQLTRSMVKFPCGTPGRWEKIAHELGRSVTDVTT query 121<br>EQMDDWLENRKNETQKKQAPEWTEEDLSQLTRSMVKFPCGTPGRWEKIAHELGRSVTDVTT<br>EQMDDWLENRKNETQKKQAPEWTEEDLSQLTRSMVKFPCGTPGRWEKIAHELGRSVTDVTT sbjct 369<br><br>122 KAK 124 query (SEQ ID NO: 31, Amino Acids 2-124)<br>KAK (SEQ ID NO: 33)<br>370 KAK 372 sbjct (SEQ ID NO: 32, Amino Acids 250-372) |
| 8 | P197BP4_885 (??aa) | AKFPPPPERR SGCTALAPSF RLVLS (SEQ ID NO: 34) | PREDICTED: amyloid beta A4 precursor protein-binding family B member 1 interacting protein [Nelspongus vulpinus] Sequence ID: _____ (SEQ ID NO: 35)<br><br>Human mRNA for translationally controlled tumor protein Sequence ID: _____ (SEQ ID NO: 36) | Id=8/8 (100%) Gaps=0/8 (0%) Length=853<br>Query 4 PPPPERRS 11 (SEQ ID NO: 34, Amino Acids 4-11)<br>PPPPERRS (SEQ ID NO: 37)<br>Sbjct 511 PPPPERRS 518 (SEQ ID NO: 35, Amino Acids 511-518)<br><br>Id=15/15 (100%) Gaps=0/15 (0%) Length=820<br>Query 6 PPFERRSGCTALAPSF 20 (SEQ ID NO: 34, Amino Acids 6-20)<br>PPFERRSGCTALAPSF (SEQ ID NO: 38)<br>Sbjct 2 PPFERRSGCTALAPSF 46 (SEQ ID NO: 36, Amino Acids 2-46) |
| 9 | P51BP4_577 (1?aa) | SQKTILQELR RLHHIPR (SEQ ID NO: 39) | Chordin growth factor-binding protein 2 precursor [Homo sapiens] Sequence ID: _____ (SEQ ID NO: 40) | Id=9/9 (100%) Gaps=0/9 (0%) Length=223<br>Query 6 LQELRRLHH 14 (SEQ ID NO: 39, Amino Acids 6-14)<br>LQELRRLHH (SEQ ID NO: 41)<br>Sbjct 96 LQELRRLHH 104 (SEQ ID NO: 40, Amino Acids 96-104) |

FIG. 8 cont.

| 10 | P19TBP4_755 (105aa) | NEANRFSEIL VLRVCYNFLF LWSLEGSCLI ERKETNRKFY CQDIRAYDIL FGDTPRPAQA ELYEILDSFTE KYEMEGQRIN AGPREQRRLP TKTIVGKSDL QS (SEQ ID NO: 42) | SH3 domain-containing YSC84-like protein 1 isoform 3 [Homo sapiens] Sequence ID: NP_689611.1 (SEQ ID NO: 43) | Id=66/79 (84%) Gaps=3/79 (3%) Length=227 |
|---|---|---|---|---|

Query 24 SLEGSCLIERKETNRKFYCQDIRAYDILFGDTPRPAQAELYEILDSFTEKYEMEGQRIN 82

Sbjct 67 SLEGSCLIERKETNRKFYCQDIRAYDILFGDTPRPAQAEDLYEILDSFTEKYEMEGQRIN 126

Query 83 A--GPREQRRLPTKTIVGK 99 (SEQ ID NO: 42, Amino Acids 24-99)
          A  REQR+     K + K              (SEQ ID NO: 44)
Sbjct 127 ARKAAREQRASSAKELPPK 143 (SEQ ID NO: 43, Amino Acids 67-145)

FIG. 9

| Rank | Clone and Peptide size | Peptide sequences of mimotopes in-frame with T7 10B gene | Description of the sequences that mimotopes mimic | Region of similarity of peptide |
|---|---|---|---|---|
| 1 | P53BP3_174 (9aa) | IQHQHLGQI (SEQ ID NO: 45) | Ferredoxin [Mycobacterium tuberculosis] Sequence ID: gb|AH1224 621.1 (SEQ ID NO: 46) | Id=6/6 (100%) Gaps=0/6 (0%) Length=133<br><br>Query 2 QHQHLG 7 (SEQ ID NO: 45, Amino Acids 2-7)<br>QHQHLG (SEQ ID NO: 47)<br>Sbjct 56 QHQHLG 61 (SEQ ID NO: 46, Amino Acids 56-61) |
| 2 | P53BP4_610 (161aa) | LYDPHPNPIEV RNYSRLKPGY RWERQLYFRS KLTMHTAFDR KDNAHPAEVT ALGISKDHSRI LVQDSRGRVFS WSVSDQPGRS AADHWVKDEG GDSCSGCSVRF SLTERRHHCRM CQHLFCQKCSR FQSEIKRLKISS PVRVCNCYYM LQHEEQSXXGP RMC (SEQ ID NO: 48) | WDFY3 protein [Homo sapiens] Sequence ID: gb|AAH13274. 2| (SEQ ID NO: 49) | Id=158/163 Gaps=0/163 (1%) Length=437<br><br>Query 1 LYDPHPNPIEVRNYSRLKPGYRWERQLYFRSKLTMHTHAFDRKDNAHPAEVTALGISKD 60<br>HTAFDRKDNAHPAEVTALGISKD<br>Sbjct 275 LSHPHPNPIEVRNYSRLKPGYRWERQLYFRSKLTM---HTAFDRKDNAHPAEVTALGISKD 334<br><br>Query 61 HSRIL VQDSRGRVFSWSVSDQPGRSAADHWVKDEGGDSCSGCSVRFSLTERRHHCRMCQ 120<br>HSRIL VQDSRGRVFSWSVSDQPGRSAADHWVKDEGGDSCSGCSVRFSLTERRHHCRMCQ<br>Sbjct 335 HSRIL VQDSRGRVFSWSVSDQPGRSAADHWVKDEGGDSCSGCSVRFSLTERRHHCRMCQ 394<br><br>Query 121 LFCQKCSRFQSEIKRLKISSPVRVCNCYYMLQHEEQSXXGPRMC 163<br>LFCQKCSRFQSEIKRLKISSPVRVC NCYYMLQHEEQS GPRMC<br>Sbjct 395 LFCQKCSRFQSEIKRLKISSPVREVQQRCYYMLQHEEGSEIAPRMC 437<br><br>(SEQ ID NO: 48, Amino Acids 1-165)<br>(SEQ ID NO: 50)<br>(SEQ ID NO: 49, Amino Acids 275-437) |

FIG. 9 cont.

| | | | |
|---|---|---|---|
| 3 | P51BP3_266 (27aa) | VDKSVLLSLQR KKYGAVGSLS OSTGGH (SEQ ID NO: 51) | membrane protein [Mycobacterium tuberculosis] Sequence ID: ref|WP_031284 111.1 (SEQ ID NO: 52) | Id=6/6 (100%) Gaps=0/6 (0%) Length=942<br>Query 5  VLSLG 10    (SEQ ID NO: 51, Amino Acids 5-10)<br>        VLSLG      (SEQ ID NO: 53)<br>Sbjct 802 VLSLG 807  (SEQ ID NO: 52, Amino Acids 802-807) |
| 4 | P51BP3_166 (172aa) | SASTTEPDFQK DILACRLNQK KQAYDIFLMAK EQMIVPMAETY SNLIKLLMSED YFTQAMEVKA FAETHIKGFTL NDAANSRLIIT QVRRDYLKEA VTTLKTVLDQ QQTPSRLAVTR VIQALAMKGD VEMEVVQ KMLNGLEDSIG LSKMVTIMMIA LAQIKNNNIDA ARLAAALE (SEQ ID NO: 54) | keratin-6A PREDICTED: containins protein [Homo sapiens] Sequence ID: gb|AAA57339. 1 (SEQ ID NO: 55) | Id=170/170 (100%) Gaps=0/170 (0%) Length=1273<br>Query 1   SASTTEPDFQKDILACRLNQKKGAYDIFLMAKEQMVFMAETYSNLELLMSEDYFTQA 60<br>          SASTTEPDFQKDILACRLNQKKGAYDIFLMAKEQMVFMAETYSNLELLMSEDYFTQA<br>Sbjct 807 SASTTEPDFQKDILACRLNQKKGAYDIFLMAKEQMVFMAETYSNLELLMSEDYFTQA 966<br><br>Query 61  MEVKAFAETHIKGFTLNDAANSRLIITQVRRDYLKEAVTTLKTVLDQQQTPSRLAVTRVI 120<br>          MEVKAFAETHIKGFTLNDAANSRLIITQVRRDYLKEAVTTLKTVLDQQQTPSRLAVTRVI<br>Sbjct 966 MEVKAFAETHIKGFTLNDAANSRLIITQVRRDYLKEAVTTLKTVLDQQQTPSRLAVTRVI 1025<br><br>Query 121 QALAMKGDVEMEVVQKMLNGLEDSIGLSKMVTIMMIALAQKNNNIDAA 170 (SEQ ID NO: 54, Amino Acids 1-170)<br>          QALAMKGDVEMEVVQKMLNGLEDSIGLSKMVTIMMIALAQKNNNIDAA     (SEQ ID NO: 56)<br>Sbjct 1026 QALAMKGDVEMEVVQKMLNGLEDSIGLSKMVTIMMIALAQKNNNIDAA 1075 (SEQ ID NO: 55, Amino Acids 906-1075) |

FIG. 9 cont.

| | | | |
|---|---|---|---|
| 5 | P51BP4_704 (49aa) | D A P S P L P E T T E<br>N V V C A L G L T V<br>G L V G H G T I P I I<br>R G V R K S N A A E<br>R G P L<br>(SEQ ID NO: 57) | HLA-DR alpha [Homo sapiens] Sequence ID: gb\|AAC32887. 1\|AF281159_1 (SEQ ID NO: 58) | Id=48/49 (98%) Gaps=0/49 (0%) Length=50<br>Query 1 DAPSPLPETTENVVCALGLTVGLVGHGTIPIIRGVRKSNAAERGPL 49 (SEQ ID NO: 57, Amino Acids 1-49)<br>      DAPSPLPETTENVVCALGLTVGLVGHGTIPIIRG RKSNAAERGPL    (SEQ ID NO: 59)<br>Sbjct 2 DAPSPLPETTENVVCALGLTVGLVGHGTIPIIRGLRKSNAAERGPL 50 (SEQ ID NO: 58, Amino Acids 2-50) |
| 6 | P197BP4_76 3 (17aa) | D L S S E V A T H Q P<br>I I A C L P<br>(SEQ ID NO: 60) | transketolase [Mycobacterium tuberculosis] Sequence ID: ref\|WP_0167 21352.1\| (SEQ ID NO: 61) | Id=5/5 (100%) Gaps=0/5 (0%) Length=611<br>Query 8 THQPI 12 (SEQ ID NO: 60, Amino Acids 8-12)<br>      THQPI    (SEQ ID NO: 62)<br>Sbjct 453 THQPI 457 (SEQ ID NO: 61, Amino Acids 453-457) |
| 7 | P51BP4_563 (14aa) | L Q A C F P Q I L R G<br>S L<br>(SEQ ID NO: 63) | dihydroxy-acid dehydratase [Mycobacterium tuberculosis] Sequence ID: ref\|WP_0166 1452.1\| (SEQ ID NO: 64) | Id=6/7 (86%) Gaps=0/7 (0%) Length=575<br>Query 8 ILRGSLA 14 (SEQ ID NO: 63, Amino Acids 8-14)<br>      IL GSLA    (SEQ ID NO: 65)<br>Sbjct 400 ILKGSLA 406 (SEQ ID NO: 64, Amino Acids 400-406) |

FIG. 9 cont.

| | | | |
|---|---|---|---|---|
| 8 | P51BP3_113 (16aa) | AGISRELVDEI AAALE (SEQ ID NO: 66) | Class: A, Mycobacterium Tuberculosis Escherichia, Rita Sequence ID: pdb|OBR|A (SEQ ID NO: 67) | Id=7/7 (100%) Gaps=0/7 (0%) Length=174<br>Query 10  ELAAALE  16  (SEQ ID NO: 66, Amino Acids 10-16)<br>         ELAAALE      (SEQ ID NO: 68)<br>Sbjct 162 ELAAALE 168  (SEQ ID NO: 67, Amino Acids 162-168) |
| 9 | P51BP3_200 (209aa) | SSSTPLSNGPL NGDVDYTGQQ FDQISNRTGKQ EAQAGP WFFSSSQTQPA VRTQNGVSERE QNGFSVKSSP NPFVGSPPKGL SIQNGVKQDLE SSVQSSPHDSI AIPPPQSTKPG NDILASDIFAP VSEPSGQASP TQQPTALQPNP LDLFKTSAPAP VGPLVGLGQVT VTLPQAGPW KTASLVFMQSP SWXLAAALE (SEQ ID NO: 69) | disheveled homolog 2 isoform 2 [Homo sapiens] Sequence ID: ref|NP_004131 0020.1| (SEQ ID NO: 70) | Id=201/208 (97%) Gaps=0/208 (0%) Length=749<br>Query 1   SSSTPLSNGPLNGDVDYTGQQFDQISNRTGKQEAQAGPWFFSSSQTQPAVRTQNGVSERE  60<br>          SSSTPLSNGPLNGDVDYTGQQFDQISNRTGKQEAQAGPWFFSSSQTQPAVRTQNGVSERE<br>Sbjct 305 SSSTPLSNGPLNGDVDYTGQQFDQISNRTGKQEAQAGPWFFSSSQTQPAVRTQNGVSERE 364<br>Query 61  QNGFSVKSSPNPFVGSPPKGLSIQNGVKQDLESSVQSSPHDSIAIPPPQSTKPGCRT 120<br>          QNGFSVKSSPNPFVGSPPKGLSIQNGVKQDLESSVQSSPHDSIAIPPPQSTKPGAGRT<br>Sbjct 365 QNGFSVKSSPNPFVGSPPKGLSIQNGVKQDLESSVQSSPHDSIAIPPPQSTKPGAGRT 424<br>Query 121 AKSSANDLLASDEAPPVSEPSGQASPTQQPTALQPNPLDLFKTSAPAPVGPLVGLGQVT 180<br>          AKSSANDLLASDEAPPVSEPSGQASPTQQPTALQPNPLDLFKTSAPAPVGPLVGLGQVT<br>Sbjct 425 AKSSANDLLASDEAPPVSEPSGQASPTQQPTALQPNPLDLFKTSAPAPVGPLVGLGQVT 484<br>Query 181 VTLPQAGPWKTASLVFMQSPSWXLAAALE 208  (SEQ ID NO: 69, Amino Acids 1-208)<br>          VTLPQAGPW TASLVFMQSPS A+         (SEQ ID NO: 71)<br>Sbjct 485 VTLPQAGPWKTASLVFMQSPSALPGAAAM 512  (SEQ ID NO: 70, Amino Acids 305-512) |

FIG. 9 cont.

| 10 | P51BP4_622 (122aa) | AAAAMDVFLM IRRHKTTIFTD AKESSTVFELK RIVEGILKRPP DEQRLYKDDQ LLDDGKTLGEC GFTSQTARPQ APATVGLAFR ADDTFEALCIE PFSSPPELPDV MKPQDSGSSA NEQAVQ (SEQ ID NO: 72) | transcription elongation factor B polypeptide 2 isoform a [Homo sapiens] Sequence ID: [illegible] (SEQ ID NO: 73) | Id=118/118 (100%) Gaps=0/118 (0%) Length=118<br><br>Query 1 MDVFLMIRRHKTTIFTDAKESSTVFELKRIVEGILKRPPDEQRLYKDDQLLDDGKTLGEC 64<br>MDVFLMIRRHKTTIFTDAKESSTVFELKRIVEGILKRPPDEQRLYKDDQLLDDGKTLGEC<br>Sbjct 1 MDVFLMIRRHKTTIFTDAKESSTVFELKRIVEGILKRPPDEQRLYKDDQLLDDGKTLGEC 60<br><br>Query 65 GFTSQTARPQAPATVGLAFRADDTFEALCIEPFSSPPELPDVMKPQDSGSSANEQAVQ 122<br>GFTSQTARPQAPATVGLAFRADDTFEALCIEPFSSPPELPDVMKPQDSGSSANEQAVQ<br>Sbjct 61 GFTSQTARPQAPATVGLAFRADDTFEALCIEPFSSPPELPDVMKPQDSGSSANEQAVQ 118<br><br>(SEQ ID NO: 72, Amino Acids 5-122)<br>(SEQ ID NO: 74)<br>(SEQ ID NO: 73, Amino Acids 1-118) |

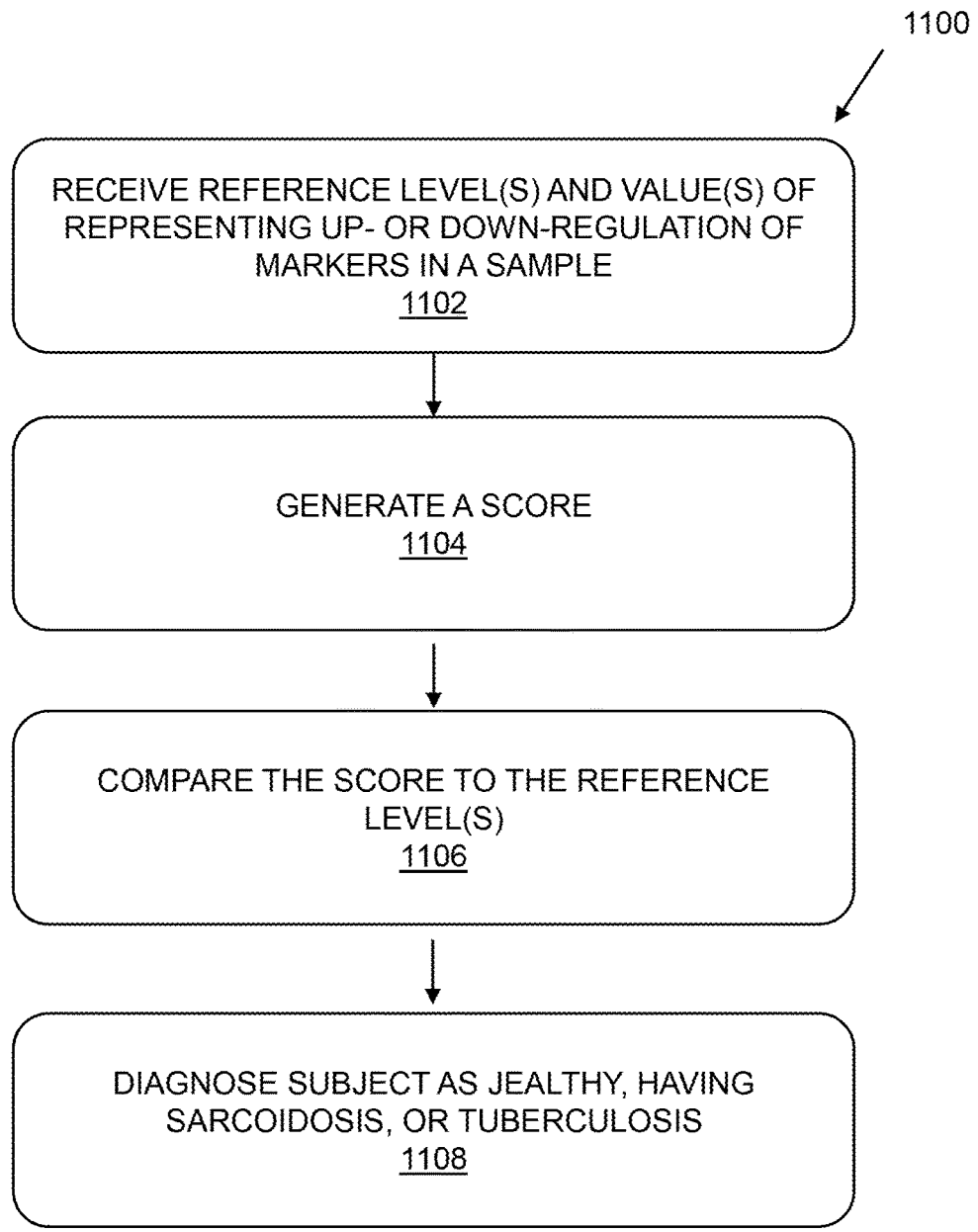

SYSTEMS AND METHODS TO DIAGNOSE SARCOIDOSIS AND IDENTIFY MARKERS OF THE CONDITION

CROSS REFERENCE TO RELATED APPLICATION

The present application is the U.S. National Stage of International Patent Application No. PCT/US2016/021035, filed on Mar. 4, 2016, which claims the benefit of U.S. Provisional Patent Application No. 62/128,436, filed on Mar. 4, 2015, which is incorporated herein by reference in its entirety as if fully set forth herein.

STATEMENT OF GOVERNMENT INTEREST

This invention was made with government support under grant HL104481awarded by the National Institutes of Health. The government has certain rights in the invention.

FIELD OF THE DISCLOSURE

The current disclosure provides systems and methods to diagnose sarcoidosis. In addition to diagnosing sarcoidosis, the systems and methods can distinguish sarcoidosis from tuberculosis. Further disclosed is a cDNA library and methods of its use for reliably identifying sarcoidosis markers.

BACKGROUND OF THE DISCLOSURE

Sarcoidosis, also called sarcoid, is a disease involving abnormal collections of inflammatory cells (granulomas) that can form as nodules in multiple organs. The granulomas are most often located in the lungs or its associated lymph nodes. The disease seems to be caused by an immune reaction to an infection or some other trigger.

Diagnosis of sarcoidosis is challenging as the signs and symptoms of the condition are very broad, sometimes mimicking symptoms of other diseases. Further, symptoms can vary widely according to the organ system affected by the disorder. This variance can lead to a delay in diagnosis, or inappropriate treatment, therefore demonstrating a need for improved sarcoidosis diagnostic techniques.

The symptoms of sarcoidosis can also particularly resemble those caused by infection with tuberculosis. Thus, ability of a diagnostic to reliably distinguish between sarcoidosis and tuberculosis infection would allow faster treatment of each condition, resulting in better treatment outcomes.

SUMMARY OF THE DISCLOSURE

The present disclosure provides systems and methods to diagnose sarcoidosis in a subject. The systems and methods can distinguish a sarcoidosis subject from a healthy subject and/or a subject having tuberculosis. The systems and methods include diagnostic kits. The systems and methods also include a cDNA library to identify markers for sarcoidosis or tuberculosis diagnosis as well as methods of using the cDNA library to identify such markers, among others.

BRIEF DESCRIPTION OF THE FIGURES

FIG. 2A shows a heatmap generated by applying meta-analysis using microarray analysis of 2 separate data sets derived from 115 sarcoidosis patients and 64 healthy controls. Data reflects 259 antigens expressed significantly differently between healthy controls and sarcoidosis subjects in immunoscreening using sera. The 259 antigens were further divided into three categories according to the AW-OC method. I: 78 antigens were consistently up- or down-regulated in sarcoidosis in both datasets; II: 115 antigens were up- or down-regulated in sarcoidosis in the second dataset only; III: 66 antigens were up- or down-regulated in sarcoidosis in the first dataset only.

FIG. 5B shows an enlarged version of clone identifiers to increase legibility of FIG. 5A.

FIG. 6 shows modified linkers distinguishing between the origins of each library. Each cDNA library was tagged with a modified linker: ECOR1/HindIII was used for BAL cDNA, ALA for WBC cDNA, LEU for MARCS cDNA and THR for EL1 cDNA.

FIG. 8 shows sequence analysis of the top 10 sarcoid phage clones using NCBI BLAST.

FIG. 9 shows sequence analysis of the top 10 TB phage clones using NCBI BLAST.

FIG. 11 shows an illustrative process for diagnosing sarcoidosis.

DETAILED DESCRIPTION

Figure 1:
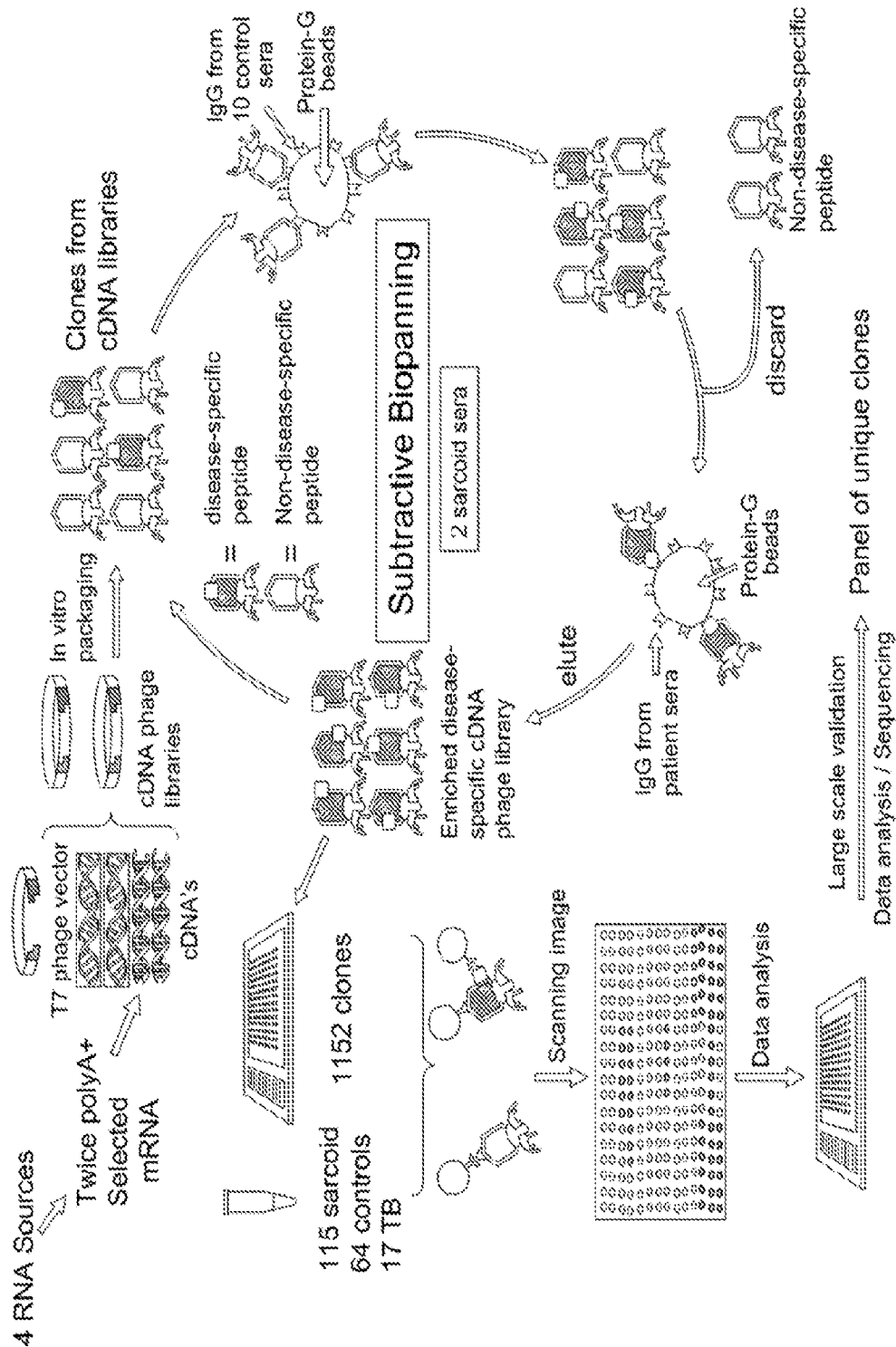
FIG. 1 depicts a schematic diagram of identification of sarcoidosis antigens. The process of combining phage-display technology, protein microarray and bioinformatics tools to select a panel of novel clones for the diagnosis of sarcoidosis was used. A cDNA library was constructed from a pool of total RNA isolated from 20 bronchoalveolar cells (BAL) samples and 36 white blood cell (WBC) samples from sarcoid patients, and then combined with RNA extracts from cultured human monocytes and human embryonic fibroblasts. After digestion, the cDNA library was inserted into the T7 phage vector and packaged into T7 phages to generate a sarcoid cDNA-phage-display library. Several rounds of biopannings of the library were performed with pooled control sera for negative selection, and with sarcoid sera for positive enrichments. After four rounds of biopanning, enriched sarcoid specific peptide clones were cultured onto LB agar plates. A total of 1152 single colonies, including positive and negative clones were randomly picked and propagated into 96-well plates. Phage-clone lysates were then printed robotically onto coated glass slides to create a sarcoid-phage-protein microarray. Cy5 (red fluorescent dye)-labeled antihuman antibody was used to detect IgGs in human serum that were reactive to peptide clones, and a Cy3 (green fluorescent dye)-labeled antibody was used to detect the phage capsid protein in order to normalize for spotting. Thus, if a phage clone carried a peptide reactive to human IgG, the spot remains green suggesting an unreactive clone. A total of 115 sarcoid sera, 64 healthy control sera and 17 TB sera were tested on the 1152 phage peptide microarray. Bioinformatically analyzed data identified 259 antigens with the highest level of differentiation between sarcoidosis and healthy controls.

Sarcoidosis is a multisystem granulomatous inflammatory disease. The disease is typically characterized by the formation of small, granular inflammatory lesions or granulomas (e.g., non-caseating granulomas) in a variety of organs, and/or the presence of immune responses (e.g., presence of CD4+ T lymphocytes and macrophages) in affected tissues or organs. Granulomatous inflammation may be attributed to the accumulation of monocytes, macrophages, and a pronounced Th1 response and activated T-lymphocytes, with elevated production of TNFα, IL-2, IL-12, IFNγ, IL-1, IL-6 or IL-15.

Exemplary subtypes of sarcoidosis include systemic sarcoidosis, Lofgren's syndrome, pulmonary sarcoidosis, cutaneous sarcoidosis, neurosarcoidosis, cardiac sarcoidosis, ocular sarcoidosis, hepatic sarcoidosis, musculoskeletal sarcoidosis, renal sarcoidosis, or sarcoidosis with the involvement of other organs or tissues.

Systemic sarcoidosis is sarcoidosis with multiple organ involvement. Symptoms of systemic sarcoidosis include aches, arthritis, chills, dry mouth, enlarged lymph glands (e.g., armpit lump), fatigue, fever, loss of appetite, night sweats, nosebleed, pains, persistent cough, malaise, shortness of breath, weakness, and weight loss. Because systemic sarcoidosis involves multiple organs, symptoms described below for other more particular types of sarcoidosis can also be relevant to systemic sarcoidosis.

Lofgren's syndrome represents an acute presentation of systemic sarcoidosis, typically characterized by the triad of erythema nodosum, bilateral hilar denopathy and arthritis or arthralgias. It can also be accompanied by fever.

Pulmonary sarcoidosis refers to sarcoidosis that affects pulmonary tissues or organs (e.g., lungs). Symptoms of pulmonary sarcoidosis usually include normal, abnormal or deteriorating lung function; abnormal lung stiffness; bleeding from the lung tissue; cough; decreased lung volume; decreased vital capacity (full breath in, to full breath out); enlarged lymph nodes in the chest; granulomas in alveolar septa, bronchiolar, and/or bronchial walls; higher than normal expiratory flow ratios; an increased FEVs/FVC ratio; limited amount of air drawn into the lungs; loss of lung volume; obstructive lung changes; pulmonary hypertension; pulmonary failure; scarring of lung tissue; and/or shortness of breath.

Cutaneous sarcoidosis is a complication of sarcoidosis with skin involvement. Cutaneous sarcoidosis includes annular sarcoidosis, erythrodermic sarcoidosis, hypopigmented sarcoidosis, ichthyosiform sarcoidosis, morpheaform sarcoidosis, mucosal sarcoidosis, papular sarcoid, scar sarcoid, subcutaneous sarcoidosis and ulcerative sarcoidosis. Symptoms of cutaneous sarcoidosis include erythema nodosum (e.g., raised, red, firm skin sores, cellulitis, furunculosis or other inflammatory panniculitis); hair loss; lupus pernio (e.g., scar or discoid lupus erythematosus); maculopapular eruptions; nodular lesions; papules (e.g., granulomatous rosacea, acne or benign appendageal tumors); skin lesions; skin plaques (e.g., psoriasis, lichen planus, nummular eczema, discoid lupus erythematosus, granuloma annulare, cutaneous T-cell lymphoma, Kaposi's sarcoma or secondary syphilis); skin rashes, and/or scars becoming more raised.

Neurosarcoidosis or neurosarcoid refers to sarcoidosis in which inflammation and abnormal deposits occur in the brain, spinal cord, and any other areas of the nervous system. Symptoms of neurosarcoidosis can include abnormal or loss of sense of smell; abnormal or loss of sense of taste; carpal tunnel syndrome; changes in menstrual periods; confusion; decreased hearing; delirium; dementia; disorientation; dizziness; double vision or other vision problems or changes; excessive thirst; excessive tiredness (e.g., fatigue); facial palsy, weakness or drooping; headache; high urine output; hypopituitarism; loss of bowel or bladder control; muscle weakness; paraplegia; psychiatric disturbances; radicular pain; retinopathy; seizures; sensory losses; speech impairment; and/or vertigo.

The systems and methods disclosed herein can be used to diagnose sarcoidosis. In particular embodiments, the diagnosed sarcoidosis is systemic sarcoidosis, pulmonary sarcoidosis, cutaneous sarcoidosis, Lofgren's syndrome, neurosarcoidosis, cardiac sarcoidosis, ocular sarcoidosis, hepatic sarcoidosis, musculoskeletal sarcoidosis, renal sarcoidosis, or sarcoidosis with the involvement of other organs or tissues. In more particular embodiments, the systems and methods disclosed herein can be used to diagnose pulmonary sarcoidosis, neurosarcoidosis, and/or ocular sarcoidosis.

Typically, a sarcoidosis patient will present with symptoms described above or clinical features set out in the Statement on Sarcoidosis published by the American Thoracic Society (Am. J. Respir. Crit. Care Med. 1999; 160(2): 736-55). Sarcoidosis patients may often, however, be asymptomatic. Further the common symptoms of sarcoidosis are vague, and can sometimes be similar to symptoms of numerous other conditions including lymphoma and tuberculosis. Thus, diagnosis is difficult.

Currently, subjects with suspected sarcoidosis are typically assessed with a chest assessment for pulmonary involvement, as the vast majority of sarcoidosis subjects have pulmonary involvement. These assessments are generally based upon a bronchoscopy with biopsy; chest X-ray; CT scan; CT-guided biopsy; lung gallium (Ga) scan; mediastinoscopy; open lung biopsy; PET scan and/or a radiograph. Radiographs are typically assigned a stage of 0-4 according to the presence or absence of hilar adenopathy and parenchymal disease. Thus there are five stages: Stage 0: no visible intrathoracic findings; Stage 1: bilateral hilar lymphadenopathy (BHL), which may be accompanied by paratracheal adenopathy/lung fields are clear of infiltrates; Stage 2: bilateral hilar adenopathy (BHL) accompanied by parenchymal infiltration; Stage 3: parenchymal infiltration without bilateral hilar adenopathy (BHL); or Stage 4: advanced pulmonary fibrosis with evidence of honey-combing, hilar retraction, bullae, cysts, and emphysema.

The present disclosure provides significant advancements in the diagnosis of sarcoidosis because diagnosis can be achieved with, for example, a blood test and can distinguish sarcoidosis subjects from healthy subjects and/or subjects having tuberculosis.

The systems and methods disclosed herein were achieved by creating and screening a complex cDNA library. Particularly, a heterologous cDNA library derived from bronchoalveolar cell (BAL) samples and total white blood cells (WBC) from sarcoidosis patients was developed. Both sarcoid-derived libraries were combined with cultured human monocytes and embryonic lung fibroblast cDNA libraries to build a complex sarcoidosis library (CSL). Differential biopanning for negative and positive selection was performed using sera from healthy controls to remove non-specific IgG, and sarcoidosis sera for selective enrichment. Four rounds of biopannings were performed and the selected phage libraries were used for microarray immunoscreening. Each cycle of biopanning included passing the entire phage library through protein G beads coated with IgG from pooled sera of healthy controls, then passing through beads coated with IgGs from individual serum of sarcoid subjects.

After biopanning, phage clones were randomly selected and amplified and their lysates were arrayed in quintuplicates onto slides (Grace Biolabs, OR) using the ProSys 5510TL robot (Cartesian Technologies, CA). It was tested whether this novel library representing relevant antigens would specifically recognize high IgG titer in sera of sarcoidosis subjects.

Using bioinformatics tools, a large number of markers with high sensitivity and specificity were identified that discriminate among the sera of patients with sarcoidosis, healthy controls and TB. Using the integrative-analysis method that combines results from two independent trials, clones that significantly differentiated sarcoidosis from controls were identified. Similarly, clones that differentially reacted with TB sera and not with sarcoidosis or control sera were identified. Furthermore, the top 10 discriminating antigens for TB and sarcoidosis were sequenced and homologies were identified in a public data base. These data indicates development of a unique library enabling the detection of highly significant antigens to discriminate between patients with sarcoidosis and tuberculosis.

An antigen is a substance that induces an immune response. Accordingly, the antigens detected from the library are markers useful for diagnosing sarcoidosis and TB.

The systems and methods diagnose sarcoidosis by assaying a sample obtained from a subject for the up- or down-regulation of one or more markers associated with sarcoidosis. The markers are selected from Small inducible cytokine A21 precursor (CCL21); Methionine aminopeptidase 1 (Metap1); Activated RNA polymerase II transcription cofactor variant 4 (PC4); RNA methyltransferase (CLI_3190); Tumor necrosis factor receptor superfamily member 21 precursor (also known as death receptor 6 (DR6)) (TNFRSF21); Monocyte differentiation antigen CD14 (CD14); DnaJ (Hsp40) homolog subfamily C member 1 precursor (DNAJC1); Amyloid β A4 precursor protein-binding family B member 1-interacting protein (APBB1); Fibroblast growth factor binding protein 2 precursor (FGFBP-2); SH3 domain-containing YSC84 like protein 1 (SH3YL1); thioester reductase [*Pseudomonas fluorescens*] (PFWH6_0117); histidine kinase [*Pseudomonas fluorescens*] (PFL_3193); *Homo sapiens* chromatin modifying protein 4B (CHMP4B); hypothetical protein [*Porphyromonas somerae*] Peptidase family C39 mostly contains bacteriocin-processing endopeptidases from bacteria; truncated HIC1 protein [*Homo sapiens*] (H1C1); replication protein [*Mycobacterium*] (MVAC_06252); *Homo sapiens* ribosomal protein S2 (RPS2); triosephosphate isomerase [*Mycobacterium tuberculosis*] (tpiA); membrane protein [*Mycobacterium tuberculosis*] (Rv2563); serine/threonine protein kinase [*Mycobacterium tuberculosis*] (Rv0410C); PPE family protein [*Mycobacterium tuberculosis* RGTB423] (MRGA423_16320); rRNA methyltransferase [*Mycobacterium tuberculosis*] (Rv0881); peroxisome biogenesis factor isoform 1 [*Homo sapiens*] (PEX10); sulfate ABC transporter permease [*Mycobacterium tuberculosis*] (CysU); and/or D-alpha-D-heptose-7-phosphate kinase [*Mycobacterium tuberculosis*] (hddA).

In particular embodiments, the systems and methods diagnose sarcoidosis by assaying a sample obtained from a subject for the up- or down-regulation of two or more; three or more; four or more; five or more; six or more; seven or more; eight or more; nine or more or ten or more markers associated with sarcoidosis disclosed herein. In further embodiments, the systems and methods diagnose sarcoidosis by assaying a sample obtained from a subject for the up- or down-regulation of two; three; four; five; six; seven; eight; nine or ten markers associated with sarcoidosis disclosed herein.

In one embodiment, the markers include (hereafter referred to by gene abbreviations for brevity) CCL21; Metap1; PC4; CLI_3190; TNFRSF21; CD14; DNAJC1; APBB1; FGFBP-2; and SH3YL1. In another embodiment, the markers include CCL21; Metap1; PC4; CLI_3190; TNFRSF21; and APBB1. In another embodiment, the markers include CCL21, PC4, CLI3190, DNAJC1, APBB1, FGFBP-2 and SH3YL1. In another embodiment, the markers include CCL21; Metap1; PC4; CLI_3190; TNFRSF21; CD14; DNAJC1; APBB1; FGFBP-2; or SH3YL1. In another embodiment, the markers include CCL21; Metap1; CLI-3190; APBB1; and SH3YL1.

In other embodiments, the markers include CCL21 in combination with two, three, four, five, six, seven, eight or nine markers selected from: Metap1; PC4; CLI_3190; TNFRSF21; CD14; DNAJC1; APBB1; FGFBP-2; and SH3YL1.

In other embodiments, the markers include Metap1 in combination with two, three, four, five, six, seven, eight or nine markers selected from: CCL21; PC4; CLI_3190; TNFRSF21; CD14; DNAJC1; APBB1; FGFBP-2; and SH3YL1.

In other embodiments, the markers include PC4 in combination with two, three, four, five, six, seven, eight or nine markers selected from: CCL21; Metap1; CLI_3190; TNFRSF21; CD14; DNAJC1; APBB1; FGFBP-2; and SH3YL1.

In other embodiments, the markers include CLI_3190 in combination with two, three, four, five, six, seven, eight or nine markers selected from: CCL21; Metap1; PC4; TNFRSF21; CD14; DNAJC1; APBB1; FGFBP-2; and SH3YL1.

In other embodiments, the markers include TNFRSF21 in combination with two, three, four, five, six, seven, eight or nine markers selected from: CCL21; Metap1; PC4; CLI_3190; CD14; DNAJC1; APBB1; FGFBP-2; and SH3YL1.

In other embodiments, the markers include CD14 in combination with two, three, four, five, six, seven, eight or nine markers selected from: CCL21; Metap1; PC4; CLI_3190; TNFRSF21; DNAJC1; APBB1; FGFBP-2; and SH3YL1.

In other embodiments, the markers include DNAJC1 in combination with two, three, four, five, six, seven, eight or nine markers selected from: CCL21; Metap1; PC4; CLI_3190; TNFRSF21; CD14; APBB1; FGFBP-2; and SH3YL1.

In other embodiments, the markers include APBB1 in combination with two, three, four, five, six, seven, eight or nine markers selected from: CCL21; Metap1; PC4; CLI_3190; TNFRSF21; CD14; DNAJC1; FGFBP-2; and SH3YL1.

In other embodiments, the markers include FGFBP-2 in combination with two, three, four, five, six, seven, eight or nine markers selected from: CCL21; Metap1; PC4; CLI_3190; TNFRSF21; CD14; DNAJC1; APBB1; and SH3YL1.

In other embodiments, the markers include SH3YL1 in combination with two, three, four, five, six, seven, eight or nine markers selected from: CCL21; Metap1; PC4; CLI_3190; TNFRSF21; CD14; DNAJC1; APBB1; and FGFBP-2.

In other embodiments, the markers exclude a marker selected from CCL21; Metap1; PC4; CLI_3190; TNFRSF21; CD14; DNAJC1; APBB1; FGFBP-2; and SH3YL1. In other embodiments, the markers exclude CCL21. In other embodiments, the markers exclude Metap1. In other embodiments, the markers exclude PC4. In other embodiments, the markers exclude CLI_3190. In other embodiments, the markers exclude TNFRSF21.

In other embodiments, the markers exclude CD14. In other embodiments, the markers exclude DNAJC1. In other embodiments, the markers exclude APBB1. In other embodiments, the markers exclude FGFBP-2. In other embodiments, the markers exclude SH3YL1. In other embodiments, the markers exclude one or more of Metap 1; TNFRSF21; and CD14. In other embodiments, the markers exclude Metap 1; TNFRSF21; and CD14.

Any of the embodiments described above can additionally include a marker selected from PFWH6_0117; PFL_3193; CHMP4B; hypothetical protein [*Porphyromonas somerae*] Peptidase family C39 mostly contains bacteriocin-processing endopeptidases from bacteria; H1C1; MVAC_06252; RPS2; tpiA; Rv2563; Rv0410C; MRGA423_16320; Rv0881; PEX10; CysU; and hddA. In particular embodiments, the additional marker includes PFWH6_0117. In particular embodiments, the additional marker includes PFL_3193. In particular embodiments, the additional marker includes CHMP4B. In particular embodiments, the additional marker includes hypothetical protein Peptidase family C39 mostly contains bacteriocin-processing endopeptidases from bacteria. In particular embodiments, the additional marker includes H1C1. In particular embodiments, the additional marker includes MVAC_06252. In particular embodiments, the additional marker includes RPS2. In particular embodiments, the additional marker includes tpiA. In particular embodiments, the additional marker includes Rv2563. In particular embodiments, the additional marker includes Rv0410C. In particular embodiments, the additional marker includes MRGA423_16320. In particular embodiments, the additional marker includes Rv0881. In particular embodiments, the additional marker includes PEX10. In particular embodiments, the additional marker includes CysU. In particular embodiments, the additional marker includes hddA.

The systems and methods disclosed herein also allow distinguishing sarcoidosis from tuberculosis in a subject by assaying a sample obtained from a subject for the up- or down-regulation of one or more markers that distinguish sarcoidosis from tuberculosis. The markers include: Ferredoxin (*Mycobacterium tuberculosis*) (Fed A); WDFY3 protein (Homosapiens) (WDFY3); Membrane protein (*Mycobacterium tuberculosis*) (MFS); Leucine rich PPR-motif containing protein (Homosapiens) (LRPPRC); HLA-DR alpha (Homosapiens) (HLA-DR); Transketolase (*Mycobacterium tuberculosis*) (TKT); Dihydroxy acid dehydratase (*Mycobacterium tuberculosis*) (Rv0189C); Chain A *Mycobacterium tuberculosis* (BfrA); Disabled homolog 2 isoform 2 (Homosapiens) (DAB2); and Transcription elongation factor B polypeptide 2 isoform (Homosapiens) (TCEB2).

In particular embodiments, the systems and methods distinguish sarcoidosis from tuberculosis in a subject by assaying a sample obtained from a subject for the up- or down-regulation of two or more; three or more; four or more; five or more; six or more; seven or more; eight or more; nine or more or ten or more markers that distinguish sarcoidosis from tuberculosis disclosed herein. In further embodiments, the systems and methods distinguish sarcoidosis from tuberculosis by assaying a sample obtained from a subject for the up- or down-regulation of two; three; four; five; six; seven; eight; nine or ten markers associated with sarcoidosis disclosed herein.

In one embodiment, the markers include (hereafter referred to by gene abbreviations for brevity) Fed A; WDFY3; MFS; LRPPRC; HLA-DR; TKT; Rv0189C; BfrA; DAB2; and TCEB2. In another embodiment, the markers include HLA-DR; MFS; DAB2; BfrA; and WDFY3. In another embodiment, the markers include HLA-DR; MFS; DAB2; BfrA; or WDFY3. In another embodiment, the markers include HLA-DR; MFS; and DAB2. In another embodiment, the markers include HLA-DR; MFS; or DAB2.

In other embodiments, the markers include Fed A in combination with two, three, four, five, six, seven, eight or nine markers selected from: WDFY3; MFS; LRPPRC; HLA-DR; TKT; Rv0189C; BfrA; DAB2; and TCEB2.

In other embodiments, the markers include WDFY3 in combination with two, three, four, five, six, seven, eight or nine markers selected from: Fed A; MFS; LRPPRC; HLA-DR; TKT; Rv0189C; BfrA; DAB2; and TCEB2.

In other embodiments, the markers include MFS in combination with two, three, four, five, six, seven, eight or nine markers selected from: Fed A; WDFY3; LRPPRC; HLA-DR; TKT; Rv0189C; BfrA; DAB2; and TCEB2.

In other embodiments, the markers include LRPPRC in combination with two, three, four, five, six, seven, eight or nine markers selected from: Fed A; WDFY3; MFS; HLA-DR; TKT; Rv0189C; BfrA; DAB2; and TCEB2.

In other embodiments, the markers include HLA-DR in combination with two, three, four, five, six, seven, eight or nine markers selected from: Fed A; WDFY3; MFS; LRPPRC; TKT; Rv0189C; BfrA; DAB2; and TCEB2.

In other embodiments, the markers include TKT in combination with two, three, four, five, six, seven, eight or nine markers selected from: Fed A; WDFY3; MFS; LRPPRC; HLA-DR; Rv0189C; BfrA; DAB2; and TCEB2.

In other embodiments, the markers include Rv0189C in combination with two, three, four, five, six, seven, eight or nine markers selected from: Fed A; WDFY3; MFS; LRPPRC; HLA-DR; TKT; BfrA; DAB2; and TCEB2.

In other embodiments, the markers include BfrA in combination with two, three, four, five, six, seven, eight or nine markers selected from: Fed A; WDFY3; MFS; LRPPRC; HLA-DR; TKT; Rv0189C; DAB2; and TCEB2.

In other embodiments, the markers include DAB2 in combination with two, three, four, five, six, seven, eight or nine markers selected from: Fed A; WDFY3; MFS; LRPPRC; HLA-DR; TKT; Rv0189C; BfrA; and TCEB2.

In other embodiments, the markers include TCEB2 in combination with two, three, four, five, six, seven, eight or nine markers selected from: Fed A; WDFY3; MFS; LRP-PRC; HLA-DR; TKT; Rv0189C; BfrA; and DAB2.

In other embodiments, the markers exclude a marker selected from Fed A; WDFY3; MFS; LRPPRC; HLA-DR; TKT; Rv0189C; BfrA; DAB2; and TCEB2. In other embodiments, the markers exclude Fed A. In other embodiments, the markers exclude WDFY3. In other embodiments, the markers exclude MFS. In other embodiments, the markers exclude LRPPRC. In other embodiments, the markers exclude HLA-DR. In other embodiments, the markers exclude TKT. In other embodiments, the markers exclude Rv0189C. In other embodiments, the markers exclude BfrA. In other embodiments, the markers exclude DAB2. In other embodiments, the markers exclude TCEB2.

"Up-regulation" or "up-regulated" means an increase in the presence of a protein and/or an increase in the expression of its gene. "Down-regulation" or "down-regulated" means a decrease in the presence of a protein and/or a decrease in the expression of its gene. "Its gene" in reference to a particular protein refers to a nucleic acid sequence (used interchangeably with polynucleotide or nucleotide sequence) that encodes the particular protein. This definition also includes various sequence polymorphisms, mutations, and/or sequence variants wherein such alterations do not substantially affect the identity or function of the particular protein. For example, in a sequence identity analysis, the test protein would share at least 80% sequence identity; at least 81% sequence identity; at least 82% sequence identity; at least 83% sequence identity; at least 84% sequence identity; at least 85% sequence identity; at least 86% sequence identity; at least 87% sequence identity; at least 88% sequence identity; at least 89% sequence identity; at least 90% sequence identity; at least 91% sequence identity; at least 92% sequence identity; at least 93% sequence identity; at least 94% sequence identity; at least 95% sequence identity; at least 96% sequence identity; at least 97% sequence identity; at least 98% sequence identity or at least 99% sequence identity with the particular protein.

"% sequence identity" refers to a relationship between two or more sequences, as determined by comparing the sequences. In the art, "identity" also means the degree of sequence relatedness between protein (or nucleic acid) sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASER-GENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" mean any set of values or parameters which originally load with the software when first initialized.

The function of a protein can be assayed by a relevant activity assay. Function is not substantially affected if there is no statistically significant difference in activity between the particular protein and the test protein. Exemplary activity assays include binding assays, or, if the protein is an enzyme, enzyme activity assays including, for example, protease assays, kinase assays, phosphatase assays, reductase assays, etc. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

The term "gene" can include not only coding sequences but also regulatory regions such as promoters, enhancers, and termination regions. The term further can include all introns and other DNA sequences spliced from the mRNA transcript, along with variants resulting from alternative splice sites. Gene sequences encoding the particular protein can be DNA or RNA that directs the expression of the particular protein. These nucleic acid sequences may be a DNA strand sequence that is transcribed into RNA or an RNA sequence that is translated into the particular protein. The nucleic acid sequences include both the full-length nucleic acid sequences as well as non-full-length sequences derived from the full-length protein. The sequences can also include degenerate codons of the native sequence. Portions of complete gene sequences are referenced throughout the disclosure as is understood by one of ordinary skill in the art.

Up- or down-regulation of the markers, as indicated elsewhere herein for particular markers can be assessed by comparing a value to a relevant reference level. For example, the quantity of one or more markers can be indicated as a value. The value can be one or more numerical values resulting from the assaying of a sample, and can be derived, e.g., by measuring level(s) of the marker(s) in the sample by an assay performed in a laboratory, or from a dataset obtained from a provider such as a laboratory, or from a dataset stored on a server. The markers disclosed herein can be a protein marker or a nucleic acid marker (gene encoding the protein marker).

In the broadest sense, the value may be qualitative or quantitative. As such, where detection is qualitative, the systems and methods provide a reading or evaluation, e.g., assessment, of whether or not the marker is present in the sample being assayed. In yet other embodiments, the systems and methods provide a quantitative detection of whether the marker is present in the sample being assayed, i.e., an evaluation or assessment of the actual amount or relative abundance of the marker in the sample being assayed. In such embodiments, the quantitative detection may be absolute or, if the method is a method of detecting two or more different markers in a sample, relative. As such, the term "quantifying" when used in the context of quantifying a marker in a sample can refer to absolute or to relative quantification. Absolute quantification can be accomplished by inclusion of known concentration(s) of one or more control markers and referencing, e.g., normalizing, the detected level of the marker with the known control markers (e.g., through generation of a standard curve). Alternatively, relative quantification can be accomplished by comparison of detected levels or amounts between two or more different markers to provide a relative quantification of each of the two or more markers, e.g., relative to each other. The actual measurement of values of the markers can be determined at the protein or nucleic acid level using any method known in the art. In some embodiments, a marker is detected by contacting a sample with reagents (e.g., antibodies or nucleic acid primers), generating complexes of reagent and marker(s), and detecting the complexes.

The reagent can include a probe. A probe is a molecule that binds a target, either directly or indirectly. The target can be a marker, a fragment of the marker, or any molecule that is to be detected. In embodiments, the probe includes a nucleic acid or a protein. As an example, a protein probe can be an antibody. An antibody can be a whole antibody or a fragment of an antibody. A probe can be labeled with a detectable label. Examples of detectable labels include fluorescers, chemiluminescers, dyes, enzymes, enzyme substrates, enzyme cofactors, enzyme inhibitors, enzyme subunits, metal ions, and radioactive isotopes.

"Protein" detection includes detection of full-length proteins, mature proteins, pre-proteins, polypeptides, isoforms, mutations, post-translationally modified proteins and variants thereof, and can be detected in any suitable manner.

Those skilled in the art will be familiar with numerous specific immunoassay formats and variations thereof which can be useful for carrying out the methods disclosed herein. See, e.g., E. Maggio, Enzyme-Immunoassay (1980), CRC Press, Inc., Boca Raton, Fla.; and U.S. Pat. Nos. 4,727,022; 4,659,678; 4,376,110; 4,275,149; 4,233,402; and 4,230,797.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies can be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Examples of suitable immunoassays include immunoblotting, immunoprecipitation, immunofluorescence, chemiluminescence, electro-chemiluminescence (ECL), and/or enzyme-linked immunoassays (ELISA).

Antibodies may also be useful for detecting post-translational modifications of markers. Examples of post-translational modifications include tyrosine phosphorylation, threonine phosphorylation, serine phosphorylation, citrullination and glycosylation (e.g., O-GlcNAc). Such antibodies specifically detect the phosphorylated amino acids in marker proteins of interest. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., Proteomics 2002, 2(10):1445-1451.

Up- or down-regulation of genes also can be detected using, for example, cDNA arrays, cDNA fragment fingerprinting, cDNA sequencing, clone hybridization, differential display, differential screening, FRET detection, liquid microarrays, PCR, RT-PCR, quantitative real-time RT-PCR analysis with TaqMan assays, molecular beacons, microelectric arrays, oligonucleotide arrays, polynucleotide arrays, serial analysis of gene expression (SAGE), and/or subtractive hybridization.

As an example, Northern hybridization analysis using probes which specifically recognize one or more marker sequences can be used to determine gene expression. Alternatively, expression can be measured using RT-PCR; e.g., polynucleotide primers specific for the differentially expressed marker mRNA sequences reverse-transcribe the mRNA into DNA, which is then amplified in PCR and can be visualized and quantified. Marker RNA can also be quantified using, for example, other target amplification methods, such as transcription mediated amplification (TMA), strand displacement amplification (SDA), and nucleic acid sequence based amplification (NASBA), or signal amplification methods (e.g., bDNA), and the like. Ribonuclease protection assays can also be used, using probes that specifically recognize one or more marker mRNA sequences, to determine gene expression.

Further hybridization technologies that may be used are described in, for example, U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; and 5,800,992 as well as WO 95/21265; WO 96/31622; WO 97/10365; WO 97/27317; EP 373 203; and EP 785 280.

Proteins and nucleic acids can be linked to chips, such as microarray chips. See, for example, U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138. Microarray refers to a solid carrier or support that has a plurality of molecules bound to its surface at defined locations. The solid carrier or support can be made of any material. As an example, the material can be hard, such as metal, glass, plastic, silicon, ceramics, and textured and porous materials; or soft materials, such as gels, rubbers, polymers, and other non-rigid materials. The material can also be nylon membranes, epoxy-glass and borofluorate-glass, The solid carrier or support can be flat, but need not be and can include any type of shape such as spherical shapes (e.g., beads or microspheres). The solid carrier or support can have a flat surface as in slides and micro-titer plates having one or more wells.

Binding to proteins or nucleic acids on microarrays can be detected by scanning the microarray with a variety of laser or CCD-based scanners, and extracting features with software packages, for example, Imagene (Biodiscovery, Hawthorne, Calif.), Feature Extraction Software (Agilent), Scanalyze (Eisen, M. 1999. SCANALYZE User Manual; Stanford Univ., Stanford, Calif. Ver 2.32.), or GenePix (Axon Instruments).

Embodiments disclosed herein can be used with high throughput screening (HTS). Typically, HTS refers to a format that performs at least about 100 assays, at least about 500 assays, at least about 1000 assays, at least about 5000 assays, at least about 10,000 assays, or more per day. When enumerating assays, either the number of samples or the number of protein or nucleic acid markers assayed can be considered.

Generally HTS methods involve a logical or physical array of either the subject samples, or the protein or nucleic acid markers, or both. Appropriate array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384, or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis.

HTS assays and screening systems are commercially available from, for example, Zymark Corp. (Hopkinton, Mass.); Air Technical Industries (Mentor, Ohio); Beckman Instruments, Inc. (Fullerton, Calif.); Precision Systems, Inc. (Natick, Mass.), etc. These systems typically automate entire procedures including all sample and reagent pipetting, liquid dispensing, timed incubations, and final readings of the microplate in detector(s) appropriate for the assay. These configurable systems provide HTS as well as a high degree of flexibility and customization. The manufacturers of such systems provide detailed protocols for the various methods of HTS.

As stated previously, obtained marker values can be compared to a reference level. Reference levels can be obtained from one or more relevant datasets. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual datapoints; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a population. A "population" is any grouping of subjects or samples of like specified characteristics. The grouping could be according to, for example, clinical parameters, clinical assessments, therapeutic regimens, disease status, severity of condition, etc.

Subjects include humans, veterinary animals (dogs, cats, reptiles, birds, hamsters, etc.) livestock (horses, cattle, goats, pigs, chickens, etc.), research animals (monkeys, rats, mice, fish, etc.) and other animals, such as zoo animals (e.g., bears, giraffe, elephant, lemurs).

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered significant (not random chance) at a p-value less than or equal to 0.05.

In one embodiment, values obtained about the markers and/or other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained value with a reference level, a linear algorithm, a quadratic algorithm, a decision tree algorithm, or a voting algorithm. The analytic process may set a threshold for determining the probability that a sample belongs to a given class. The probability preferably is at least at least 60%, at least 70%, at least 80%, at least 90%, at least 95% or higher.

In embodiments, the relevant reference level for a particular marker is obtained based on the particular marker in control subjects. Control subjects are those that are healthy and do not have sarcoidosis or tuberculosis. As an example, the relevant reference level can be the quantity of the particular marker in the control subjects.

In additional embodiments when more than one marker is assayed, values of the detected markers can be calculated into a score. Each value can be weighted evenly within an algorithm generating a score, or the values for particular markers can be weighted more heavily in reaching the score. For example, markers with higher sensitivity and/or specificity scores could be weighted more heavily than markers with lower sensitivity and/or specificity scores. For example, marker values for diagnosing sarcoidosis may be weighted as follows (from highest weight to lowest weight): CCL21; APBB1; Metap1; SH3YL; CLI_3190; PC4; DNAJC1; TNFRSF21; CD14; FGFBP-2. Markers may also be grouped into classes, and each class given a weighted score. For example, marker values for diagnosing sarcoidosis may be grouped into classes and weighted as follows (from highest weight to lowest weight): Class 1: CCL21 and APBB1; Class 2: Metap1 and SH3YL; Class 3: CLI_3190 and PC4; Class 4: DNAJC1 and TNFRSF21; and Class 5: CD14 and FGFBP-2. As another example, marker values for diagnosing sarcoidosis may be grouped into classes and weighted as follows (from highest weight to lowest weight): Class 1: CCL21; APBB1; Metap1 and SH3YL; Class 2: CLI_3190; PC4; DNAJC1 and TNFRSF21; and Class 3: CD14 and FGFBP-2.

In particular embodiments, marker values for distinguishing sarcoidosis from tuberculosis may be weighted as follows (from highest weight to lowest weight): HLA-DR; MF5; BfrA; DAB2; WDFY3; FedA; TCEB2; Rv0189C; LRPPRC; TKT. Markers may also be grouped into classes, and each class given a weighted score. For example, marker values for diagnosing sarcoidosis may be grouped into classes and weighted as follows (from highest weight to lowest weight): Class 1: HLA-DR and MF5; Class 2: BfrA and DAB2; Class 3: WDFY3 and FedA; Class 4: TCEB2 and Rv0189C; and Class 5: LRPPRC and TKT. As another example, marker values for diagnosing sarcoidosis may be grouped into classes and weighted as follows (from highest weight to lowest weight): Class 1: HLA-DR; MF5; BfrA; and DAB2; Class 2: WDFY3; FedA; TCEB2; and Rv0189C; and Class 3: LRPPRC; and TKT.

Any marker or class of markers can be excluded from a particular value calculation. For example, in particular embodiments, Class 5 is excluded. In particular embodiments, Class 4 is excluded. In particular embodiments, Class 3 is excluded. In particular embodiments, Class 2 is excluded. In particular embodiments, Class 1 is excluded. In further embodiments, groups of classes can be excluded, for example, Classes 5 and 4; 5 and 3; 5 and 2; 4 and 3; 4 and 2; 3 and 2; etc.

Particular embodiments disclosed herein include obtaining a sample from a subject suspected of having sarcoidosis;

assaying the sample for up- or down-regulation of one or more markers disclosed herein; determining one or more marker values based on the assaying; comparing the one or more marker values to a reference level; diagnosing sarcoidosis in the subject according to the up- or down regulation of a marker, as described elsewhere herein.

Particular embodiments also include distinguishing sarcoidosis from tuberculosis in a subject by obtaining a sample from a subject suspected of having sarcoidosis; assaying the sample for up- or down-regulation of one or more markers disclosed herein; determining one or more marker values based on the assaying; comparing the one or more marker values to a reference level; diagnosing sarcoidosis or tuberculosis in the subject according to the up- or down regulation of a marker, as described elsewhere herein.

The sample can be any appropriate biological sample obtained from the subject, such as a blood sample, a serum sample, a saliva sample, a urine sample, bronchoalveolar larvage sample, etc. The sample also can be obtained from a biopsy of an affected tissue or organ, such as a lung biopsy, or lymph gland biopsy. The sample can include cells of affected tissue or organ.

A diagnosis according to the systems and methods disclosed herein can direct a treatment regimen. For example, a sarcoidosis diagnosis can direct treatment with a sarcoidosis treatment (e.g., lifestyle and behavioral interventions; corticosteroids; methotrexate or azathioprine; hydroxychloroquine or chloroquine; cyclophosphamide or chlorambucil; pentoxifylline and thalidomide; infliximab or adalimumab; colchicine; various nonsteroidal anti-inflammatory drugs (NSAIDs, e.g., ibuprofen or aspirin); organ transplantation). A tuberculosis diagnosis can direct treatment with a tuberculosis treatment (e.g., isoniazid (INH); rifampin (RIF); ethambutol (EMB); pyrazinamide (PZA)). A healthy diagnosis can direct further medical analysis if the subject's symptoms suggest further analysis is warranted. Administered treatments will be delivered in therapeutically effective amounts leading to an improvement or resolution of the treated condition, as assessed by a practicing physician, veterinarian or researcher.

The systems and methods disclosed herein include kits. Disclosed kits include materials and reagents necessary to assay a sample obtained from a subject for one or more markers disclosed herein. The materials and reagents can include those necessary to assay the markers disclosed herein according to any method described herein and/or known to one of ordinary skill in the art.

Particular embodiments include materials and reagents necessary to assay for up- or down-regulation of a marker protein in a sample. In particular embodiments, the kits include antibodies to marker proteins and/or can also include aptamers, epitopes or mimotopes. Other embodiments additionally or alternatively include oligonucleotides that specifically assay for one or more marker nucleic acids based on homology and/or complementarity with marker nucleic acids. The oligonucleotide sequences may correspond to fragments of the marker nucleic acids. For example, the oligonucleotides can be more than 200, 175, 150, 100, 50, 25, 10, or fewer than 10 nucleotides in length. Collectively, any molecule (e.g., antibody, aptamer, epitope, mimotope, oligonucleotide) that forms a complex with a marker is referred to as a marker binding agent herein.

Embodiments of kits can contain in separate containers marker binding agents either bound to a matrix, or packaged separately with reagents for binding to a matrix. In particular embodiments, the matrix is, for example, a porous strip. In some embodiments, measurement or detection regions of the porous strip can include a plurality of sites containing marker binding agents. In some embodiments, the porous strip can also contain sites for negative and/or positive controls. Alternatively, control sites can be located on a separate strip from the porous strip. Optionally, the different detection sites can contain different amounts of marker binding agents, e.g., a higher amount in the first detection site and lesser amounts in subsequent sites. Upon the addition of test sample, the number of sites displaying a detectable signal provides a quantitative indication of the amount of marker present in the sample. The detection sites can be configured in any suitably detectable shape and can be, e.g., in the shape of a bar or dot spanning the width (or a portion thereof) of a porous strip.

In some embodiments the matrix can be a solid substrate, such as a "chip." See, e.g., U.S. Pat. No. 5,744,305. In some embodiments the matrix can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Additional embodiments can include control formulations (positive and/or negative), and/or one or more detectable labels, such as fluorescein, green fluorescent protein, rhodamine, cyanine dyes, Alexa dyes, luciferase, and radiolabels, among others. Instructions for carrying out the assay, including, optionally, instructions for generating a score, can be included in the kit; e.g., written, tape, VCR, or CD-ROM.

In particular embodiments, the kits include materials and reagents necessary to conduct and immunoassay (e.g., ELISA). In particular embodiments, the kits include materials and reagents necessary to conduct hybridization assays (e.g., PCR). In particular embodiments, materials and reagents expressly exclude equipment (e.g., plate readers). In particular embodiments, kits can exclude materials and reagents commonly found in laboratory settings (pipettes; test tubes; distilled H2O).

Numerous protein and gene sequence markers are disclosed herein. The disclosure is not limited to the particularly disclosed protein and gene sequences but instead also encompasses sequences including 80% sequence identity; 81% sequence identity; 82% sequence identity; 83% sequence identity; 84% sequence identity; 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity or 99% sequence identity.

When a protein sequence is provided, its gene sequences can be derived by one of ordinary skill in the art by, for example, consulting publicly available databases. In addition to the sequence identity parameters provided above, gene sequences that hybridize to derived sequences under high stringency conditions can also be included within the scope of the current disclosure. A gene or polynucleotide fragment "hybridizes" to another gene or polynucleotide fragment, such as a cDNA, genomic DNA, or RNA, when a single stranded form of the polynucleotide fragment anneals to the other polynucleotide fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Ed., Cold Spring Harbor Laboratory Press, Cold Spring Harbor (1989), particularly Chapter 11 and Table 11.1 therein (incorporated by reference herein for its teachings regarding the same). The conditions of temperature and ionic strength determine the "stringency" of the hybridization. Stringency conditions can be adjusted to screen for moderately similar fragments (such as homologous sequences from distantly related organisms) to highly similar fragments (such as genes that duplicate functional enzymes from closely related organisms). Post-hybridization washes determine stringency conditions. One set of hybridization conditions to demonstrate that sequences hybridize uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Stringent conditions use higher temperatures in which the washes are identical to those above except for the temperature of the final two 30 min washes in 0.2×SSC, 0.5% SDS is increased to 60° C. Highly stringent conditions use two final washes in 0.1SSC, 0.1% SDS at 65° C. Those of ordinary skill in the art will recognize that these temperature and wash solution salt concentrations may need to be adjusted as necessary according to factors such as the length of the hybridizing sequences.

Also disclosed herein is a cDNA library including mRNA isolated from (i) bronchoalveolar cells (BAL) of sarcoidosis patients; and (ii) white blood cells obtained from sarcoidosis patients. In further embodiments, the cDNA library further includes mRNA isolated from (iii) human splenic monocytes; and/or (iv) embryonic lung fibroblasts. The cDNA library can be screened for markers associated with sarcoidosis or related disorders. The cDNA library can be a phage display library, a ribosome display library, or a nucleic acid display library. In particular embodiments, the cDNA library is a T7 phage display library. In particular embodiments, the cDNA library should be biopanned to negatively select and/or enrich for detection markers of interest. For example, biopanning with samples from control subjects can remove potential hits that are non-specific to the condition of interest, resulting in negative selection. Biopanning with samples from subjects of interest (e.g., subjects having a condition of interest) selects potential hits that are specific to the condition of interest, resulting in enrichment of the cDNA library for hits of potential interest. The systems and methods disclosed herein include biopanning a cDNA library including mRNA isolated from (i) bronchoalveolar cells (BAL) of sarcoidosis patients; (ii) white blood cells obtained from sarcoidosis patients; (iii) human splenic monocytes; and (iv) embryonic lung fibroblasts to negatively select for and/or enrich the library for hits of interest.

In embodiments, the cDNA library is differentially biopanned to identify markers for sarcoidosis. As described above, differential biopanning involves biopanning by negative selection using sera from control subjects to remove non-specific IgG, followed by biopanning by positive enrichment using sera from sarcoidosis patients.

Additional embodiments include adhering cDNA expression products from a negatively selected and enriched cDNA library to a microarray. Additional embodiments include exposing the microarray to samples from subjects of interest and control samples. Additional embodiments include detecting cDNA expression products bound by molecules in samples from the subjects of interest. Additional embodiments include performing data analysis to identify molecules that bind cDNA expression products as markers of a condition of interest.

One embodiment includes detecting sarcoidosis or tuberculosis antigens by: (a) preparing a phage display library of sarcoidosis or tuberculosis antigens from cells of one or more subjects with sarcoidosis; (b) enriching the phage display library for sarcoidosis or tuberculosis antigens by biopanning; (c) selecting clones for amplification; (d) testing amplified clones for binding to antibodies in sera of sarcoidosis subjects; and (e) sequencing bound clones.

Another embodiment includes a library and method to identify sarcoidosis markers. One embodiment includes identifying proteins that bind to expression products of phage display clones derived from a library including mRNA isolated from (i) bronchoalveolar cells (BAL) of sarcoidosis patients; (ii) white blood cells obtained from sarcoidosis patients; (iii) human splenic monocytes; and/or (iv) embryonic lung fibroblasts. Another embodiment includes identifying proteins that bind to expression products of phage display clones derived from a library including mRNA isolated from (i) bronchoalveolar cells (BAL) of sarcoidosis patients; (ii) white blood cells obtained from sarcoidosis patients; (iii) human splenic monocytes; and (iv) embryonic lung fibroblasts. Following binding, identified proteins can be characterized and, in particular embodiments, synthesized.

These embodiments can be used to identify additional markers to diagnose systemic sarcoidosis, pulmonary sarcoidosis, cutaneous sarcoidosis, Lofgren's syndrome, neurosarcoidosis, cardiac sarcoidosis, ocular sarcoidosis, hepatic sarcoidosis, musculoskeletal sarcoidosis, renal sarcoidosis, or sarcoidosis with the involvement of other organs or tissues.

In embodiments, diagnosis of sarcoidosis may be achieved in accordance with the previously disclosed methods through the use of a computing device to provide for a quicker, more reliable, and less labor intensive diagnosis.

Figure 10:
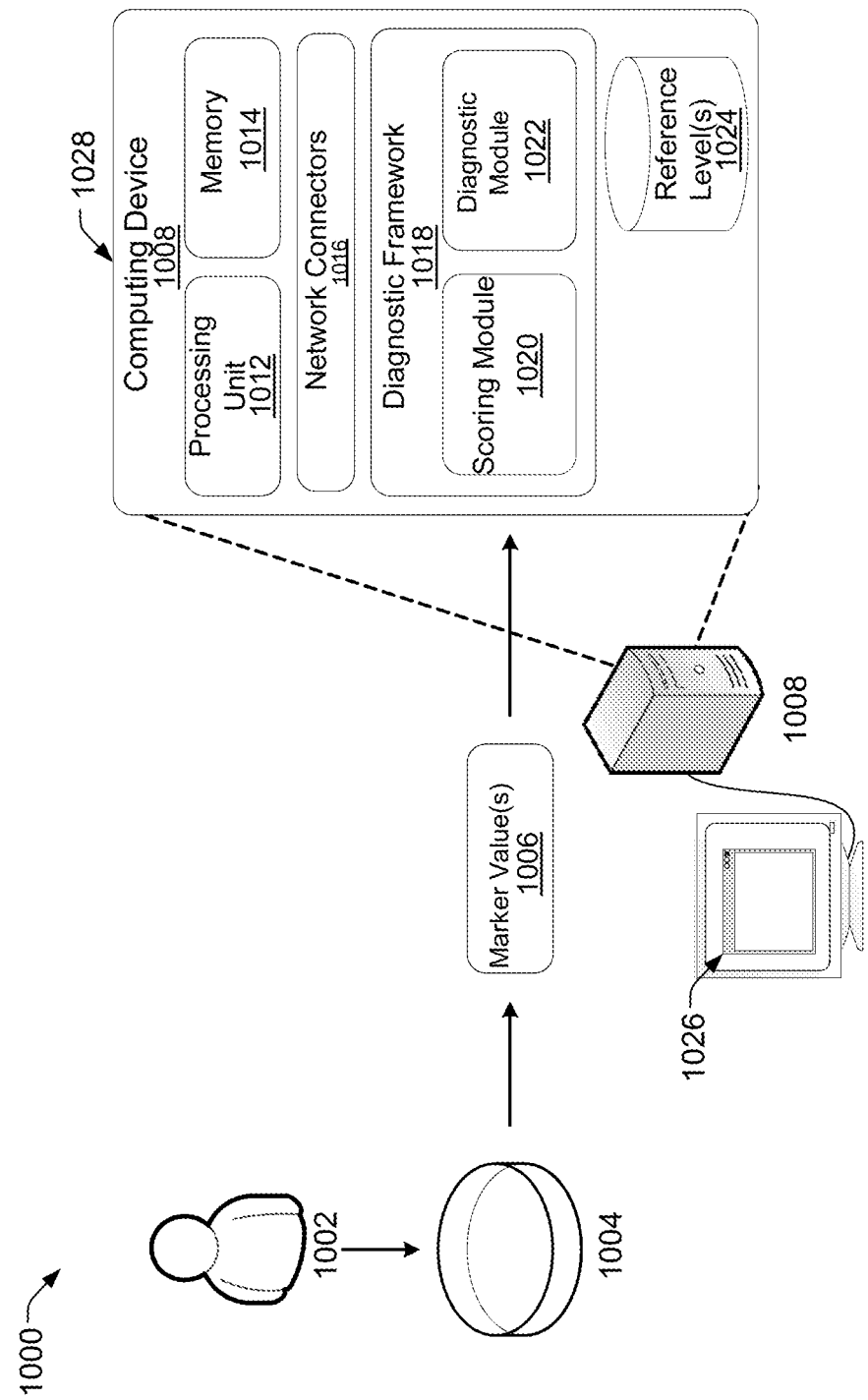
FIG. 10 shows an illustrative schematic for using computational tools as part of a process for diagnosing sarcoidosis, including an illustrative diagram of a computing device implementing the diagnostic framework.

FIG. 10 shows an illustrative schematic 1000 for diagnosing sarcoidosis in a subject 1002 on a computing device 1008, including an illustrative diagram 1028 of a computing device 1008 implementing the diagnostic framework 1018. Sample biological material 1004 is collected from the subject 1002. That sample 1004 may be assayed for the presence of one or more markers. An indication of the up- or down-regulation of the markers is reflected by one or more marker values 1006 generated after assaying and analyzing the sample 1004. A computing device 1008 implementing the diagnostic framework 1018 will analyze and diagnose the subject 1002 as healthy, having sarcoidosis, or in some embodiments, having tuberculosis. The diagnosis is published to a user via a graphical user interface 1026.

In embodiments, to enhance security, subject privacy, and compliance with government regulations, subject data like the subject's marker values 1006 may be deleted after it is used to generate a computer assisted diagnosis. Thus, the sample information will no longer exist as standalone information on the one or more computing devices 1028 implementing the diagnostic framework 1018. Thus, the only subject data available to the computing device 1008 will be integrated into the diagnosis provided by the one or more computing devices.

FIG. 10 includes an illustrative diagram 1028 of the computing device 1008. The computing device 1008 may contain one or more processing unit(s) 1012 and memory 1014, both of which may be distributed across one or more physical or logical locations. The processing unit(s) 1012 may include any combination of central processing units (CPUs), graphical processing units (GPUs), single core processors, multi-core processors, application-specific integrated circuits (ASICs), programmable circuits such as Field Programmable Gate Arrays (FPGA), and the like. One or more of the processing unit(s) 1012 may be implemented in software and/or firmware in addition to hardware implementations. Software or firmware implementations of the processing unit(s) 1012 may include computer- or machine-executable instructions written in any suitable programming language to perform the various functions described. Software implementations of the processing unit(s) 1012 may be stored in whole or part in the memory 1014.

Additionally, the functionality of the computing devices 1008 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Computing device 1008 may be connected to a network through one or more network connectors 1016 for receiving and sending information. The network may be implemented as any type of communications network such as a local area network, a wide area network, a mesh network, and ad hoc network, a peer-to-peer network, the Internet, a cable network, a telephone network, and the like. In embodiments, the computing device 1008 have a direct connection to one or more other devices (e.g. devices that output subject 1002 information, like marker values 1006, in electrical or electronic form) without the presence of an intervening network. The direct connection may be implemented as a wired connection or a wireless connection. A wired connection may include one or more wires or cables physically connecting the computing device 1008 to another device. For example, the wired connection may be created by a headphone cable, a telephone cable, a SCSI cable, a USB cable, an Ethernet cable, or the like. The wireless connection may be created by radio frequency (e.g., any version of Bluetooth, ANT, Wi-Fi IEEE 802.11, etc.), infrared light, or the like.

The computing device 1008 may be a supercomputer, a network server, a desktop computer, a notebook computer, a collection of server computers such as a server farm, a cloud computing system that uses processing power, memory, and other hardware resources distributed across multiple geographic locations, or the like. The computing device 1008 may include one or more input/output components(s) such as a keyboard, a pointing device, a touchscreen, a microphone, a camera, a display, a speaker, a printer, and the like.

Memory 1014 of the computing device 1008 may include removable storage, non-removable storage, local storage, and/or remote storage to provide storage of computer-readable instructions, data structures, program modules, and other data. The memory 1014 may be implemented as computer-readable media. Computer-readable media includes non-volatile computer-readable storage media, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

The computing device 1008 includes multiple modules that may be implemented as instructions stored in the memory 1014 for execution by processing unit(s) 1012 and/or implemented, in whole or in part, by one or more hardware logic components or firmware. The diagnostic framework 1018 is contained within the computing device 1008 and may be implemented as instructions stored in the memory 1014 for execution by the processing unit(s) 1012, by hardware logic components, or both.

A scoring module 1012 obtains from an external source an indication of the expression of the tested markers in a sample 1004 as one or more marker value(s) 1006. The marker values 1006 can be obtained from a microarray or any machine connected to the computing device 1008 either directly or through the network connectors 1016. The marker values 1006 may also be previously saved or stored on a separate computing device or computer-readable media prior to being transferred to the scoring module 1020. The marker values 1008 may also be inputted directly by a user, including a physician or laboratory technician, through any appropriate I/O method. Exemplary I/O methods include any methods making use of the previously mentioned input/output components such as a keyboard, camera, microphone, touchscreen, or scanner.

The scoring module 1020 also obtains a reference level corresponding to the one or more marker values 1006. As with the marker values 1006, the reference levels can be calculated, as previously explained, and stored in a reference level database 1024, on the computing device 1008. Those having skill in the art will appreciate, however, that the one or more reference levels 1024 may, in other embodiments, be obtained either directly or through the network connectors 1016 from one or more separate computing devices, machines, or computer readable media. The reference levels may also be directly inputted by the user.

The scoring module 1020 may partially process, normalize, rewrite, anonymize, or otherwise modify the marker values 1006 or reference levels 1024. The scoring module 1020 will generate a score based at least in part on the one or more marker values 1006. In some embodiments this score is equivalent to the one or more marker values. In other embodiments, the score will be generated based at least in the part on the marker values 1006 and a weight associated with each corresponding marker. For example, markers with higher sensitivity, specificity, or both could be weighted more heavily than markers with lower sensitivity or specificity. Alternative scores may be generated based on any other previously discussed analytic process.

The scoring module 1020 provides the generated score to a diagnostic module 1022. The diagnostic module compares the score to the reference level and diagnoses the subject 1002 based on a result of the comparison as having sarcoidosis, not having sarcoidosis, or in some embodiments, having tuberculosis. The diagnosis is published to the user via a graphical user interface 1026.

Illustrative Process: For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

FIG. 11 shows an illustrative process 1100 for diagnosing sarcoidosis.

At 1102, one or more reference levels are received, as well as an indication of the expression of relevant markers in a sample. The indication of the one or more marker values may be received from a clinician who assayed the sample for the value, or they may be received from a database where the values from a previously performed assay have been stored.

At 1104, a score is generated at least partly based on the marker value. The score may be the same as the marker value, or it may be additionally based on a weight corresponding to each tested marker, or based in part on any other previously disclosed analytic process. Note that there may be a score for each marker, or there may be a single score based on an aggregation of data related to multiple marker values.

At 1106, the score is compared to one or more reference levels.

At 1108, a subject is diagnosed based on a result of the comparison 1106 as being healthy, having sarcoidosis, or in some embodiments, having tuberculosis.

In embodiments, the subjects diagnosed with sarcoidosis or tuberculosis using the methods disclosed herein can be effectively treated with the appropriate therapy. As an example, treating subjects with sarcoidosis includes delivering therapeutically effective amounts of an appropriate drug to alleviate one or more symptoms of sarcoidosis or tuberculosis.

Particular embodiments include:

Embodiment 1. A method of diagnosing sarcoidosis in a subject including assaying a sample derived from a subject for the presence of one or more markers selected from Small inducible cytokine A21 precursor (CCL21); Methionine aminopeptidase 1 (Metap1); Activated RNA polymerase II transcription cofactor variant 4 (PC4); RNA methyltransferase (CLI_3190); Tumor necrosis factor receptor superfamily member 21 precursor (TNFRSF21); Monocyte differentiation antigen CD14 (CD14); DnaJ (Hsp40) homolog subfamily C member 1 precursor (DNAJC1); Amyloid β A4 precursor protein-binding family B member 1-interacting protein (APBB1); Fibroblast growth factor binding protein 2 precursor (FGFBP-2); or SH3 domain-containing YSC84 like protein 1 (SH3YL1); and diagnosing the subject as healthy or having sarcoidosis based on the up- or down-regulation of the one or more markers, as compared to a reference level for each marker.

2. A method of embodiment 1 including assaying the sample for the presence of CCL21; Metap1; CLI_3190; APBB1; and SH3YL1; and diagnosing the subject as healthy or having sarcoidosis based on the up- or down-regulation of the one or more markers.

3. A method of embodiment 1 including assaying the sample for the presence of CCL21; Metap1; PC4; CLI_3190; TNFRSF21; and APBB1; and diagnosing the subject as healthy or having sarcoidosis based on the up- or down-regulation of the one or more markers.

4. A method of embodiment 1 including assaying the sample for the presence of CCL21; PC4; CLI_3190; DNAJC1; APBB1; FGFBP-2; and SH3YL1; and diagnosing the subject as healthy or having sarcoidosis based on the up- or down-regulation of the one or more markers.

5. A method of embodiment 1 including assaying the sample for the presence of CCL21; Metap1; PC4; CLI_3190; TNFRSF21; CD14; DNAJC1; APBB1; FGFBP-2; and SH3YL1; and diagnosing the subject as healthy or having sarcoidosis based on the up- or down-regulation of the one or more markers.

6. A method of distinguishing sarcoidosis from tuberculosis in a subject including assaying a sample obtained from the subject for the presence of one or markers selected from Ferredoxin (Fed A); WDFY3 protein (WDFY3); Membrane protein (MFS); Leucine rich PPR-motif containing protein (LRPPRC); HLA-DR alpha (HLA-DR); Transketolase (TKT); Dihydroxy acid dehydratase (Rv0189C); Chain A *Mycobacterium tuberculosis* (BfrA); Disabled homolog 2 isoform 2 (DAB2); or Transcription elongation factor B polypeptide 2 isoform (Homosapiens) (TCEB2); and diagnosing the subject as healthy, having sarcoidosis or having tuberculosis based on the up- or down-regulation of the one or more markers as compared to a reference level for each marker.

7. A method of embodiment 6 including assaying the sample for the presence of Fed A; WDFY3; MFS; LRPPRC; HLA-DR; TKT; Rv0189C; BfrA; DAB2; and TCEB2; and diagnosing the subject as healthy, having sarcoidosis or having tuberculosis based on the up- or down-regulation of the one or more markers.

8. A method of embodiment 6 including assaying the sample for the presence of HLA-DR; MFS; DAB2; BfrA; and WDFY3; and diagnosing the subject as healthy, having sarcoidosis or having tuberculosis based on the up- or down-regulation of the one or more markers.

9. A method of embodiment 6 including assaying the sample for the presence of HLA-DR; MFS; and DAB2; and diagnosing the subject as healthy, having sarcoidosis or having tuberculosis based on the up- or down-regulation of the one or more markers.

10. A kit for diagnosing sarcoidosis in a subject wherein the kit includes a protein that binds CCL21; Metap1; PC4; CLI_3190; TNFRSF21; CD14; DNAJC1; APBB1; FGFBP-2; or SH3YL1; and a detectable label.

11. A kit according to embodiment 10 including one or more proteins that bind CCL21; Metap1; CLI_3190; APBB1; or SH3YL1; and a detectable label.

12. A kit according to embodiment 10 including one or more proteins that bind CCL21; Metap1; PC4; CLI_3190; TNFRSF21; or APBB1; and a detectable label.

13. A kit according to embodiment 10 including one or more proteins that bind CCL21, PC4; CLI_3190; DNAJC1; APBB1; FGFBP-2; or SH3YL1, and a detectable label.

14. A kit according to embodiment 10 including one or more proteins that bind CCL21; Metap1; PC4; CLI_3190; TNFRSF21; CD14; DNAJC1; APBB1; FGFBP-2; or SH3YL1; and a detectable label.

15. A kit for distinguishing sarcoidosis from tuberculosis in a subject wherein the kit includes a protein that binds Fed A; WDFY3; MFS; LRPPRC; HLA-DR; TKT; Rv0189C; BfrA; DAB2; or TCEB2; and a detectable label.

16. A kit according to embodiment 15 including one or more proteins that bind Fed A; WDFY3; MFS; LRPPRC; HLA-DR; TKT; Rv0189C; BfrA; DAB2; or TCEB2; and a detectable label.

17. A kit according to embodiment 15 including one or more proteins that bind HLA-DR; MFS; DAB2; BfrA; or WDFY3; and a detectable label.

18. A kit according to embodiment 15 including one or more proteins that bind HLA-DR; MFS; or DAB2; and a detectable label.

19. A kit according to any one of embodiments 10-18 wherein the proteins include antibodies, epitopes or mimotopes.

20 A kit for diagnosing sarcoidosis in a subject wherein the kit includes a nucleic acid that binds a gene encoding CCL21; Metap1; PC4; CLI_3190; TNFRSF21; CD14; DNAJC1; APBB1; FGFBP-2; or SH3YL1; and a detectable label.

21. A kit according to embodiment 20 including one or more nucleic acids that bind a gene encoding CCL21; Metap1; CLI_3190; APBB1; or SH3YL1; and a detectable label.

22. A kit according to embodiment 20 including one or more nucleic acids that bind a gene encoding CCL21; Metap1; PC4; CLI_3190; TNFRSF21; or APBB1; and a detectable label.

23. A kit according to embodiment 20 including one or more nucleic acids that bind a gene encoding CCL21, PC4; CLI_3190; DNAJC1; APBB1; FGFBP-2; or SH3YL1; and a detectable label.

24. A kit according to embodiment 20 including one or more nucleic acids that bind a gene encoding CCL21; Metap1; PC4; CLI_3190; TNFRSF21; CD14; DNAJC1; APBB1; FGFBP-2; or SH3YL1; and a detectable label.

25. A kit for distinguishing sarcoidosis from tuberculosis in a subject wherein the kit includes one or more nucleic acids that bind a gene encoding Fed A; WDFY3; MFS; LRPPRC; HLA-DR; TKT; Rv0189C; BfrA; DAB2; or TCEB2; and a detectable label.

26. A kit according to embodiment 25 including one or more nucleic acids that bind a gene encoding Fed A; WDFY3; MFS; LRPPRC; HLA-DR; TKT; Rv0189C; BfrA; DAB2; or TCEB2; and a detectable label.

27. A kit according to embodiment 25 including one or more nucleic acids that bind a gene encoding HLA-DR; MFS; DAB2; BfrA; or WDFY3; and a detectable label.

28. A kit according to embodiment 25 including one or more nucleic acids that bind a gene encoding HLA-DR; MFS; or DAB2; and a detectable label.

29. A kit according to any one of embodiments 10-28 wherein the detectable label is a radioactive isotope, enzyme, dye, fluorescent dye, magnetic bead, or biotin.

30. A kit according any one of claims 10-29 wherein the kit further includes reagents to perform an enzyme-linked immunosorbent assay (ELISA), a radioimmunoassay (RIA), a Western blot, an immunoprecipitation, an immunohistochemical staining, flow cytometry, fluorescence-activated cell sorting (FACS), an enzyme substrate color method, and/or an antigen-antibody agglutination.

31. A method of diagnosing sarcoidosis in a subject including obtaining a sample from a subject; assaying the sample for one or more markers selected from CCL21; Metap1; PC4; CLI_3190; TNFRSF21; CD14; DNAJC1; APBB1; FGFBP-2; or SH3YL1 obtaining a value based on the assay; comparing the value to a reference level; and diagnosing the subject as healthy or having sarcoidosis based on the up- or down-regulation of the one or more markers as demonstrated by the value and the reference level.

32. A method according to embodiment 31 including assaying the sample for one or more markers selected from CCL21; Metap1; CLI_3190; APBB1; or SH3YL1.

33. A method according to any one of embodiments 31 or 32 including assaying the sample for one or more markers selected from CCL21; Metap1; PC4; CLI_3190; TNFRSF21; or APBB1.

34. A method according to any one of embodiments 31-33 including assaying the sample for one or more markers selected from CCL21; PC4; CLI_3190; DNAJC1; APBB1; FGFBP-2; or SH3YL1.

35. A method according to any one of embodiments 31-34 including assaying the sample for one or more markers selected from CCL21; Metap1; PC4; CLI_3190; TNFRSF21; CD14; DNAJC1; APBB1; FGFBP-2; or SH3YL1

36. A method of distinguishing sarcoidosis from tuberculosis in a subject including:
obtaining a sample derived from the subject;
assaying the sample for one or more markers selected from Fed A; WDFY3; MFS; LRPPRC; HLA-DR; TKT; Rv0189C; BfrA; DAB2; or TCEB2;
obtaining a value based on the assay;
comparing the value to a reference level; and
diagnosing the subject as healthy, having sarcoidosis or having tuberculosis based on the up- or down-regulation of the one or more markers as demonstrated by the value and the reference level.

37. A method according to embodiment 36 including assaying the sample for one or more markers selected from Fed A; WDFY3; MFS; LRPPRC; HLA-DR; TKT; Rv0189C; BfrA; DAB2; or TCEB2.

38. A method according to embodiment 36 or 37 including assaying the sample for one or more markers selected from HLA-DR; MFS; DAB2; BfrA; or WDFY3.

39. A method according to any one of embodiments 36-38 including assaying the sample for one or more markers selected from HLA-DR alpha (HLA-DR); Membrane protein (MFS); or Disabled homolog 2 isoform 2 (DAB2).

40. A method according to any one of embodiments 31-39, wherein assaying the sample for one or more markers include contacting the sample with a probe including a detectable label, wherein the probe binds the marker.

41. A method of any one of embodiments 31-40, wherein obtaining a value based on the assay includes analyzing the binding of the probe to the marker in the sample.

42. A method of any one of embodiments 31-41, wherein analyzing the binding of the probe to the marker in the sample includes quantitating the amount of the marker in the sample.

43. A method of any one of embodiments 31-42, wherein the sample is a tissue sample, a cell sample, a whole blood sample, a serum sample, a plasma sample, a saliva sample, a sputum sample, or a urine sample.

44. A method of any one of embodiments 31-43 wherein the value is a score.

45. A method of any one of embodiments 31-44 wherein the score is a weighted score.

46. A cDNA library including mRNA isolated from (i) bronchoalveolar cells (BAL) of sarcoidosis patients; and (ii) white blood cells obtained from sarcoidosis patients.

47. A cDNA library of embodiment 46 further including mRNA isolated from (iii) human splenic monocytes; and/or (iv) embryonic lung fibroblasts.

48. A cDNA library of any one of embodiments 46 or 47 wherein the cDNA library is a phage display library.

49. A cDNA library of any one of embodiments 46-48 wherein the phage display library is a T7 phage display library.

50. A cDNA library of any one of embodiments 46-49 wherein cDNA from each cell type is linked to an identifying sequence or tag.

51. A cDNA library of any one of embodiments 46-50 wherein the identifying sequence or tag is a modified linker selected from ECOR1/HindIII; ALA; LEU; and THR.

52. A cDNA library of any one of embodiments 46-51 following biopanning.

53. A cDNA library of any one of embodiments 46-52 wherein the biopanning includes negative selection and/or enrichment.

54. A method of identifying markers to diagnose sarcoidosis including adhering cDNA expression products from a cDNA library of any one of embodiments 46-52 to a microarray; exposing the microarray to samples from sarcoidosis subjects and control subjects; detecting cDNA expression products bound by molecules in the samples from sarcoidosis subjects but not by samples from control subjects; performing data analysis to identify bound molecules that reliably diagnose sarcoidosis.

55. A method of detecting sarcoidosis or tuberculosis antigens by preparing: (a) a phage display library of sarcoidosis or tuberculosis antigens from cells of one or more subjects with sarcoidosis; (b) enriching the phage display library for sarcoidosis or tuberculosis antigens by biopanning; (c) selecting clones for amplification; (d) testing amplified clones for binding to antibodies in sera of sarcoidosis subjects; and (e) sequencing bound clones.

56. A method of embodiment 55 wherein the cells are bronchoalveolar cells (BAL) and white blood cells.

57. A method of any one of embodiments 55 or 56 wherein the sarcoidosis subject has systemic sarcoidosis, pulmonary sarcoidosis, cutaneous sarcoidosis, Lofgren's syndrome, neurosarcoidosis, cardiac sarcoidosis, ocular sarcoidosis, hepatic sarcoidosis, musculoskeletal sarcoidosis, renal sarcoidosis, or sarcoidosis with the involvement of other organs or tissues.

58. A method of any one of embodiments 55-58 wherein the detected sarcoidosis antigens are specific to systemic sarcoidosis, pulmonary sarcoidosis, cutaneous sarcoidosis, Lofgren's syndrome, neurosarcoidosis, cardiac sarcoidosis, ocular sarcoidosis, hepatic sarcoidosis, musculoskeletal sarcoidosis, renal sarcoidosis, or sarcoidosis with the involvement of other organs or tissues.

59. A kit to practice a method of any one of embodiments 31-45 or 54-58.

60. A method of identifying markers for sarcoidosis including preparing a cDNA library including mRNA isolated from (i) bronchoalveolar cells (BAL) of sarcoidosis patients; and (ii) white blood cells obtained from sarcoidosis patients, (iii) human splenic monocytes; and (iv) embryonic lung fibroblasts; biopanning the cDNA library to isolate clones expressing antigens for sarcoidosis from the cDNA library; and identifying the antigens as markers for sarcoidosis.

61. The method of embodiment 60, wherein biopanning includes differential biopanning.

62 The method of any one of embodiments 60 or 61, wherein differential biopanning includes using sera from healthy control subjects to remove non-specific IgG.

63. The method of any one of embodiments 60-62, wherein differential biopanning further includes using sarcoidosis sera for positive enrichment.

64. The method of any one of embodiments 60-63, wherein identifying the antigens includes immobilizing the clones on a microarray; contacting the antigens in the clones with sera of sarcoidosis patients; and analyzing binding of the antigens to the sera.

65. The method of any one of embodiments 60-64, wherein analyzing binding of the antigens to the sera includes quantifying the binding of the antigens to the sera.

66. The method of any one of embodiments 60-65, wherein the analyzing binding of the antigens to the sera includes comparing the binding of the antigens to the sera of sarcoidosis patients with the binding of the antigens to the sera of healthy subjects.

67. The method of any one of embodiments 60-66, further includes identifying markers for tuberculosis, the method further including obtaining the clones expressing the antigens identified as markers for sarcoidosis, contacting the clones with sera from tuberculosis patients to identify clones expressing antigens for tuberculosis, and identifying the antigens as markers for tuberculosis.

68. A microarray including a protein that binds CCL21; Metap1; PC4; CLI_3190; TNFRSF21; CD14; DNAJC1; APBB1; FGFBP-2; or SH3YL1.

69. A microarray including a protein that binds Fed A; WDFY3; MFS; LRPPRC; HLA-DR; TKT; Rv0189C; BfrA; DAB2; or TCEB2.

70. A microarray including a nucleic acid that binds to a gene encoding CCL21; Metap1; PC4; CLI_3190; TNFRSF21; CD14; DNAJC1; APBB1; FGFBP-2; or SH3YL1.

71. A microarray including a nucleic acid that binds a gene encoding Fed A; WDFY3; MFS; LRPPRC; HLA-DR; TKT; Rv0189C; BfrA; DAB2; or TCEB2.

72. A microarray including one or more of the following proteins: CCL21; Metap1; PC4; CLI_3190; TNFRSF21; CD14; DNAJC1; APBB1; FGFBP-2; or SH3YL1.

73. A microarray including one or more of the following proteins Fed A; WDFY3; MFS; LRPPRC; HLA-DR; TKT; Rv0189C; BfrA; DAB2; or TCEB2.

74. The microarray of any one of embodiments 68-73, wherein the protein or the nucleic acid on the microarray includes a label that can be detected.

75. The microarray of any one of embodiments 68, 69, or 72-74, wherein the microarray includes two or more, three or more, four or more, five or more, six or more, seven or more, eight or more, or nine or more of the proteins on the microarray.

76. The microarray of any one of embodiments 70, 71, or 74, wherein the microarray includes two or more, three or more, four or more, five or more, six or more, seven or more, eight or more, or nine or more of the nucleic acids on the microarray.

77. A kit comprising the microarray of any one of embodiments 68-76.

78. A method of treating a subject having symptoms of sarcoidosis including:
    diagnosing whether the subject has sarcoidosis, the diagnosing including,
        obtaining a sample from the subject,
        contacting the microarray of any one of embodiments 68, 70, or 72 with the sample from the subject,
        detecting up- and/or down-regulation of a protein or nucleic acid on the microarray as compared to a reference level, thereby diagnosing the subject has sarcoidosis; and
    treating the subject with a drug that alleviates the symptoms of sarcoidosis.

79. The method of embodiment 78, wherein the drug is a nonsteroidal anti-inflammatory.

80. The method of embodiment 79, wherein the drug is corticosteroids, methotrexate, azathioprine, hydroxychloroquine, chloroquine, cyclophosphamide, chlorambucil, pentoxifylline, thalidomide, infliximab, adalimumab, or colchicine.

81. A method of treating a subject having symptoms of tuberculosis and sarcoidosis including:
    diagnosing that the subject has tuberculosis, the diagnosing including,
        obtaining a biological sample from the subject,
        contacting the protein microarray of embodiment 69, 71, or 73 or with the biological sample from the subject, detecting up- and/or down-regulation of a protein or nucleic acid on the microarray, thereby diagnosing the subject has tuberculosis; and treating the subject with a drug that alleviate the symptoms of tuberculosis.

82. The method of embodiment 81, wherein the drug is isoniazid (INH), rifampin (RIF), ethambutol (EMB), orpyrazinamide (PZA)). The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

83. A computer-implemented method of diagnosing subjects having sarcoidosis, the computer-implemented method including:

receiving at a computer system a value representing an expression of one or more of the following markers in a subject sample: CCL21; Metap1; PC4; CLI_3190; TNFRSF21; CD14; DNAJC1; APBB1; FGFBP-2; or SH3YL1;

generating a score based at least in part on the one or more values and a weight associated with each of the one or more corresponding markers;

comparing the score to a reference level; and diagnosing the subject as having sarcoidosis or not having sarcoidosis based on a result of the comparison.

84. A computing device for diagnosing sarcoidosis including:

a processing unit;

a memory;

a user interface;

a scoring module configured to:

receive a value representing an expression of each of one or more of the following markers: CCL21; Metap1; PC4; CLI_3190; TNFRSF21; CD14; DNAJC1; APBB1; FGFBP-2; or SH3YL1; and generate a score based at least in part on the one or more values and a weight associated with each of the corresponding markers; and a diagnostic module configured to:

compare the score to a reference level;

diagnose the subject as having sarcoidosis or not having sarcoidosis based on a result of the comparison; and publish the diagnosis to the user interface.

85. A computer-implemented method of distinguishing sarcoidosis from tuberculosis in a subject, the computer-implemented method including:

receiving at a computer system a value representing an expression of each of one or more of the following markers in a subject sample: Fed A; WDFY3; MFS; LRPPRC; HLA-DR; TKT; Rv0189C; BfrA; DAB2; or TCEB2;

generating a score based at least in part on the value and a weight associated with each of the one or more markers;

comparing the score to a reference level;

diagnosing the subject as healthy, having sarcoidosis, or having tuberculosis based on a result of the comparison; and publishing a result.

86. A computing device for diagnosing sarcoidosis including:

a processing unit;

a memory;

a user interface;

a scoring module configured to:

receive a reference level, and a value representing an expression each of one or more of the following markers in a subject sample: Fed A; WDFY3; MFS; LRPPRC; HLA-DR; TKT; Rv0189C; BfrA; DAB2; or TCEB2; and generate a score based at least in part on the value and a weight associated with each of the one or more markers; and a diagnostic module configured to:

compare the score to a reference level;

diagnose the subject as having sarcoidosis or not having sarcoidosis based on a result of the comparison; and publish the diagnosis to the user interface.

87. The computer-implemented method of embodiments 83 or 85, the method includes receiving a reference level.

88. The computer device of embodiments 84 or 86, wherein the scoring module receives a reference level.

Examples. Significance. Aberrant immune responses are a major cause of a vast array of human diseases. Sarcoidosis is an inflammatory disease of unknown etiology sharing similarities with non-infectious and infectious granulomatous diseases, including *Mycobacteria tuberculosis*. Tuberculosis (TB) remains a major global health problem. There is a tremendous need to develop accurate tests to diagnose sarcoidosis and TB. A highly sensitive and specific T7 phage antigen library derived from bronchoalveolar lavage cells and leukocytes of sarcoidosis subjects was developed. This complex cDNA library was biopanned and a microarray was constructed to immunoscreen sera from healthy, sarcoidosis and TB subjects. A panel of specific antigens to classify sarcoidosis from healthy controls and subjects with TB was identified.

Introduction. Sarcoidosis is an inflammatory granulomatous disease of unknown etiology affecting multiple organs, such as lungs, skin, CNS, and eyes. Common features shared by patients with sarcoidosis are the presence of non-caseating granuloma, a lack of cutaneous reaction to tuberculin skin testing (PPD) and increased local and circulating inflammatory cytokines. In addition, there is evidence of abnormal immune function that presents as cutaneous anergy accompanied by hypergammaglobulinemia. Sarcoidosis shares striking clinical and pathological similarities with infectious granulomatous diseases, especially *Mycobacteria tuberculosis* (MTB). Iannuzzi et al., N. Engl. J. Med. 2007; 357(21): 2153-65; Prince et al., J. Allergy Clin. Immunol. 2003; 111(2 Suppl): S613-23. Although there is mounting evidence of the presence of nonviable bacterial components (including MTB and Propionibacterium acnes) in sarcoidosis tissue (Gupta et al., Eur. Respir. J. 2007; 30(3): 508-16; Chen et al., Am. J. Respir. Crit. Care Med.; 181(4): 360-73; Negi et al., Modern pathology: an official journal of the United States and Canadian Academy of Pathology, Inc. 2012; 25(9): 1284-97) all attempts to isolate viable MTB or other microbial pathogens from sarcoidosis tissue have failed. Hunninghake et al. Sarcoidosis Vasc Diffuse Lung Dis 1999; 16(2): 149-73; Chen et al. J. Immunol. 2008; 181(12): 8784-96.

Intradermal injection of the Kveim-Siltzbach suspension (a granulomatous splenic tissue suspension) induces granuloma formation weeks later in sarcoidosis patients suggesting the presence of antigen(s) in granuloma tissue and host immunoreactivity to these antigens. Proteomics, genomics, transcriptomics, and high throughput technology clearly suggest that early immune reaction to diverse antigens is highly prevalent in a large number of rheumatic, neoplastic, and inflammatory diseases such as sarcoidosis. Several studies using state-of-the-art technologies have attempted to identify sarcoidosis antigens or to identify the underlying genetic and environmental factors (Hajizadeh et al., J. Clin. Immunol. 2007; 27(4): 445-54; Chen et al., Proc. Am. Thorac. Soc. 2007; 4(1): 101-7; Zhang et al., Respiratory research 2013; 14: 18) yet unifying environmental or genetic factors as initiators of this disease have not been found. Hunninghake et al., Sarcoidosis Vasc Diffuse Lung Dis 1999; 16(2): 149-73; Dubaniewicz, Autoimmunity reviews 2010; 9(6): 419-24; Eishi et al., Journal of Clinical Microbiology 2002; 40(1): 198-204; Oswald-Richter & Drake, Seminars in respiratory and critical care medicine 2010; 31(4): 375-9. These studies reported a number of markers or variations in gene expression signatures, which, however, failed to discriminate between sarcoidosis and other inflammatory or granulomatous diseases. Koth et al., Am. J. Resp. Crit. Care 2011; 184(10): 1153-63; Maertzdorf et al. Proc. Natl. Acad. Sci. USA 2012; 109(20): 7853-8. This is partly due to the fact that several inflammatory diseases may respond to various antigens with activation of a similar transcriptome and/or inflammatory gene expression profiles.

Because non-caseating granulomas, cutaneous anergy and hypergammaglobulinemia suggest an immune dysfunction in this disease, it was hypothesized that sarcoidosis is triggered by a group of unknown antigens represented in the host immune cells. To identify the elusive antigen(s), a heterologous cDNA library derived from bronchoalveolar cell (BAL) samples and total white blood cells (WBC) from sarcoidosis patients was developed. Both sarcoid-derived libraries were then combined with cultured human monocytes and embryonic lung fibroblast cDNA libraries to build a complex sarcoidosis library (CSL). Furthermore, antibody recognition and random plaque selection was used during biopanning of the cDNA libraries to minimize the confounding effects of autoantibodies unrelated to sarcoidosis. It was tested whether this novel library representing relevant antigens could specifically recognize high IgG titer in sera of sarcoidosis subjects. This approach has been successfully applied in biomarker discovery for the diagnosis of lung, head and neck and breast cancer. Fernandez-Madrid et al., Cancer research 2004; 64(15): 5089-96; Fernandez-Madrid et al., Clinical cancer research: an official journal of the American Association for Cancer Research 1999; 5(6): 1393-400; Lin et al., Cancer epidemiology, biomarkers & prevention: a publication of the American Association for Cancer Research, cosponsored by the American Society of Preventive Oncology 2007; 16(11): 2396-405. A feature that distinguishes the described methods from previous studies is that the exquisite power of antibody recognition present in the sera of sarcoidosis patients was used to interrogate the potential antigens presented in the macrophages and monocytes.

The present study describes a novel approach to identify sarcoidosis antigens and to detect serum antibodies on high-throughput arrays. Sera from 3 cohorts (sarcoidosis, controls, and TB) were used for immunoscreening. Using bioinformatics tools, a large number of biomarkers with high sensitivity and specificity that can discriminate among the sera of patients with sarcoidosis, healthy controls and MTB was identified. Using the integrative-analysis method that combines results from two independent trials, clones that significantly differentiate sarcoidosis from controls were identified. Similarly, clones that differentially react with TB sera and not with sarcoidosis or control sera were identified. Furthermore, the top 10 discriminating antigens for TB and sarcoidosis were sequenced and homologies were identified in a public data base. These data indicate that a unique library enabling the detection of highly significant antigens to discriminate between patients with sarcoidosis and tuberculosis was developed.

Materials and Methods. Chemicals. All chemicals were purchased from Sigma-Aldrich (St. Louis, Mo.) unless specified otherwise. LeukoLOCK filters and RNAlater were purchased from Life Technologies (Grand Island, N.Y.). The RNeasy Midi kit was obtained from Qiagen, (Valencia, Calif.). The T7 mouse monoclonal antibody was purchased from Novagen (San Diego, Calif.). Alexa Fluor 647 goat anti-human IgG and AlexFluor goat anti-mouse IgG antibodies were purchased from Life Technologies (Grand Island, N.Y.).

Patient selection. This study was approved by the Institutional Review Board at Wayne State University and the Detroit Medical Center. Patients were recruited at the center for Sarcoidosis and Interstitial Lung Diseases (SILD), which is a referral center for patients with sarcoidosis and other ILDs. Three sources of patient derived materials have been used in this study: A) a BAL cDNA library was derived from BAL cells obtained during diagnostic bronchoscopy from newly diagnosed patients with sarcoidosis (n=20); B) a leukocyte cDNA library were developed from sarcoidosis patients who were followed in outpatient setting with various stages of sarcoidosis (n=36); and C) sera collected from 3 groups: 1) healthy controls, who were volunteers recruited from the community; 2) subjects with biopsy confirmed sarcoidosis who were followed in an outpatient setting; and 3) sera from subjects with culture positive TB collected at the Detroit Department of Health and Wellness Promotion. Subjects were included who had a diagnosis of sarcoidosis as proven by tissue biopsy per guidelines (Costabel & Hunninghake, Eur Respir J 1999; 14(4): 735-7) and have a negative PPD. TB subjects were included who had a positive TB culture and were HIV negative. Subjects were excluded, who were positive for HIV or were receiving high dose immune suppressive medication that was defined as prednisone more than 15 mg alone or in combination with immune modulatory medications. Subjects who had positive PPD or quantiferon test were excluded from the sarcoidosis group. All study subjects signed a written informed consent.

Bronchoalveolar lavage: BAL cells were obtained, after informed consent, during diagnostic bronchoscopy from subjects with active sarcoidosis as previously described. Rastogi et al., American journal of respiratory and critical care medicine 2011; 183(4): 500-10. BAL cells were suspended in 500p1 of RNAlater and stored at −80° C.

Collection of total leukocytes from sarcoid subjects. Leukocytes from 36 sarcoid subjects were isolated using whole blood with LeukoLOCK filters as previously described. Glatt et al., Current pharmacogenomics and personalized medicine 2009; 7(3): 164-88.

Human macrophage (EL-1) and human lung embryonic fibroblast (MRC-5) cell cultures. Both cell lines were obtained from ATCC and cultured as per ATTC recommendations. From each cell line 1-2 mg RNA was isolated to construct the cDNA library.

Serum collection. Using standardized phlebotomy procedures blood samples were collected and allowed to clot and then centrifuged at 2500 rpm for 10 min. Supernatants were stored at −80° C.

Construction of T7 phage display cDNA libraries. Total RNA was isolated using the RNeasy Midi kit (Qiagen, Valencia, Calif.). Integrity of the RNA samples was assessed using the Agilent 2100 bioanalyzer. Total RNA, in the amount of 1-2 mg, was subjected to two cycles of polyA purification to minimize ribosomal RNA contamination as suggested by the manufacturer (Qiagen, Valencia, Calif.). The construction of phage cDNA libraries was performed using Novagen's Orient Express cDNA Synthesis (Random Primer System) and Cloning system as per manufacturer's suggestions (EMD Biosciences-Novagen). Each library was cloned using modified linkers that allow identification of the phage clones. Chatterjee et al., Cancer research 2006; 66(2): 1181-90. The number of clones in each of the 4 libraries was titrated by plaque assay as per manufacturer's instructions (EMD Biosciences-Novagen). Finally, the same number of phages from each BAL, WBC, EL-1 and MRC5 library was pooled to generate a complex sarcoid library (CSL).

Biopanning of T7 phage displayed cDNA library with human sera. Differential biopanning for negative and positive selection was performed using sera from healthy controls to remove the non-specific IgG, and sarcoidosis sera for selective enrichment according to manufacturer's suggestions (T7Select System, TB178; EMD Biosciences-Novagen). Protein G Plus-agarose beads (Santa Cruz Biotechnology) were used for serum IgG immobilization. Four rounds of biopannings were performed and the selected phage libraries were used for microarray immunoscreening. Each cycle of biopanning included passing the entire phage library through protein G beads coated with IgG from pooled sera of healthy controls, then passing through beads coated with IgGs from individual serum of sarcoid subjects. Microarray construction and immunoscreening. Informative phage clones were randomly picked and amplified after several rounds of biopannings and their lysates were arrayed in quintuplicates onto nitrocellulose FAST slides (Grace Biolabs, OR) using the ProSys 5510TL robot (Cartesian Technologies, CA). The nitrocellulose slides were then blocked with a solution of 1% BSA in PBS for 1 hour at room temperature followed by another hour of incubation with serum at a dilution of 1:300 in 1×PBS or plasma at a dilution of 1:100 as primary antibodies, together with mouse anti-T7 capsid antibody (0.15 µg/mL) and BL21 $E.$ $coli$ cell lysates (5 µg/mL). BL21 $E.$ $coli$ cell lysates were added to remove antibodies specific to $E.$ $coli$ from the serum. The microarrays were then washed three times at room temperature with a solution of PBS/0.1% Tween20 for 4 minutes. Secondary antibodies included goat anti-human IgG Alexa Fluor 647 (red fluorescent dye) 1 µg/mL and goat anti-mouse IgG Alexa Fluor 532 (green fluorescent dye) 0.05 µg/mL. After 1 hour incubation in the dark, the microarrays were washed 3 times with a solution of PBS/0.1% Tween20 for 4 minutes at room temperature, and 2 times in PBS for 4 minutes at room temperature and then air dried.

Sequencing of phage cDNA clones. Individual phage clones were PCR amplified using T7 phage forward primer 5' GTTCTATCCGCAACGTTATGG 3' (SEQ ID NO. 75) and reverse primer 5' GGAGGAAAGTCGTTTTTTGGGG 3' (SEQ ID NO. 76) and sequenced by Genwiz (South Plainfield, N.J.), using T7 phage sequence primer TGCTAAGGACAACGTTATCGG (SEQ ID NO. 77).

Data acquisition and pre-processing. Following the immunoreaction, the microarrays were scanned in an Axon Laboratories 4100 scanner (Palo Alto, Calif.) using 532 and 647 nm lasers to produce a red (Alexa Fluor 647) and green (Alexa Fluor 532) composite image. Using the ImaGene 6.0 (Biodiscovery) image analysis software, the binding of each sarcoid specific peptide with IgGs in each serum was then analyzed and expressed as a ratio of red-to-green fluorescent intensities. The microarray data were further read into the R environment v2.3.0 (Team RDC. R: a language and environment for statistical computing. R Foundation for Statistical Computing; Vienna (Austria). 2004) and processed by a sequence of pre-processing, including background correction, omission of poor quality spots and log2 transformations. Within array loess normalization was performed for each spot and summarized by median of triplicates and followed by between array quantile normalization.

Statistical analysis. A microarray analysis was performed using sera from sarcoid and healthy controls in two independent sets of experiments. Technical and biological sources of variation were expected in the design of the experiment. As opposed to pooling all datasets, one powerful and robust method is to integrate results from individual datasets. Obtaining a higher confidence list of markers than by using individual datasets was expected. To detect differentially expressed antigens between sarcoidosis samples and healthy controls, an integrative analysis of two datasets was performed. Limma's empirical Bayes moderated t-test identified fold-changes in expression of antigens that differed significantly between sarcoidosis and controls for each dataset separately. Then an integrative-analysis method—an adaptively-weighted method with one-sided correction (AW-OC) (Li & Tseng, The Annals of Applied Statistics 2011; 5(2A): 994-1019) was performed to combine the statistics from both datasets. The integrative method was designed to test whether an antigen is consistently up- or down regulated in sarcoidosis subjects in both datasets. False Discovery Rate (FDR) was estimated using the Benjamini-Hochberg method. Benjamini & Hochberg. J. R. Stat. Soc. Ser. B 1995; 57: 289-300.

To identify a panel of markers that classify sarcoidosis samples and controls, a strategy of univariate marker selection followed by multivariate modeling was used. The top antigens differentially expressed in the two groups were selected using the above described AW-OC approach. The top genes that were consistently up- or down-regulated in both datasets were used. The top markers were then required by the supervised classification models to achieve the most sensitivity and specificity in differentiating sarcoid and controls. The multivariate classification models chosen for this study were K-nearest neighbors (KNN) and support vector machine (SVM). The cross-validation technique was used to prevent the overfitting of data analysis due to a large number of antigens used to discriminate between sarcoid and control subjects. The study was performed in two nested 10-fold cross-validation loops, an inner loop to select the optimal number of antigens and an outer loop to measure the optimized model performance with estimation of the area under the receiver operating characteristic (AUROC) sensitivity and specificity. The receiver operating characteristic curves were estimated through 10-fold cross-validation. A moderated t-test was carried out to identify the significant clones between healthy controls, sarcoidosis and tuberculosis.

Results. Generation of cDNA libraries representative of sarcoidosis antigens. Both PBMCs and alveolar macrophages (AMs) play an important role in initiation of sarcoidosis granuloma. It has been shown that extracts from sarcoidosis BAL cells and peripheral blood monocytes (PB-MCs) are able to initiate a Kveim-like reaction. Siltzbach & Ehrlich, The American Journal of Medicine 1954; 16(6): 790-803; Holter et al., The American Review of Respiratory Disease 1992; 145(4 Pt 1): 864-71. Therefore, total BAL cells and WBCs from patients with biopsy proven sarcoidosis were used to develop a cDNA antigen library. BAL cells and WBC were used as sources of antigens in order to increase the diversity of sarcoidosis antigens. To increase the chance of identifying sarcoidosis antigen(s), RNA was isolated from BAL samples obtained from 20 patients with active sarcoidosis to generate the BAL cDNA library. The patients' characteristics are shown in Table 1 (left panel). The LeukoLock system was used to isolate RNA from total leukocytes (WBC) obtained from a different cohort of 36 sarcoidosis subjects to build the WBC cDNA library. The patients' characteristics are shown in Table 1 (right panel).

TABLE 1

Subject Demographics, Chest X-Ray Stages, and organ involvements

| BAL derived RNA | | Leukocyte derived RNA | |
| --- | --- | --- | --- |
| Age (Mean ± SEM) | 30 ± 8 | Age (Mean ± SEM) | 36 ± 11.2 |
| BMI (Mean ± SEM) | 27.7 ± 8.7 | BMI (Mean ± SEM) | 31 ± 5.4 |
| Gender, N (%) | | Gender, N (%) | |
| Male | 7 (33) | Male | 12 (33) |
| Female | 13 (67) | Female | 24 (67) |
| Race, N (%) | | Race, N (%) | |
| African American | 17 (87) | African American | 32 (88) |
| White | 3 (13) | White | 4 (12) |
| CXR stage, N (%) | | CXR Stage, N (%) | |
| 1 | 2 (6) | 1 | 1 (3) |
| 2 | 14 (67) | 2 | 13 (41) |
| 3 | 4 (27) | 3 | 12 (37) |
| 4 | 0 | 4 | 6 (19) |
| Lung | 18 | Lung | 33 |
| Extrapulmonary | 16 | Extrapulmonary | 31 |
| Neuro-ophthalmologic | 6 | Neuro-ophthalmologic | 11 |
| Skin | 6 | Skin | 13 |
| Liver | 2 | Liver | 4 |
| Heart | 1 | Heart | 2 |
| Prednisone | 1 | Prednisone | 3 |
| IMD | 0 | IMD | 14 |
| Smoking | | Smoking | |
| None | 12 | None | 26 |

Age, BMI and disease duration values are presented as means and variability in SD or range where indicated. N = Number of patients and percent shown in parentheses. IMD = immunomodulatory drugs Two other sources of cDNA, one from cultured human splenic monocytes (EL-1) and another from lung embryonic fibroblasts (MRC5) were used to generate two additional libraries. These sources were added to increase the chance of discovering potential sarcoidosis antigens. Each cDNA underwent two cycles of PolyA selection to minimize ribosomal contamination. These four libraries were developed as described in the Materials and Methods section. Each library was cloned using modified linkers; ECOR1/HindIII was used for BAL cDNA, ALA for WBC cDNA, LEU for MARC5 cDNA and THR for EL1 cDNA (FIG. 6). The use of these linkers enabled identification of the original library for each antigen.

Figure 7A:
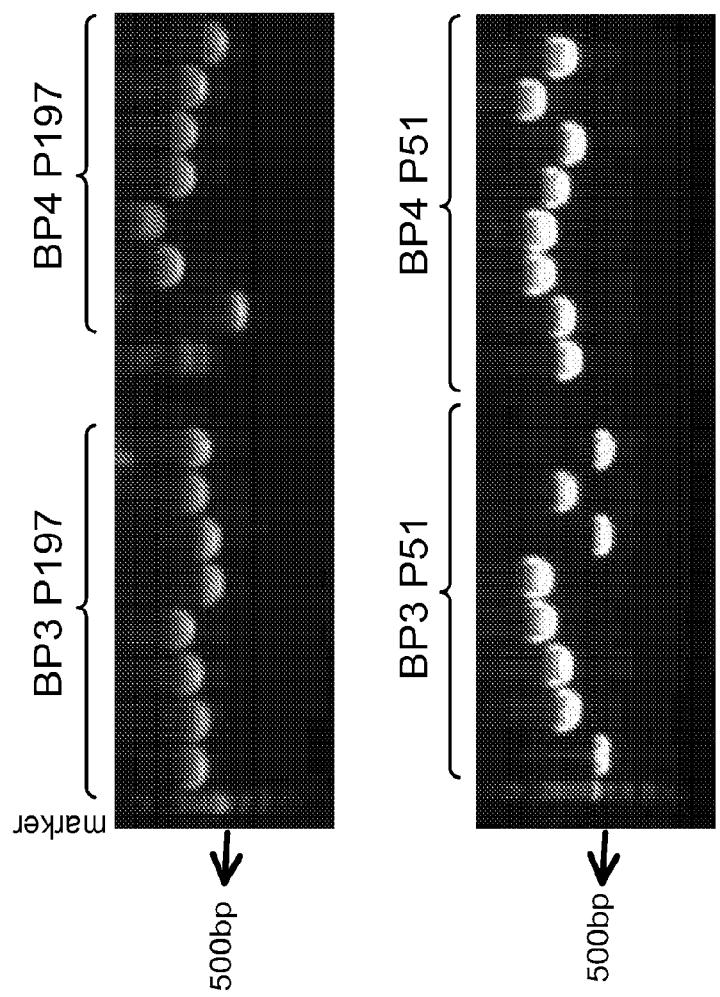
FIG. 7A shows a graphical representation of the output eluent phage titers as a function of biopanning (BP) showing exponential enrichment of the output eluent phage titers after the completion of each cycle of biopannings.
Figure 7B:
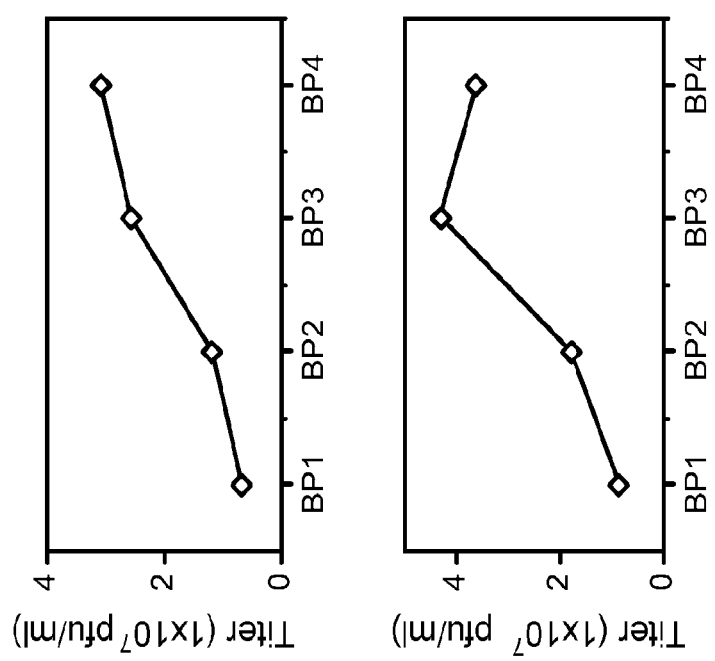
FIG. 7B shows PCR amplification of the phage clones picked up from biopannings 3 & 4 (BP3 & BP4) showing retention of diversity in the pool of immunoreactive phage.

Differential biopanning of sarcoidosis phage cDNA display libraries. The four phage cDNA display libraries (BAL, WBC, EL-1 and MARCS) were combined to generate a complex sarcoidosis library (CSL). To isolate a large panel of antigens, differential biopanning of the T7 phage cDNA display library was performed on the combined complex sarcoid library. A negative biopanning selection was done using 10 pooled sera from healthy controls to remove non-specific IgG, while 2 sarcoidosis sera were used for positive selective enrichment. One serum was obtained from a woman (P51) with systemic sarcoidosis who had uveitis and another serum was collected from a male subject (P197) who had active systemic sarcoidosis with renal involvement. Both patients had pulmonary involvements. Each clone was derived either from P51 or from P197. The titer of the complex library was assessed (FIG. 7A) and individual phage clones were amplified by PCR (FIG. 7B).

High-throughput protein microarray immunoreaction to select sarcoidosis specific antigens. A total of 1152 potential antigen antigens were randomly selected from the two highly enriched pools of T7 phage cDNA libraries (FIG. 1). These antigen antigens were robotically spotted on nitrocellulose Fast slides and were hybridized with sera of sarcoidosis patients or healthy controls. The binding of each of the arrayed potential sarcoidosis-specific peptides with antibodies in sera was quantified with Alexa Fluor 647 (red-fluorescent dye)-labeled goat anti-human antibody. The amount of phage particles at each spot throughout the microarray was detected using a mouse monoclonal antibody to the T7 capsid protein and quantified using Alexa Fluor 532 (green-fluorescent dye)-labeled goat anti-mouse antibody (FIG. 1). To correct for any small variation in the amount of antibody binding in each spot that may be due to different amounts of phage spotted on the microarray, the ratio of intensity of Alexa Fluor 647 over Alexa Fluor 532 was calculated for each spot. Following immunoreaction, the microarray data were processed by a sequence of transformations and then analyzed. The intra-assay reproducibility was assessed by comparing the results among five replicates printed within the same chip for each clone.

Selection of a panel of antigens and estimation of neural network classifier performance in sarcoidosis. A novel aspect of the described work was the integration of data from two independent trials of printing allowing the development of two data sets obtained from two independent cohorts of sarcoidosis patients and healthy controls utilized for hybridization. To generate the first dataset, sera from 54 sarcoidosis subjects and 45 healthy controls were immune-screened against 1152 sarcoidosis specific peptides. In a second dataset, sera from 19 healthy controls and 61 sarcoidosis subjects were similarly immune-screened with 1152 potential sarcoidosis specific antigens. Sera used in both data sets for hybridization had not been previously used for biopanning or selection of clones. Table 2 shows the clinical characteristics of sarcoidosis and healthy control subjects.

TABLE 2

| Patient characteristics | | Control Subjects |
| --- | --- | --- |
| Age | 29.7 ± 13.4 y | 33 ± 7.4 |
| BMI | 29 ± 10.4 | 28 ± 3.6 |
| Gender, N | | |
| Female | 87 (75) | 48 (75) |
| Male | 28 (25) | 16 (25) |
| Race, N | | |
| African American | 107 (89) | 44 (69) |
| White | 8 (11) | 20 (31) |
| CXR stage, N | | |
| 0 | 3 (2) | NA |
| 1 | 18 (15) | NA |
| 2 | 49 (43) | NA |
| 3 | 45 (39) | NA |
| Organ Involvements, | 33 (28) | NA |
| Neuro-ophthalmologic | | |
| Lung | 109 (94) | NA |
| Skin | 50 (45) | NA |
| Multiorgan | 70 (52) | NA |

Some Patients had multiple organ involvements
NA = Not Applicable

Figure 2B:
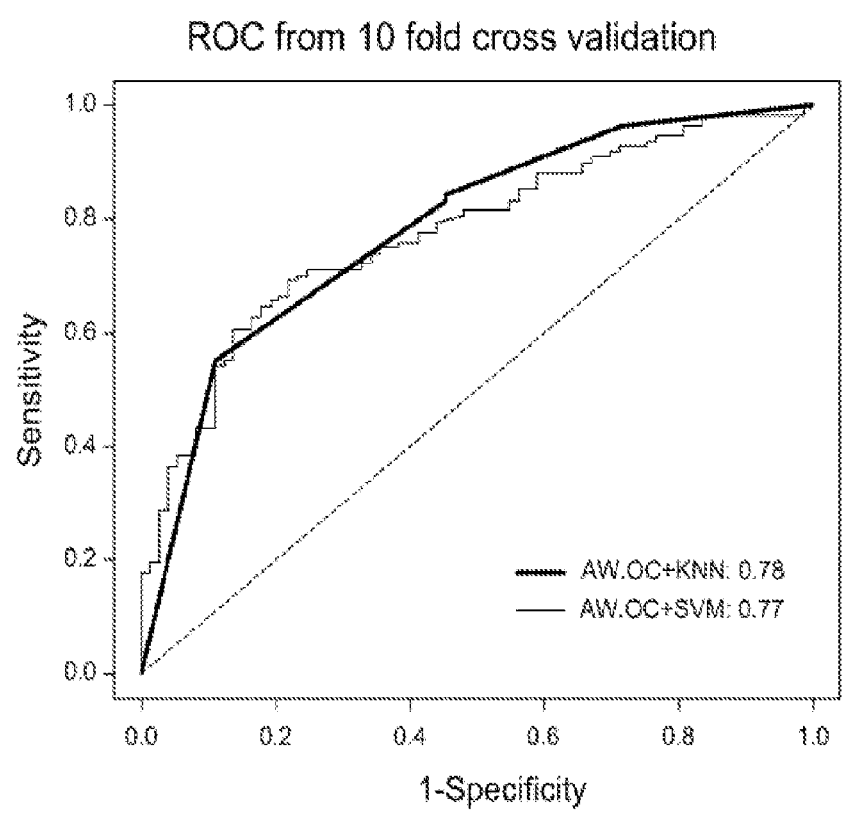
FIG. 2B shows receiver operating characteristics (ROC) curves demonstrating the performance of 32 classifiers to discriminate between healthy controls and sarcoidosis subjects.
Figure 3A:
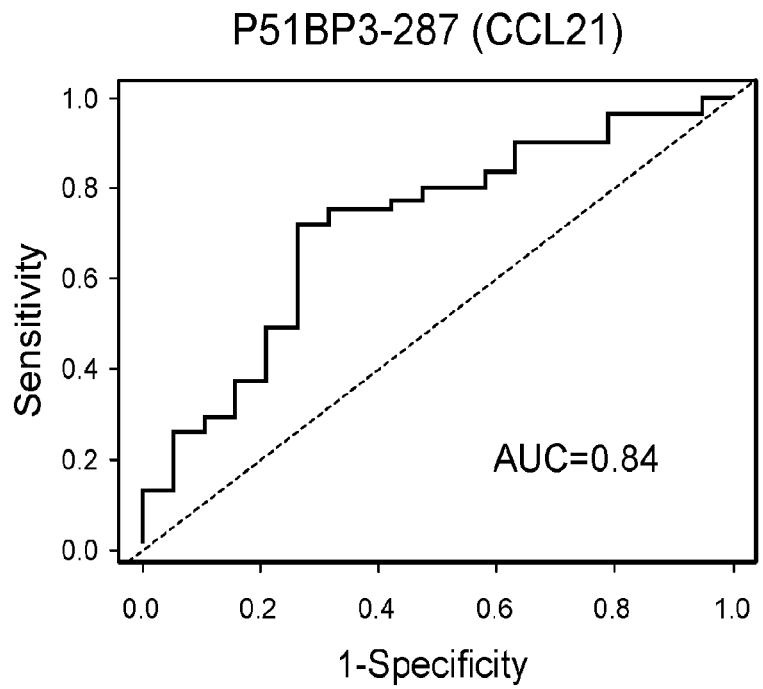
FIGS. 3A-3J show receiver operating characteristics (ROC) curves for the top 10 sarcoidosis clones as follows: 3A (CCL21); 3B (Metap1); 3C (PC4); 3D (CLI_3190); 3E (TNFRSF21); 3F (CD14); 3G (DNAJC1); 3H (APBB1); 3I (FGFBP-2); and 3J (SH3YL1).
Figure 3B:
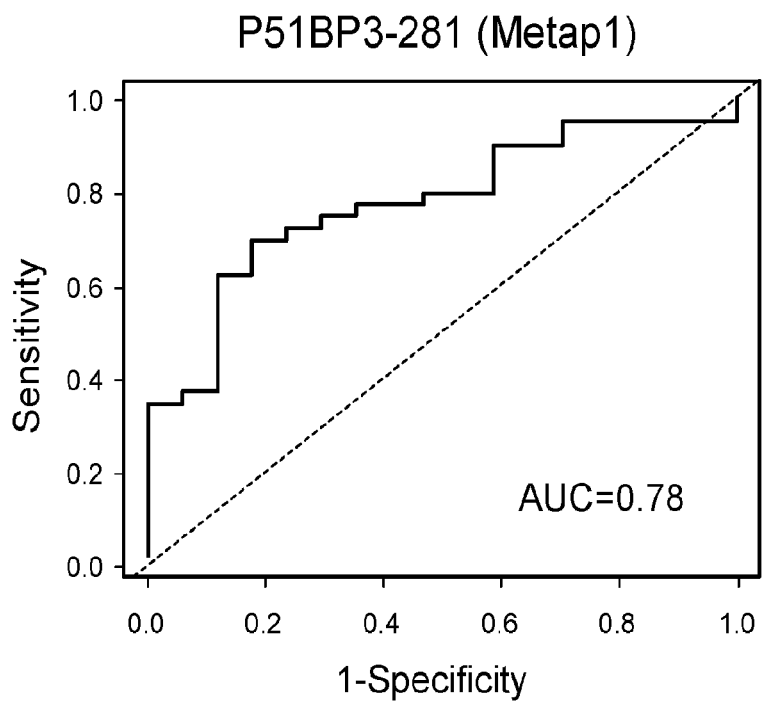
Figure 3C:
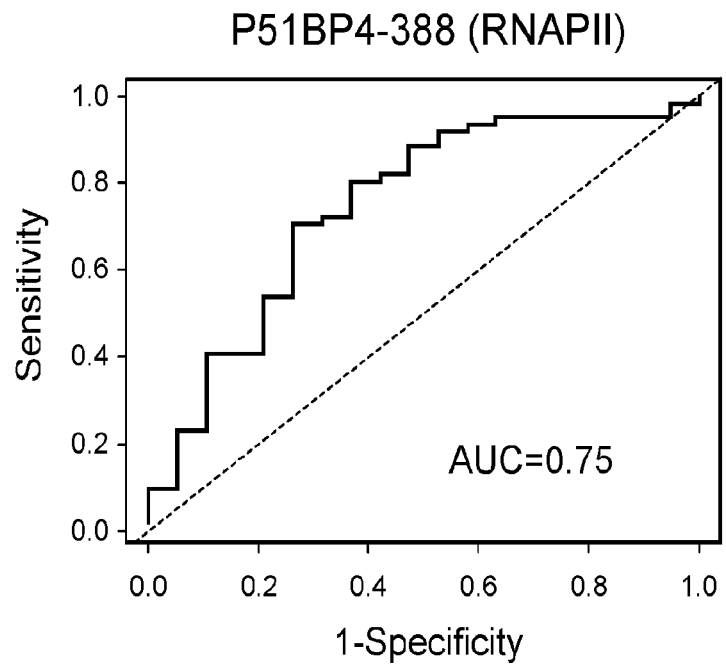
Figure 3D:
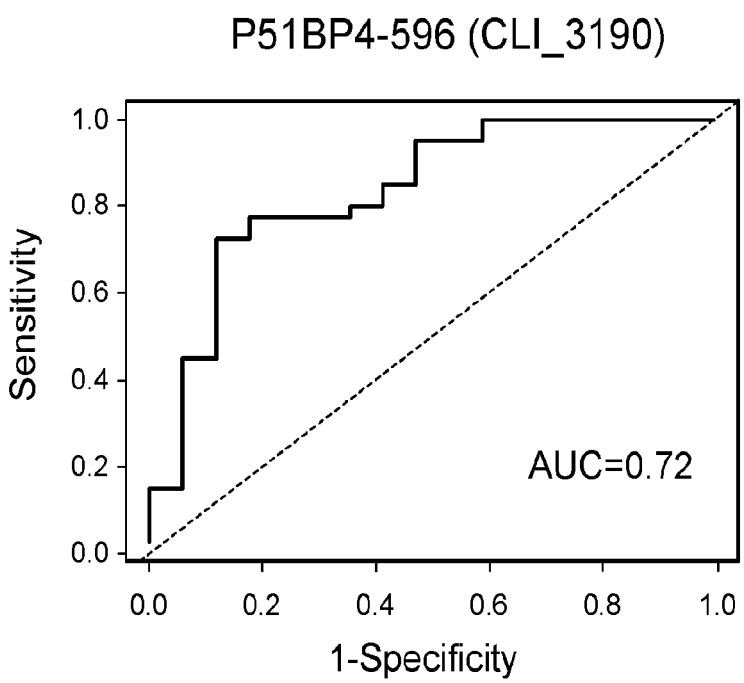
Figure 3E:
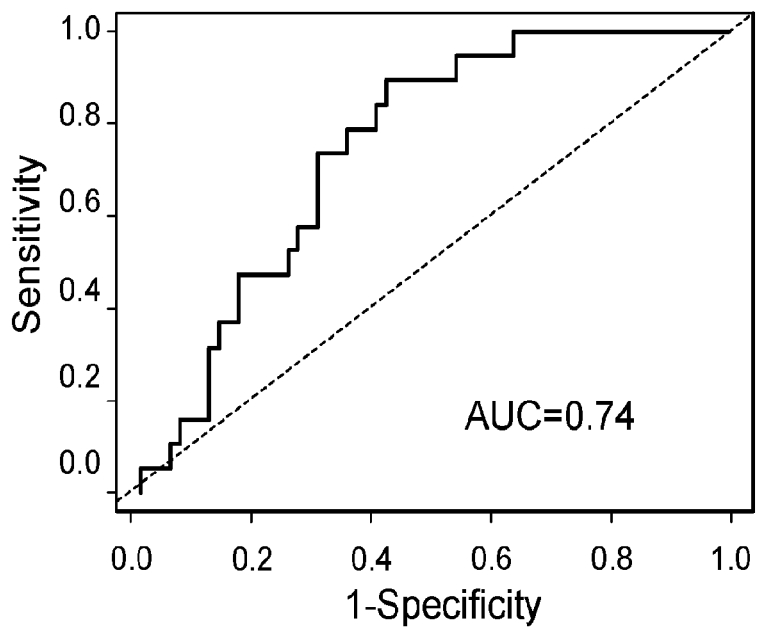
Figure 3F:
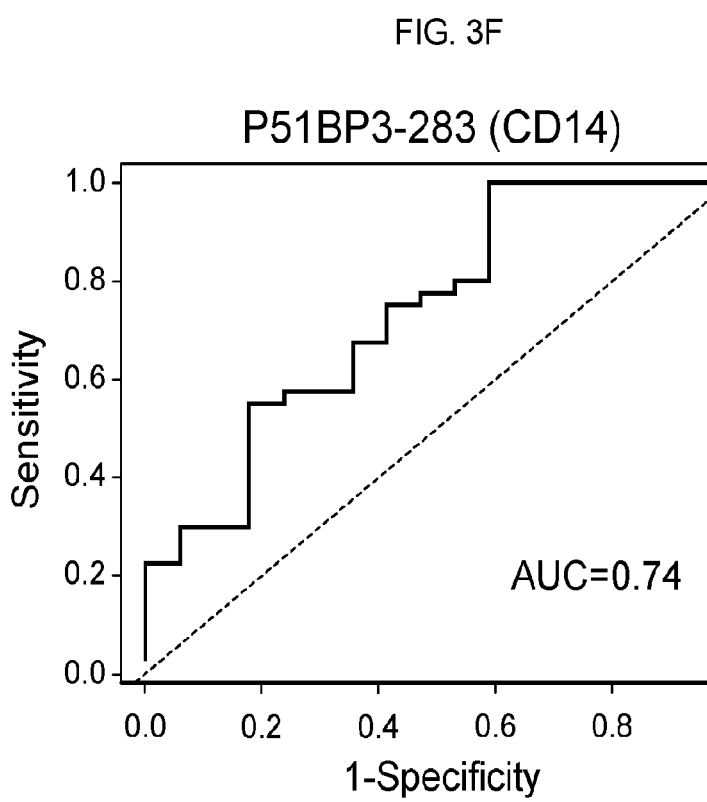
Figure 3G:
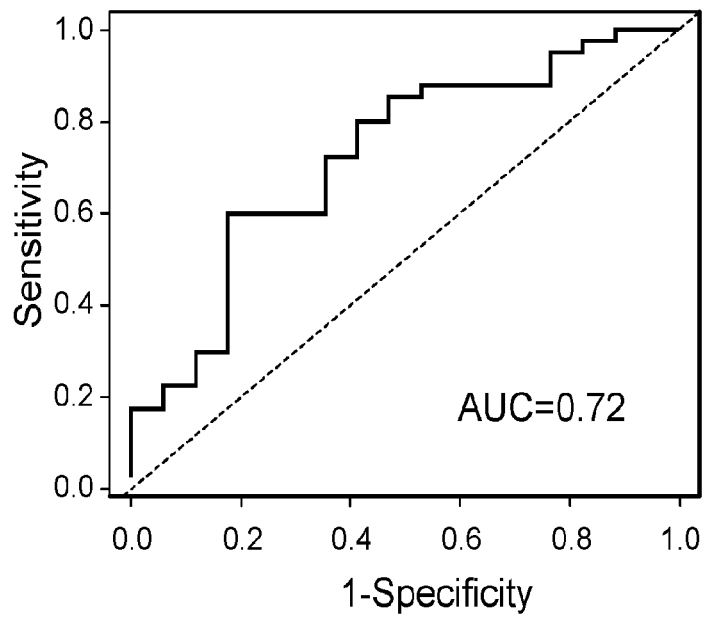
Figure 3H:
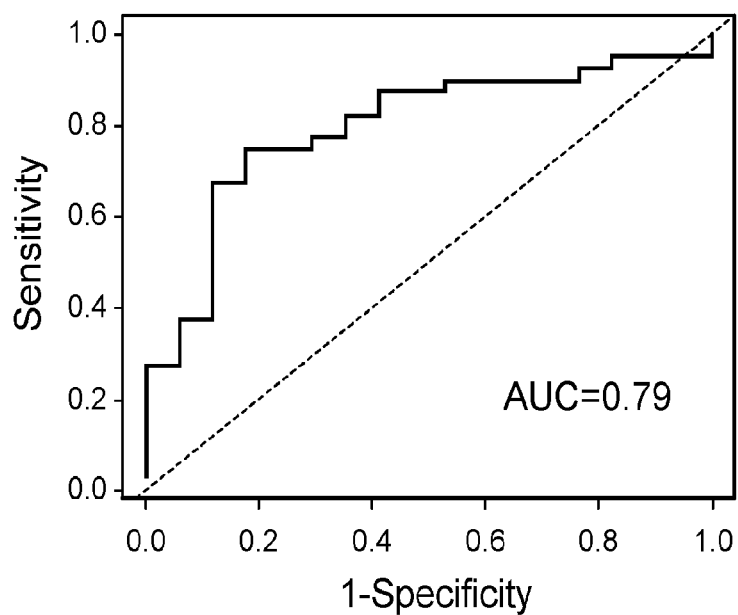
Figure 3I:
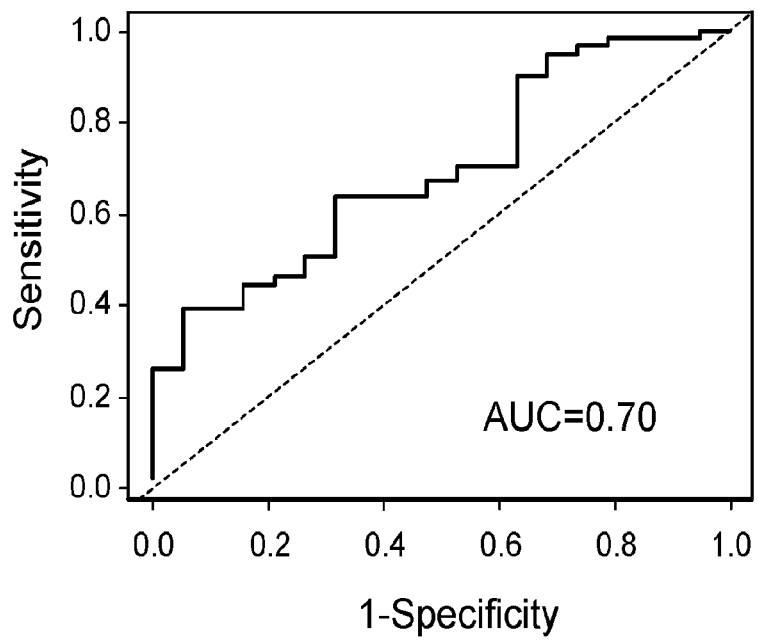
Figure 3J:
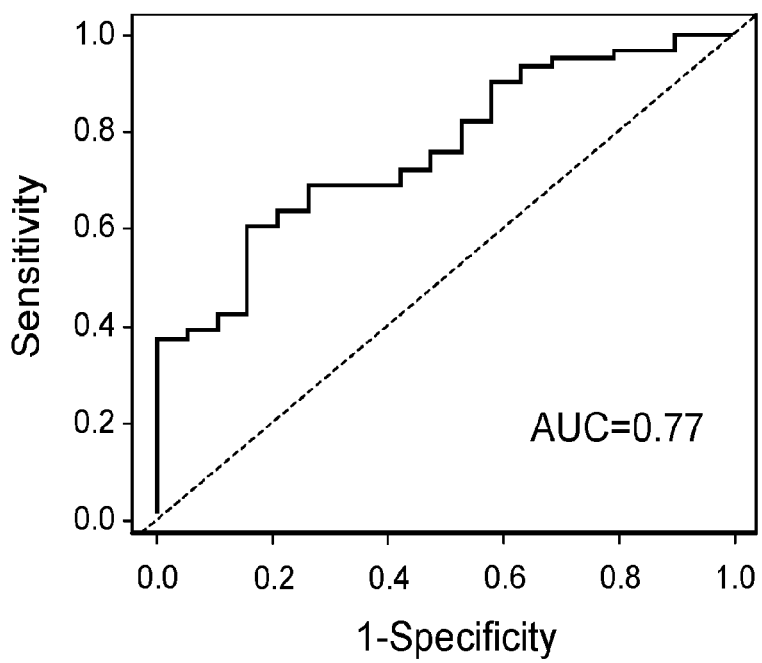

Within array loess normalization was performed for each spot and summarized by median of triplicates and followed by between array quantile normalization. After preprocessing, 1101 antigens common in both datasets were used for further analysis. Univariate and multivariate analyses were performed. Limma's empirical Bayes moderated t-test was used to identify fold-changes in expression of antigens that differed significantly between sarcoidosis and controls for each dataset separately. Then both datasets were combined using an integrative-analysis method—an adaptively-weighted method with one-sided correction (AW-OC). Li & Tseng, The Annals of Applied Statistics 2011; 5(2A): 994-1019. Out of the 1101 potential antigen, 259 showed a strong differentiation between sarcoidosis and healthy control subjects with adjusted p value (q value) <0.05 and FDR (false discovery rate) <0.05. FIG. 2A shows the heatmap of the 259 significant antigens that were differentially expressed in both datasets. Seventy eight markers out of 259 were consistently up- or down-regulated in sarcoidosis subjects. FIG. 2B shows the AUROC for this classifier. KNN method performed slightly better than SVM. Using the highly significant 32 antigens selected by AW.00 and KNN methods to classify sarcoidosis and healthy controls (AW.00+KNN), the area under the curve (AUROC) was 0.78, with a sensitivity of 89% and a specificity of 83% estimated after 10-fold cross-validation (FIG. 2B).

Characterization of 10 most significant sarcoid antigens. Based on the results of AW-OC integrative-analysis, the top 10 high performance antigens that predict sarcoidosis were identified. To further characterize the performance of each clone, the AU-ROC, and sensitivity and specificity given the optimal cutoff of the clones was calculated. FIG. 3 depicts the ROC curves for individual sarcoid antigens and their adjusted p value (q value). As shown, each antigen has a different specificity and sensitivity as well as ROC to predict the presence of sarcoidosis. ROC for these antigens ranged from the highest of 0.84 to the lowest of 0.7. Nine of 10 antigens were clearly up-regulated, whereas one was down-regulated. To further characterize the identified antigens, these 10 highest ranked antigens were sequenced. After obtaining the sequences of clones, the Expasy program was used to translate the cDNA sequences to protein sequences. Protein blast using Blastn and tblastn algorithms of the BLAST program were applied to identify the highest homology to identified proteins or peptides and these results were compared with corresponding nucleotide sequences using nucleotide blast. The predicted amino acid in frame with phage T7 gene 10 capsid proteins was also determined. Five Antigens (PC4, SAMDHI, DNAJC1, TPT1 and SH3YL1) among the top 10 fit the definition of an epitope containing known gene products in the reading frame known genes. The other five contained peptides coded by the inserted gene fragments leading to out of frame peptides, which fits the definition of mimotopes. Among the 10 high performance clones, nine were up-regulated and only one was down-regulated in sarcoidosis versus healthy controls. FIG. 8 shows the full length of proteins and genes of 10 sarcoidosis clones. Without being bound by theory, as sarcoidosis sera reacted to these out of frame peptides, it is likely that these clones represent sarcoidosis antigens produced as a result of altered reading frames or alternative splicing. Interestingly, when a similar technique was applied to discovery of cancer antigens, numerous out of frame peptides were discovered. Lin et al., Cancer epidemiology, biomarkers & prevention: a publication of the American Association for Cancer Research, cosponsored by the American Society of Preventive Oncology 2007; 16(11): 2396-405. Table 3 shows the 10 most significant sarcoidosis antigens, gene names and q-values.

| Clone | Up-Regulated in Sarcoidosis Vs Healthy | Gene Name | q Value AUC | Sensitivity// Specificity %, 95% CI |
|---|---|---|---|---|
| P51_BP3_287 (MRCS) | Small inducible cytokine A21 precursor | CCL21 | $1.9 \times 10^{-20}$ 0.84 | 78//82 |
| P51_BP3_281 (BAL) | Methionine aminopeptidase 1 | Metap1 | $1.0 \times 10^{-20}$ 0.78 | 70//82 |
| P51_BP4_388 (EL-1) | Activated RNA polymerase II transcription cofactor variant 4 | PC4 | 0.00045 0.75 | 70//74 |
| P51_BP4_596 (WBC) | RNA methyl-transferase | CLI_3190 | 0.00045 0.72 | 72//74 |
| P51_BP4_566 (WBC) | Tumor necrosis factor receptor superfamily member 21 precursor. Also known as death receptor 6 (DR6) | TNFR SF21 | 0.0009 0.74 | 70//71 |
| P51_BP3_283 (WBC) | Monocyte differentiation antigen CD14 | CD14 | 0.0009 0.74 | 68//65 |
| P51_BP3_47 (EL-1) | DnaJ (Hsp40) homolog subfamily C member 1 precursor | DNAJC1 | 0.002 0.72 | 60//82 |
| P197_BP4_885 (BAL) | Amyloid β A4 precursor protein-binding family B member 1-interacting protein | APBB1 | 0.007 0.79 | 75//82 |
| P51_BP4_577 (BAL) | Fibroblast growth factor binding protein 2 precursor | FGFBP-2 | 0.009 0.70 | 64//68 |
| Clone | Down-Regulated In Sarcoidosis vs Healthy Controls | Gene Name | q Value & AUC | Sensitivity & Specificity %, 95% CI |
| P197_BP4_755 (BAL) | SH3 domain-containing YSC84 like protein 1 | SH3YL1 | $1.0 \times 10^{-20}$ 0.77 | 65//82 |

Figure 4:
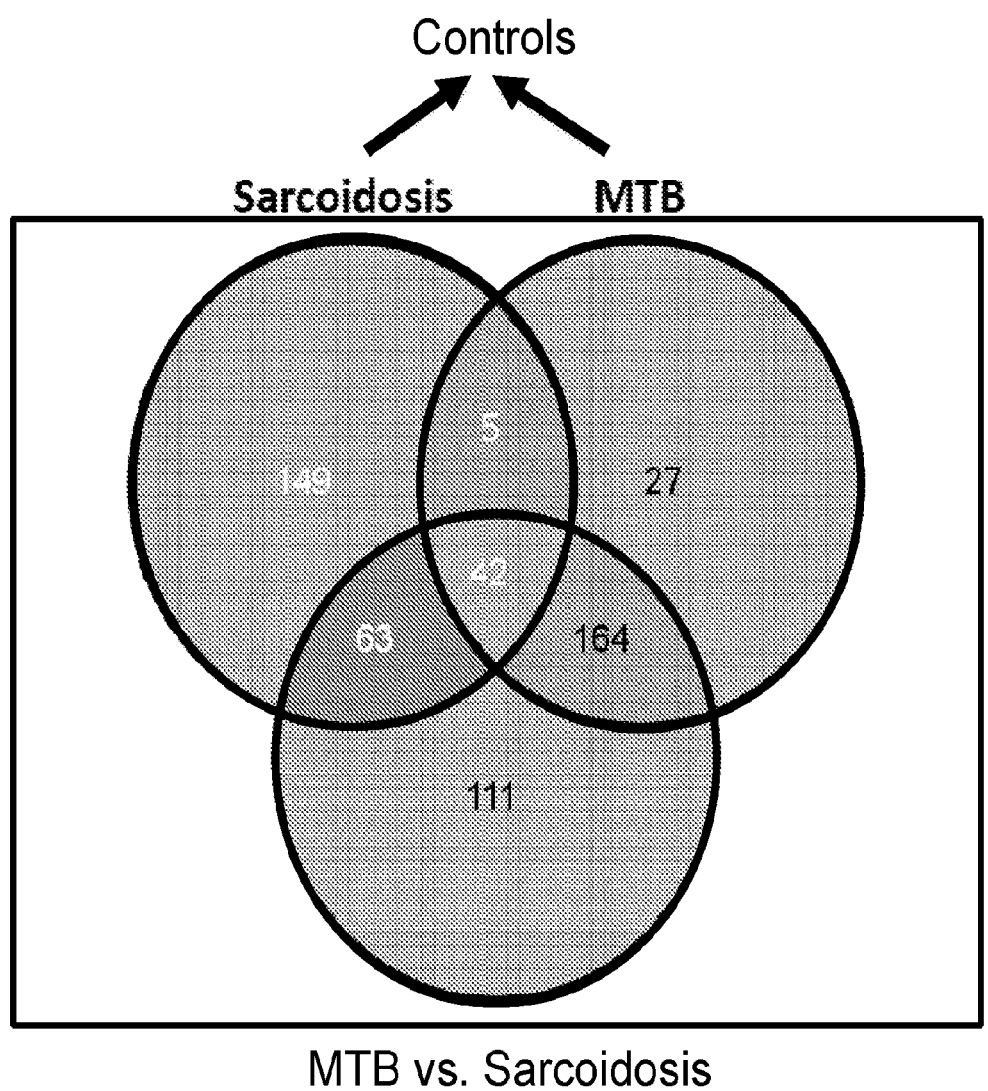
FIG. 4 shows a Venn diagram depicting differential phage clone significances among sarcoidosis, TB and healthy controls (q<0.01). The Venn diagram shows the overlap between 259 sarcoidosis clones and 238 TB clones as compared to healthy controls, as well as 380 TB clones versus sarcoidosis. Forty seven clones could differentiate both sarcoidosis and TB from healthy controls. Five clones could not discriminate between TB and sarcoidosis.
Figure 5A:
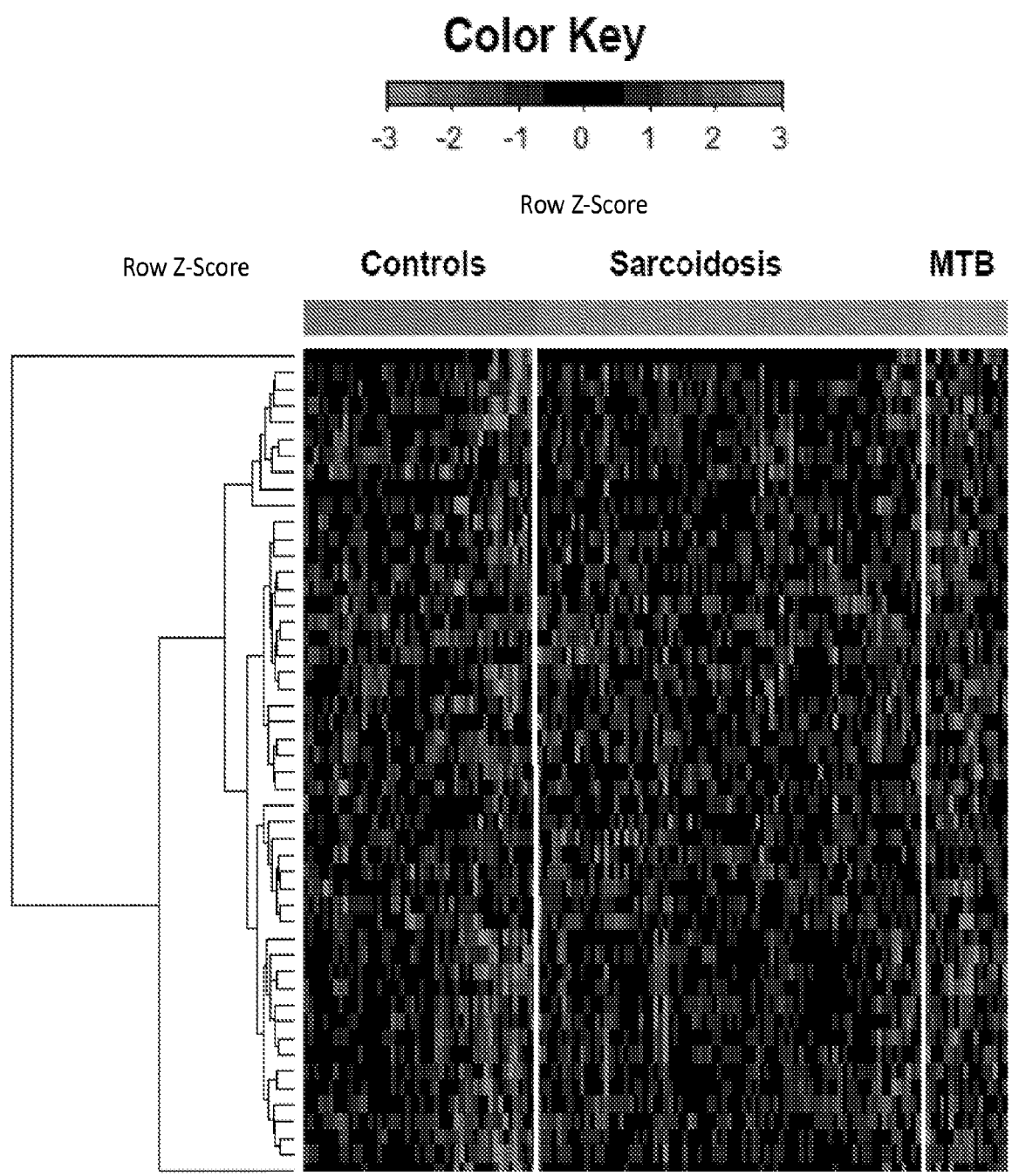
FIG. 5A shows a heatmap generated from a microarray analysis using 3 data sets derived from 115 sarcoidosis patients, 64 control subjects and 17 TB patients. Fifty antigens showed significant differential expression among the three groups.
Figure 5B:
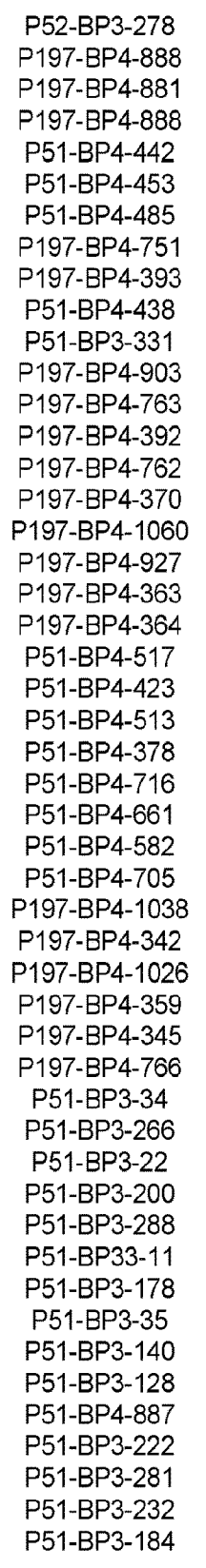

Complex sarcoidosis library detects novel antigens in the sera of tuberculosis patients. In view of the clinical and pathological similarities between MTB and sarcoidosis, a most useful clinical antigen(s) should discriminate between these two conditions. To this end, using the antigens identified by biopanning the CSL library a microarray was constructed, then this construct was interrogated with sera from 17 culture positive MTB subjects. Using a moderate t-test and a q value <0.05 in this system, 238 clones differentially expressed between TB and healthy controls and 380 clones differentially expressed between TB and sarcoidosis were identified. FIG. 4 shows a Venn diagram depicting the overlap between 259 sarcoidosis markers, 238 TB vs. control and 380 TB vs. sarcoidosis markers. Clearly, 47 clones differentiate both sarcoidosis and TB from healthy controls, while 5 of them cannot differentiate sarcoidosis from TB significantly. From these clones, 164 were found to be TB specific, and different from both healthy controls and sarcoidosis clones. FIG. 5 show the heatmap of 50 significant clones differentially expressed in all three groups. Similarly to the sarcoidosis antigens, the specificity and sensitivity of TB clones was analyzed to predict the presence of TB (Table 4). Finally, 10 TB antigens were sequenced and sequence homologies were searched using the same algorithm as previously described. Table 4 shows the 10 TB-specific antigens as compared to healthy controls as well as sarcoidosis.

| Clone | Up-Regulated in TB vs Sarcoidosis Subjects | Gene Name | q Value | AUC | Sensitivity// Specificity %, 95% Cl |
|---|---|---|---|---|---|
| P51_BP3_174 (MRC5) | Ferredoxin (Mycobacterium tuberculosis) | Fed A | $4.9 \times 10^{-15}$ | 0.87 | 88//83 |
| P51_BP4_610 (BAL) | WDFY3 protein (Homosapiens) | WDFY3 | $4.1 \times 10-12$ | 0.92 | 88//84 |
| P51_BP3_2 66 (EL-1) | Membrane protein (Mycobacterium tuberculosis) | MFS | $6.7 \times 10^{-10}$ | 0.9 | 82//93 |
| P51_BP3-166 (BAL) | Leucine rich PPR-motif containing protein (Homosapiens) | LRPPRC | $1.3 \times 10^{-9}$ | 0.81 | 71//90 |
| P51_BP4_704 (BAL) | HLA-DR alpha (Homosapiens) | HLA-DR | $1.1 \times 10^{-8}$ | 0.89 | 94//83 |
| P197_BP4_7 63 (BAL) | Transketolase (Mycobacterium tuberculosis) | TKT | $2.7 \times 10^{-8}$ | 0.86 | 82//76 |
| P51-BP4_563 (BAL) | Dihydroxy acid dehydratase (Mycobacterium tuberculosis) | Rv0189C | $1.04 \times 10^{-6}$ | 0.85 | 76//86 |
| Clone | Down-Regulated in TB vs Sarcoidosis Subjects | | | | |
| P51_BP3_1 13 (BAL) | Chain A Mycobacterium tuberculosis | BfrA | $1.2 \times 10^{-10}$ | 0.9 | 88//85 |
| P51_BP3_2 00 (BAL) | Disabled homolog 2 isoform 2 (Homosapiens) | DAB2 | $1.5 \times 10-9$ | 0.92 | 82//91 |
| P51_BP4_6 22 (BAL) | Transcription elongation factor B polypeptide 2 isoform (Homosapiens) | TCEB2 | $6.9 \times 10^{-7}$ | 0.89 | 82//89 |

After sequence analysis and homology search, one identical sequence between TB and sarcoidosis clone was identified. Although the identified clone's name was different: P51_BP3_287 versus P51_BP3_174, and they performed differently in sarcoidosis versus TB as indicated in q value (compare Table 3 and Table 4). However, using NCBI blast databases (*mycobacterium* toxoid and the universal blast) on the same sequence, two different proteins could be identified. FIG. 9 shows the full length of protein and genes of 10 TB antigens. Surprisingly, TB clones show much higher sensitivity and specificity; similarly the AUROC was larger for the majority of TB antigens (Table 4).

Discussion. The described work was inspired by the classic observation that the intradermal injection of a suspension of granulomatous splenic tissue (Kveim-Siltzbach test) induces granuloma formation weeks later in patients with sarcoidosis, suggesting the presence of antigen(s) in granuloma tissue and host immunoreactivity to those antigen(s). Kveim-like effects have also been observed using non-viable BAL cell extracts or PBMCs derived from sarcoidosis subjects. Several studies have attempted to identify specific antigens that can discriminate sarcoidosis from normal subjects or from patients with other granulomatous diseases such as TB (Hajizadeh et al., J. Clin. Immunol. 2007; 27(4): 445-54; Chen & Moller, Proc. Am. Thorac. Soc. 2007; 4(1): 101-7) but, most of these studies used limited proteomics or genomics to search for tissue antigens. Hajizadeh et al., J. Clin. Immunol. 2007; 27(4): 445-54; Richter et al., Am. J. Resp. Crit. Care 1999; 159(6): 1981-4; Song et al., The Journal of Experimental Medicine 2005; 201(5): 755-67. Here, using novel high throughput technology, the current gap was overcome by constructing phage-protein microarrays in which peptides derived from a unique sarcoidosis cDNA library were expressed as a sarcoidosis phage fusion protein. The phage-protein microarrays were screened to identify phage-peptide clones that bind antibodies in serum samples from patients with sarcoidosis but not in those from controls. Importantly, the same microarray constructs were immune-screened using sera of culture positive TB patients.

The average length of identified peptides for sarcoidosis antigens was between 9-130 amino acids (AA), while the average peptide length for TB antigens was 9-209 AA. Among 10 sarcoidosis specific phage peptides, 5 expression sequence tags with in frame epitopes were identified. Five other reactive antigens were relatively short out of frame peptides meeting the criteria to be considered as mimotopes (mimetic sequence of a true epitope). Similarly, among 10 sequenced TB specific phage peptides, 5 in frame epitopes with full length in frame proteins with homology to known human sequences were identified. Five other sequences were relatively short peptides with homology to various known MTB proteins (Table 4).

Interestingly, TB antigens had much higher specificity and sensitivity as compared to antigens selective to sarcoidosis as indicated by higher AUCs (Table 4). Although the significance of mimotopes is not clear, it has been shown that some out of frame peptides are immunogenic and can activate MHC class I molecules. Due to smaller peptide sequences of mimotopes, they may have homology with diverse proteins. Prior studies using similar techniques in various cancers had similarly identified out of frame peptides. Lin et al., Cancer epidemiology, biomarkers & prevention: a publication of the American Association for Cancer Research, cosponsored by the American Society of Preventive Oncology 2007; 16(11): 2396-405; Wang et al., Autoantibody signatures in prostate cancer. N. Engl. J. Med. 2005; 353(12): 1224-35; Chatterjee et al., Cancer Research 2006; 66(2): 1181-90. Detection of mimotopes in the described methods may be due to out of frame peptide synthesis secondary to altered ribosomal function, or may correspond to open reading frames, or generation of displayed peptides due to competition for binding during phage selection during phage insertion.

Although the primary goal was to identify the immune signature in sarcoidosis, a panel of antigens differentially expressed in sarcoidosis and tuberculosis as compared to healthy subjects was also identified. Tables 3 and 4 summarize the 10 most significant clones identified in sarcoidosis and tuberculosis respectively.

In recent years several groups have attempted to identify specific signatures to distinguish between tuberculosis and sarcoidosis using transcriptomics or gene expression profilings. Koth et al., Am. J. Resp. Crit. Care 2011; 184(10): 1153-63; Maertzdorf et al., Proc. Natl. Acad. Sci. USA 2012; 109(20): 7853-8; Berry et al., Nature 2010; 466(7309): 973-7. Yet most of these methods led to the discovery of a series of markers or expression signatures that failed to discriminate between these two diseases. Koth et al., American journal of respiratory and critical care medicine 2011; 184(10): 1153-63; Stone et al., PLoS One 2013; 8(1): e54487. This is partly due to the fact that several inflammatory or infectious diseases such as CD, lupus, sarcoidosis and tuberculosis may respond to various antigens with activation of similar transcriptomes and/or inflammatory gene expression profiles. For instance, Maertzdorf et al. found more similarity in the activated pathways than differences between sarcoidosis and MTB. Proc. Natl. Acad. Sci. USA 2012; 109(20): 7853-8. Their results in sarcoidosis were similar to those results by Berry indicating the importance of the interferon pathway (IFN) signature in MTB. Maertzdorf et al., Proc. Natl. Acad. Sci. USA 2012; 109(20): 7853-8; Berry et al., Nature 2010; 466(7309): 973-7. In addition, considerable pathway overlap was identified between lupus, sarcoidosis and TB. Maertzdorf et al., Proc. Natl. Acad. Sci. USA 2012; 109(20): 7853-8. However, despite similar genetic or transcriptomic signatures, these diseases are clinically entirely different and require different therapy. Tuberculosis, a global infectious disease caused by the intracellular bacterium *Mycobacterium tuberculosis* remains a worldwide health problem (http:www.who.int). One barrier for eradication of tuberculosis besides the lack of effective vaccination is the lack of reliable antigen to evaluate the activity of the disease and its response to treatment. Nahid et al., Am. J. Resp. Crit. Care 2011. 184(8): 972-9. Standard methods to diagnose TB and to monitor response to treatment rely on sputum microscopy and culture. The current CDC/NIH roadmap emphasizes the need for development of new TB antigens as alternative methods. Nahid et al., Am. J. Resp. Crit. Care e 2011. 184(8): 972-9. In view of this background, perhaps surprisingly, the described microarray platform could discriminate tuberculosis from sarcoidosis and healthy controls. In addition to antigens for sarcoidosis, more than 300 clones specifically for tuberculosis were detected. Interestingly, a considerable number of these clones were TB specific and related to bacterial growth of *Mycobacterium tuberculosis*, and its metabolism (Table 4). Recently a tremendous effort has been put toward elucidating the antibody response to MTB antigens, which has implications for the development of new antigens to diagnose and monitor successful treatment, as well as to develop effective vaccination. Kunnath-Velayudhan et al., Proc. Natl. Acad. Sci. USA 2010; 107(33): 14703-8. Yet, a consistent immune response to MTB has not been found. Most other studies searching for antigens in TB have identified unspecific markers primarily involving host response such as C-reactive protein or serum amyloid A and others, but not MTB specific antigens. Agranoff et al., Lancet 2006; 368(9540): 1012-21; De Groote et al., PLoS One 2013; 8(4): e61002. MTB has the ability to survive within host macrophages, largely escaping immune surveillance and maintaining its ability for replication and person to person transmission. Meena & Rajni, The FEBS journal 2010; 277(11): 2416-27.

The primary goal of the described project was to discover antigens related to sarcoidosis. Yet, in addition specific antigens for TB were detected. These results are surprising, as the question remains, how can the sarcoidosis library detect TB specific antigens? Lungs are environmentally highly exposed to numerous bacteria, and the described library is predominantly derived from BAL cells that contain all types of immune cells, including macrophages that might have integrated messages from MTB. Without being bound by theory, this could be the reason why the CSL was able to detect TB specific antigens. Still, the major question is why BAL cells of patients with sarcoidosis can harbor MTB messages, yet respond to PPD skin testing with anergy, as all donors with sarcoidosis were PPD negative.

Similar to gene-expression profiling and the pattern-recognition approaches utilizing serum proteomics, the described methods may have the limitations of background signals, and sample-selection bias. To minimize these problems, an integrative-analysis method, an adaptively-weighted statistical method on two sets of data acquired in two independent experiments was applied. The discriminatory power of antibody signatures was validated by analyzing data from two completely different cohorts of patients.

In summary, a novel T7 phage display library derived from macrophages from BAL, monocytes from blood leukocytes of patients with sarcoidosis that may display a significant segment of the universe of potential sarcoidosis and MTB antigens that can be specially recognized by high IgG antibodies in sarcoidosis and MTB sera was developed. The described results support the hypothesis that sarcoidosis sera can recognize antigens presented in sarcoidosis materials. Current study of the antibody response can advance how proteomics can be used to harness immunity to identify and treat diseases, because it investigates antibody-antigen interactions and also evaluates the effects on antibody responses of pathogen and host characteristics.

Standard reference works setting forth the general principles of immunology include Abbas et al., Cellular and Molecular Immunology (6th Ed.), W.B. Saunders Co., Philadelphia, 2007; Janeway et al., Immunobiology. The Immune System in Health and Disease, 6th ed., Garland Publishing Co., New York, 2005; Delves et al. (eds.) Roitt's Essential Immunology (11th ed.) Wiley-Blackwell, 2006; Roitt et al., Immunology (7th ed.) C. V. Mosby Co., St. Louis, Mo. (2006); Klein et al., Immunology (2nd ed), Blackwell Scientific Publications, Inc., Cambridge, Mass., (1997).

Additionally, methods particularly useful for polyclonal and monoclonal antibody production, isolation, characterization, and use are described in the following standard references: Harlow et al., Antibodies: A Laboratory Manual, Cold Spring Harbor Laboratory Press, Cold Spring Harbor, N.Y., 1988); Harlow et al., Using Antibodies: A Laboratory Manual, Cold Spring Harbor Laboratory Press, Cold Spring Harbor Laboratory Press, Cold Spring Harbor, N.Y., 1998; Monoclonal Antibodies and Hybridomas: A New Dimension in Biological Analyses, Plenum Press, New York, N.Y. (1980); Zola et al., in Monoclonal Hybridoma Antibodies: Techniques and Applications, CRC Press, 1982).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the ability to diagnose a sarcoidosis subject from a healthy subject or a sarcoidosis subject from a tuberculosis subject.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method, comprising
obtaining a sample from a subject; and
assaying the sample for
Ferredoxin (FedA); Transketolase (TKT); and Dihydroxy acid dehydratase (Rv0189C).

2. The method of claim 1, wherein the sample is a tissue sample, a cell sample, a whole blood sample, a serum sample, a plasma sample, a saliva sample, a sputum sample, or a urine sample; and/or
assaying the sample for one or more markers comprises contacting the sample with a probe comprising a detectable label and that binds the one or more markers; and/or
wherein obtaining a value based on the assay comprises quantitating the amount of the marker in the sample; and/or
the value is a score or a weighted score.

3. The method according to claim 1, wherein assaying the sample for one or more markers comprises contacting the sample with a probe comprising a detectable label and that binds the one or more markers.

4. The method according to claim 1, wherein obtaining a value based on the assay comprises quantitating the amount of the marker in the sample.

5. The method according to claim 1, wherein the value is a score.

6. The method according to claim 5 wherein the score is a weighted score.

7. The method of claim 1, wherein the sample is further assayed for one or more markers selected from Small inducible cytokine A21 precursor (CCL21); Methionine aminopeptidase 1 (Metap1); Activated RNA polymerase II transcription cofactor variant 4 (PC4); RNA methyltransferase (CLI_3190); Tumor necrosis factor receptor superfamily member 21 precursor (TNFRSF21); Monocyte differentiation antigen CD14 (CD14); DnaJ (Hsp40) homolog subfamily C member 1 precursor (DNAJC1); Amyloid β A4 precursor protein-binding family B member 1-interacting protein (APBB1); Fibroblast growth factor binding protein 2 precursor (FGFBP-2); or SH3 domain-containing YSC84 like protein 1 (SH3YL1).

8. The method of claim 7, further comprising:
obtaining a value based on the assay;
comparing the value to a reference level;
diagnosing the subject as having tuberculosis based on the upregulation of one or more of FedA, TKT, and/or Rv0189C, as demonstrated by the value and the reference level; and
treating the subject diagnosed as having tuberculosis with a tuberculosis treatment comprising one or more of isoniazid (INH), rifampin (RIF), ethambutol (EMB), or pyrazinamide (PZA).

9. The method of claim 1, wherein the sample is further assayed for one or markers selected from WDFY3; MFS; LRPPRC; HLA-DR; BfrA; DAB2; or TCEB2.

10. The method of claim 9, further comprising:
obtaining a value based on the assay;
comparing the value to a reference level;
diagnosing the subject as having tuberculosis based on the upregulation of one or more of FedA, WDFY3, MFS, LRPPRC, HLA-DR, TKT, and/or Rv0189C, or the downregulation of the one or more of BfrA, DAB2, and/or TCEB2, as demonstrated by the value and the reference level; and
treating the subject diagnosed as having tuberculosis with a tuberculosis treatment comprising one or more of isoniazid (INH), rifampin (RIF), ethambutol (EMB), or pyrazinamide (PZA).

11. The method of claim 1, further comprising:
obtaining a value based on the assay;
comparing the value to a reference level;

diagnosing the subject as having tuberculosis based on the upregulation of one or more of FedA, TKT, and/or Rv0189C, as demonstrated by the value and the reference level; and treating the subject diagnosed as having tuberculosis with a tuberculosis treatment comprising one or more of isoniazid (INH), rifampin (RIF), ethambutol (EMB), or pyrazinamide (PZA).

12. A method of diagnosing a subject as having sarcoidosis rather than tuberculosis and treating sarcoidosis in the subject, the method comprising:
obtaining a sample derived from the subject;
assaying the sample for Ferredoxin (FedA), Transketolase (TKT), and Dihydroxy acid dehydratase (Rv01890);
obtaining a value based on the assay;
comparing the value to a reference level;
diagnosing the subject as having sarcoidosis rather than tuberculosis based on the up- or down-regulation of the one or more markers as demonstrated by the value and the reference level; and
treating the subject diagnosed as having sarcoidosis with a sarcoidosis treatment comprising one or more of a corticosteroid, methotrexate, azathioprine, hydroxychloroquine, chloroquine, cyclophosphamide, chlorambucil, pentoxifylline and thalidomide, infliximab, adalimumab, colchicine, a nonsteroidal anti-inflammatory drug (NSAID), and/or organ transplantation.

13. The method of claim 12, comprising further assaying the sample for one or more markers selected from WDFY3 protein (WDFY3); Membrane protein (MFS); Leucine rich PPR-motif containing protein (LRPPRC); HLA-DR alpha (HLA-DR); Chain A *Mycobacterium* tuberculosis (BfrA); Disabled homolog 2 isoform 2 (DAB2); Transcription elongation factor B polypeptide 2 isoform (*Homo sapiens*) (TCEB2); Small inducible cytokine A21 precursor (CCL21); Methionine aminopeptidase 1 (Metap1); Activated RNA polymerase II transcription cofactor variant 4 (PC4); RNA methyltransferase (CLI_3190); Tumor necrosis factor receptor superfamily member 21 precursor (TNFRSF21); Monocyte differentiation antigen CD14 (CD14); DnaJ (Hsp40) homolog subfamily C member 1 precursor (DNAJC1); Amyloid β A4 precursor protein-binding family B member 1-interacting protein (APBB1); Fibroblast growth factor binding protein 2 precursor (FGFBP-2); or SH3 domain-containing YSC84 like protein 1 (SH3YL1).

* * * * *

UNITED STATES PATENT AND TRADEMARK OFFICE
CERTIFICATE OF CORRECTION

PATENT NO. : 10,781,489 B2
APPLICATION NO. : 15/555419
DATED : September 22, 2020
INVENTOR(S) : Lobelia Samavati et al.

Page 1 of 1

It is certified that error appears in the above-identified patent and that said Letters Patent is hereby corrected as shown below:

In the Specification

In Column 1, Line 18, change "HL104481awarded" to --HL104481 awarded"--.

In the Claims

In Column 151, Line 14, Claim 12, change "Rv01890" to --Rv0189C--.

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 77

<210> SEQ ID NO 1
<211> LENGTH: 14
<212> TYPE: DNA
<213> ORGANISM: Artificial Sequence
<220> FEATURE:
<223> OTHER INFORMATION: BAL: EcoRI/HindIII linkers

<400> SEQUENCE: 1
gcttgaattc aagc                                                    14

<210> SEQ ID NO 2
<211> LENGTH: 20
<212> TYPE: DNA
<213> ORGANISM: Artificial Sequence
<220> FEATURE:
<223> OTHER INFORMATION: WBC: ALA modified linkers

<400> SEQUENCE: 2
gcttgctgaa ttcagcaagc                                              20

<210> SEQ ID NO 3
<211> LENGTH: 19
<212> TYPE: DNA
<213> ORGANISM: Artificial Sequence
<220> FEATURE:
<223> OTHER INFORMATION: MRC5: LEU modified linkers

<400> SEQUENCE: 3
gcttagtgaa ttcactaag                                               19

<210> SEQ ID NO 4
<211> LENGTH: 20
<212> TYPE: DNA
<213> ORGANISM: Artificial Sequence
<220> FEATURE:
<223> OTHER INFORMATION: EL-1: THR modified linkers

<400> SEQUENCE: 4
gcttcttgaa ttcaacaagc                                              20

<210> SEQ ID NO 5
<211> LENGTH: 9
<212> TYPE: PRT
<213> ORGANISM: Artificial Sequence
<220> FEATURE:
<223> OTHER INFORMATION: P51BP3_287

<400> SEQUENCE: 5

Ile Gln His Gln His Leu Gly Gln Ile
1               5

<210> SEQ ID NO 6
<211> LENGTH: 110
<212> TYPE: PRT
<213> ORGANISM: Osmerus mordax

<400> SEQUENCE: 6

Met Ala Ala Val Tyr Lys Leu Leu Phe Cys Gly Leu Leu Cys Phe
1               5                   10                  15

Leu Thr Val Thr Gln Gly Gln Met Val Val Asp Cys Cys Leu Lys Val
                20                  25                  30

Ser Asp Arg Glu Ile Pro Arg Gln Leu Val Arg Ser Tyr Gln His Gln
            35                  40                  45

-continued

```
His Leu Gly Gln Gly Cys Ser Leu Asp Ala Val Ile Phe Val Thr Lys
    50                  55                  60

Lys Asn Arg Phe Leu Cys Ala Thr Pro Gly Gln Pro Trp Val Arg Asp
 65                  70                  75                  80

Leu Ile Asn His Val Asp His Leu Thr Lys Lys Cys Arg Ser Ser Asn
                 85                  90                  95

Phe Gln Gly Lys Arg Cys Arg Gly Leu Lys Pro Gln Ala Val
            100                 105                 110

<210> SEQ ID NO 7
<211> LENGTH: 335
<212> TYPE: PRT
<213> ORGANISM: Listeria monocytogenes

<400> SEQUENCE: 7

Met Leu Leu Asn Glu Glu Pro Glu Val Lys Glu Leu Leu Leu Ala
 1               5                  10                  15

Thr Thr Ser Thr Leu Thr Asn Gln Asp Leu Thr Asp Asn Glu Glu Ile
                 20                  25                  30

Lys Tyr Leu Phe Asn Asn Asp Lys Thr Val Asn Arg Lys Leu Gln Asp
             35                  40                  45

Gln Val Ile Asn Leu Tyr Asp Lys Asp Gly His Phe Ile Asn Lys Tyr
     50                  55                  60

Tyr Phe Ser Arg Ser Gln Asp Ile Thr Ser Ile Asp Phe Ser Gln Tyr
 65                  70                  75                  80

Phe Val Ser Gly Thr Asp Lys Phe Ile Met Asn Lys Pro Thr Ile Asp
                 85                  90                  95

Gly Gln Lys Met Met Thr Ala Gln Met Pro Ile Val Ala Asp Asp Asn
            100                 105                 110

Thr Thr Val Ile Gly Tyr Ala Gln Val Val Asn Pro Leu Thr Ser Tyr
        115                 120                 125

Asn Arg Met Met Asp Arg Leu Leu Val Thr Met Ile Leu Leu Gly Ala
    130                 135                 140

Val Ala Leu Phe Ile Ser Gly Met Leu Gly Tyr Leu Leu Ala Gln Asn
145                 150                 155                 160

Phe Leu Asn Pro Leu Thr Arg Leu Ala Arg Thr Met Asn Asp Ile Arg
                165                 170                 175

Lys Asn Gly Phe Gln Lys Arg Ile Glu Thr Lys Thr Asn Ser Arg Asp
            180                 185                 190

Glu Ile Gly Glu Leu Thr Val Val Phe Asn Asp Met Met Thr Arg Ile
        195                 200                 205

Glu Thr Ser Phe Glu Gln Gln Lys Gln Phe Val Glu Asp Ala Ser His
    210                 215                 220

Glu Leu Arg Thr Pro Val Gln Ile Met Glu Gly His Leu Lys Leu Leu
225                 230                 235                 240

Thr Arg Trp Gly Lys Asp Asp Pro Ala Val Leu Asp Glu Ser Leu Asn
                245                 250                 255

Ala Ser Leu Thr Glu Leu Glu Arg Met Lys Lys Leu Val Gln Glu Met
            260                 265                 270

Leu Asp Leu Ser Arg Ala Glu Gln Ile Ser Gln Thr Lys Glu Leu Gln
        275                 280                 285

Ile Thr Asp Val Asn Ala Thr Val Glu Gln Val Arg Arg Asn Phe Glu
    290                 295                 300

Val Met Tyr Glu Asn Phe Thr Phe Thr Leu Lys Glu Asp Asp Thr Asp
```

```
            305                 310                 315                 320
Leu Arg Ala Leu Ile Gln His Asn His Leu Glu Gln Ile Leu Ile
                    325                 330                 335

<210> SEQ ID NO 8
<211> LENGTH: 7
<212> TYPE: PRT
<213> ORGANISM: Artificial Sequence
<220> FEATURE:
<223> OTHER INFORMATION: Region of similarity between P51BP3_287 and
      small inducible cytokine A21 precursor

<400> SEQUENCE: 8

Gln His Gln His Leu Gly Gln
1               5

<210> SEQ ID NO 9
<211> LENGTH: 9
<212> TYPE: PRT
<213> ORGANISM: Artificial Sequence
<220> FEATURE:
<223> OTHER INFORMATION: Region of similarity between P51BP3_287 and
      sensor histidine kinase, partial
<220> FEATURE:
<221> NAME/KEY: Xaa
<222> LOCATION: (4)..(4)
<223> OTHER INFORMATION: Xaa denotes a region of non-similarity
<220> FEATURE:
<221> NAME/KEY: Xaa
<222> LOCATION: (7)..(7)
<223> OTHER INFORMATION: Xaa denotes a region of non-similarity

<400> SEQUENCE: 9

Ile Gln His Xaa His Leu Xaa Gln Ile
1               5

<210> SEQ ID NO 10
<211> LENGTH: 16
<212> TYPE: PRT
<213> ORGANISM: Artificial Sequence
<220> FEATURE:
<223> OTHER INFORMATION: P51BP3_281

<400> SEQUENCE: 10

Ala Gly Ile Ser Arg Glu Leu Val Asp Lys Leu Ala Ala Ala Leu Glu
1               5                   10                  15

<210> SEQ ID NO 11
<211> LENGTH: 326
<212> TYPE: PRT
<213> ORGANISM: Homo sapiens

<400> SEQUENCE: 11

Met Tyr Arg Tyr Thr Gly Lys Leu Arg Pro His Tyr Pro Leu Met Pro
1               5                   10                  15

Thr Arg Pro Val Pro Ser Tyr Ile Gln Arg Pro Asp Tyr Ala Asp His
                20                  25                  30

Pro Leu Gly Met Ser Glu Ser Glu Gln Ala Leu Lys Gly Thr Ser Gln
        35                  40                  45

Ile Lys Leu Leu Ser Ser Glu Asp Ile Glu Gly Met Arg Leu Val Cys
    50                  55                  60

Arg Leu Ala Arg Glu Val Leu Asp Val Ala Ala Gly Met Ile Lys Pro
65                  70                  75                  80

Gly Val Thr Thr Glu Glu Ile Asp His Ala Val His Leu Ala Cys Ile
                85                  90                  95
```

```
Ala Arg Asn Cys Tyr Pro Ser Pro Leu Asn Tyr Tyr Asn Phe Pro Lys
            100                 105                 110

Ser Cys Cys Thr Ser Val Asn Glu Val Ile Cys His Gly Ile Pro Asp
            115                 120                 125

Arg Arg Pro Leu Gln Glu Gly Asp Ile Val Asn Val Asp Ile Thr Leu
130                 135                 140

Tyr Arg Asn Gly Tyr His Gly Asp Leu Asn Glu Thr Phe Phe Val Gly
145                 150                 155                 160

Glu Val Asp Asp Gly Ala Arg Lys Leu Val Gln Thr Thr Tyr Glu Cys
                165                 170                 175

Leu Met Gln Ala Ile Asp Ala Val Lys Pro Gly Val Arg Tyr Arg Glu
            180                 185                 190

Leu Gly Asn Ile Ile Gln Lys His Ala Gln Ala Asn Gly Phe Ser Val
            195                 200                 205

Val Arg Ser Tyr Cys Gly His Gly Ile His Lys Leu Phe His Thr Ala
210                 215                 220

Pro Asn Val Pro His Tyr Ala Lys Asn Lys Ala Val Gly Val Met Lys
225                 230                 235                 240

Ser Gly His Val Phe Thr Ile Glu Pro Met Ile Cys Glu Gly Gly Trp
                245                 250                 255

Gln Asp Glu Thr Trp Pro Asp Gly Trp Thr Ala Val Thr Arg Asp Gly
            260                 265                 270

Lys Arg Ser Ala Gln Phe Glu His Thr Leu Leu Val Thr Asp Thr Gly
            275                 280                 285

Cys Glu Ile Leu Thr Arg Arg Leu Asp Ser Ala Arg Pro His Phe Met
290                 295                 300

Ser Gln Phe Glu Phe Glu Leu Val Asp Lys Leu Ala Ala Ala Leu Glu
305                 310                 315                 320

His His His His His His
                325

<210> SEQ ID NO 12
<211> LENGTH: 11
<212> TYPE: PRT
<213> ORGANISM: Artificial Sequence
<220> FEATURE:
<223> OTHER INFORMATION: Region of Similarity between P51BP3_281 and
      Chain A, Human Metap1 With Bengamide Analog Y16, In Mn Form

<400> SEQUENCE: 12

Glu Leu Val Asp Lys Leu Ala Ala Ala Leu Glu
1               5                   10

<210> SEQ ID NO 13
<211> LENGTH: 42
<212> TYPE: PRT
<213> ORGANISM: Artificial Sequence
<220> FEATURE:
<223> OTHER INFORMATION: P51BP4_388

<400> SEQUENCE: 13

Ser Glu Tyr Trp Met Asp Pro Glu Gly Glu Met Lys Pro Gly Arg Lys
1               5                   10                  15

Gly Ile Ser Leu Asn Pro Glu Gln Trp Ser Gln Leu Lys Glu Gln Ile
            20                  25                  30

Ser Asp Ile Asp Asp Ala Val Arg Lys Leu
            35                  40
```

<210> SEQ ID NO 14
<211> LENGTH: 132
<212> TYPE: PRT
<213> ORGANISM: Homo sapiens

<400> SEQUENCE: 14

```
Glu Pro Ser Glu Ala Met Pro Lys Ser Lys Glu Leu Val Ser Ser Ser
1               5                   10                  15

Ser Ser Gly Ser Asp Ser Asp Ser Glu Val Asp Lys Lys Leu Lys Arg
            20                  25                  30

Lys Lys Gln Val Ala Pro Glu Lys Pro Val Lys Gln Lys Thr Gly
        35                  40                  45

Glu Thr Ser Arg Ala Leu Ser Ser Ser Lys Gln Ser Ser Ser Ser Arg
    50                  55                  60

Asp Asp Asn Met Phe Gln Ile Gly Lys Met Arg Tyr Val Ser Val Arg
65                  70                  75                  80

Asp Phe Lys Gly Lys Val Leu Ile Asp Ile Arg Glu Tyr Trp Met Asp
                85                  90                  95

Pro Glu Gly Glu Met Lys Pro Gly Arg Lys Gly Ile Ser Leu Asn Pro
            100                 105                 110

Glu Gln Trp Ser Gln Leu Lys Glu Gln Ile Ser Asp Ile Asp Asp Ala
        115                 120                 125

Val Arg Lys Leu
    130
```

<210> SEQ ID NO 15
<211> LENGTH: 41
<212> TYPE: PRT
<213> ORGANISM: Artificial Sequence
<220> FEATURE:
<223> OTHER INFORMATION: Region of similarity between P21BP4_388 and
      activated RNA polymerase II transcription cofactor 4 variant

<400> SEQUENCE: 15

```
Glu Tyr Trp Met Asp Pro Glu Gly Glu Met Lys Pro Gly Arg Lys Gly
1               5                   10                  15

Ile Ser Leu Asn Pro Glu Gln Trp Ser Gln Leu Lys Glu Gln Ile Ser
            20                  25                  30

Asp Ile Asp Asp Ala Val Arg Lys Leu
        35                  40
```

<210> SEQ ID NO 16
<211> LENGTH: 19
<212> TYPE: PRT
<213> ORGANISM: Artificial Sequence
<220> FEATURE:
<223> OTHER INFORMATION: P51BP4_596

<400> SEQUENCE: 16

```
Ser Glu Asn Thr Lys Ile Ser Arg Val Lys Leu Ala Gly Arg Gly Gly
1               5                   10                  15

Val Cys Leu
```

<210> SEQ ID NO 17
<211> LENGTH: 261
<212> TYPE: PRT
<213> ORGANISM: Clostridium botulinum

<400> SEQUENCE: 17

```
Met Asn Leu Ile Glu Ser Lys Asp Asn Thr Leu Ile Lys Tyr Val Arg
```

```
              1               5              10              15
            Lys Leu Arg Lys Lys Lys Tyr Arg Val Gln Glu Glu Lys Phe Leu Val
                            20                  25                  30

Glu Gly Phe Arg Phe Val Glu Glu Ala Leu Lys Ser Thr Phe Lys Ile
                            35                  40                  45

Ser His Val Leu Val Gly Glu Ser Ala Lys Glu Lys Cys Asn Ser Phe
                            50                  55                  60

Asn Ile Phe Asn Ile Val Ser Glu Asn Thr Lys Ile Ser Leu Val Lys
             65                  70                  75                  80

Asp Glu Ile Leu Lys Glu Leu Cys Gly Thr Asn Asn Pro Gln Gly Ile
                            85                  90                  95

Ile Ala Ile Val Asp Asn Lys Ile Ile Asn Ile Glu Asp Lys Ser Gly
                            100                 105                 110

Phe Tyr Val Leu Ala Asp Lys Val Gln Asp Pro Gly Asn Met Gly Thr
                            115                 120                 125

Ile Ile Arg Ser Ala Asn Ala Ser Gly Ala Leu Gly Val Ile Val Thr
                            130                 135                 140

Lys Gly Thr Val Asp Ile Tyr Asn Asp Lys Thr Leu Arg Ser Thr Met
            145                 150                 155                 160

Gly Ser Ile Phe Lys Ile Pro Ile Ile Glu Asp Asn Glu Phe Glu Ile
                            165                 170                 175

Ile Asn Val Leu Lys Ser Lys Gly Phe Lys Leu Ile Val Ser Ser Leu
                            180                 185                 190

Asp Thr Glu Asn Asn Phe Phe Asp Ile Asp Leu Thr Gly Lys Val Ile
                            195                 200                 205

Ile Cys Val Gly Asn Glu Gly Asn Gly Val Ser Asp Glu Val Tyr Ser
                            210                 215                 220

Leu Gly Asp Glu Lys Val Lys Ile Pro Met Pro Gly Asn Ala Glu Ser
            225                 230                 235                 240

Leu Asn Ala Gly Val Ala Ala Ser Ile Met Met Tyr Glu Val Val Arg
                            245                 250                 255

Gln Asn His Asn Lys
                            260

<210> SEQ ID NO 18
<211> LENGTH: 177
<212> TYPE: PRT
<213> ORGANISM: Homo sapiens

<400> SEQUENCE: 18

Met Gly Ile Asn Glu Cys Gln Tyr Gln Phe Arg Phe Gly Arg Trp Asn
            1               5                   10                  15

Cys Ser Ala Leu Gly Glu Lys Thr Val Phe Gly Gln Glu Leu Arg Val
                            20                  25                  30

Gly Ser Arg Glu Ala Ala Phe Thr Tyr Ala Ile Thr Ala Ala Gly Val
                            35                  40                  45

Ala His Ala Val Thr Ala Ala Cys Ser Gln Gly Asn Leu Ser Asn Cys
                            50                  55                  60

Gly Cys Asp Arg Glu Lys Gln Gly Tyr Tyr Asn Gln Ala Glu Gly Trp
            65                  70                  75                  80

Lys Trp Gly Gly Cys Ser Ala Asp Val Arg Tyr Gly Ile Asp Phe Ser
                            85                  90                  95

Arg Arg Phe Val Asp Ala Arg Glu Ile Lys Lys Asn Ala Arg Arg Leu
                            100                 105                 110
```

```
Met Asn Leu His Asn Asn Glu Ala Gly Arg Lys Val Ala Gly Arg Gly
        115                 120                 125

Gly Ser Arg Leu Gln Ser Gln His Phe Gly Arg Pro Arg Arg Ala Asp
    130                 135                 140

Gln Leu Arg Ser Gly Ile Arg Asp Gln Pro Glu Gln His Gly Glu Thr
145                 150                 155                 160

Pro Ser Leu Pro Lys Thr Gln Lys Leu Ala Gly Arg Gly Gly Thr Cys
                165                 170                 175

Leu

<210> SEQ ID NO 19
<211> LENGTH: 32767
<212> TYPE: DNA
<213> ORGANISM: Homo sapiens

<400> SEQUENCE: 19
agccagccac catgcctggc tctaagtttc cttttttctc tctctttata attttattat      60
tattactatt atttggagaa aggatctcac cctgtcgccc aggctggagt gtagtggcat     120
aatcatggct cactgtagcc tcaacctctc caggctcagg tgatcctccc acctcagcct     180
cctgagtagt tgggactaca ggcatacgtc accatgccaa gctaattttt gtattttttg     240
tagggacggg ttctcactat gttgctcagg ttggtctcaa actcctgagc tgaagtgatc     300
tgcccacctt ggcctcccaa actgctggca ttacaggtat gagccaccag gcccggcctt     360
tttaattttt taatttttat tttttataga gacagggtct tgctatgttg accaggttgc     420
tctctgtctc ctggcctcat gcaatcctct cacctcagcc tttcaaagta ctgggattat     480
aggcatgtgc caccacacct ggcctagtgt tcttttatttc tttttctttt ttttttcttt    540
gaggtagggt cttacttcct tgcccaggc tagaagtgca gtggcttgat ctcagctcat     600
tgcagcgtca acttcccagg caaacatgat cttcccacct cagcttccct agtggctggg    660
attacaggca caagccacca cacacagcta atttttttt tattattaca ttttaatag      720 agacggagtt ttgtcacatt gtccaggctg gtctcaaact cctgagctca agggacccac    780
ccaccatgcc ctcccaaggg gctaggatta catgcaagag ccaccgcacc cggttcaagt    840
tttctttctt gagcattatt tattttattt cattttattt tttgagatgg agtcttgctc    900
tggtgcccag gctggagtac agtggaatga tcttggctca ctgcaaccccc tccgccttcc    960 gggttcaagt gattctcctg cctcagtctc ctgagtagct gggattacag acgtgcacct   1020
ggctaatttt tgtattttttg gtagagacgg tgtttcacca tgttggccag gctggttttg   1080
aactcctgac cacaggtgat ccgcccacct cggcctccca aagtgctggg attacaggcg   1140
tgagccactg cgcctgtcct acttgagcat tatctttaac aggtaagaaa atcaatactt   1200
aaaaaaaaat ttttttggct cagcttcgca atttgggcag atgggaaaaa aagtcttgag   1260
gaggctaagt tcagtaaatg ataaaaggca gtaaaacaga gatgcagagg gtggtggcag   1320
ctggcattga gaaccagcaa cactggctga aaaggaagct gtgaagagat gtaaaaacca   1380
caggtgaatg ctgccagaaa taaaattgcc cagcttgcct ggctgggtgg aaggtaaata   1440
gataaggtca gggaaagctt gctgggctta ttcaaggtca ttgggcagtg ggccttaaat   1500
taattgatct tattgttttt tctagtccta accatactga gattgacttt agaagagggc   1560
agcttgagca gtcatttctc tcactatggc cagagtccag ggcctgtgtc cagtgggtgt   1620
tggttcccag gctgtggaat tatgatgaa aaggatcgtt aggactgtaa gaggagttaa    1680
atgaagtggc aaactggaaa gagcctatac tttggagcga gggagcactg cctttgaatc    1740
```

```
ctctctctgt cccttaccag ccatgttgac cctgaacaag taactaatga cctagcgcaa    1800
gatcaaaggc cccttgaaag tagggaatta gggaaaatat aataagtatg caataaatt     1860 atacttttta acaaacaaaa acagaaaata aaagttctgg atgggtgcgg tggctcatgc    1920
ctgtaatctg agcactttgg gaggccaagg cacttgaggt caggagttca ctgatcactt    1980
gaggtcagga gttcaaagcc agcctggcca acatggtgaa accccgtctc tactaaaaat    2040
acaaaaaaat tagttgggcg tcgtggcggg tgcctataat cccagctact caggaggctg    2100
aggcaggaga atcgcttgaa cccgggaggc agaggtttgc agtgagccca gattgcacca    2160
ctgcactcca ccctgggcca cagagcaaga ctctgtctca aaaaaatta aaattaaaat     2220 taaaataaaa aaatgaaatt aaaaaactaa aaattcttaa aagcagctgc tttgaacaaa    2280
cacagttgat taaactaaaa accctgctat aacaccttct attgtccagg aaaccttgat    2340
gtcagggcag gtttccccac aggtcttata aacacaagtt tttaaatcag ccatttctga    2400
cttgagatta agtctttcat acatatgcta tttgttttct tatcccgttt tggtttcgca    2460
agtcttggca actgtcaggt cttttcacaa agttctctag tgtttgaggg cattttttg    2520 gggggcctgg ccttgtgtgc agatggaaaa caactctttt ttttttttt ttttgagat     2580 agagtttcac ttttgtctcc caggctatgg ctcacttcaa cctccacctc ccaggttcaa    2640
gcgattctcc tgcctcagcc tcctgagtag ctgggattac aggcggctgc caccacgccc    2700
ggctaatttt tttttttttt ttttgagac ggagtctcgc tctgttgccc aggctggagt     2760
gcagtggcgc gatccaagct cactgcaacc tccgcctccc aggttcaagc aattctctgc    2820
ctcagcctct caagtagctg ggattacagg tgcctgctac gatgcccagc taattgtttt    2880
gtatttttag tagagacggg tttcatcatg ttggccagac tagtcttgaa ctcctgacct    2940
tgtgatccac ccgcctcggc ctcccaaagt gctgggatta caggtgacag ctactgcgcc    3000
tggccaccca gctaattttt gtaattttag tagagacagg ttttgccat gttggccagg     3060 ctggtctcga actcctgacc tcaggtgatc cacccgcctc ggcctcccaa agtgctggga    3120
ttacagacgt gagccactgc gcctggcagg aacacctttta tactttcctc catgggtctg    3180
caggaaaagg gagccattga aaattgtggg ttaaataata gaaaatagtt ttatatcaaa    3240 accccctta cttatttatt tattttttat tattattatt tttgaaacag agtcttgctc     3300
tgttgcccag gctggagtgc aacgggaaga tcttggctca ctgcaaccta cacctcccac    3360
atttgagtga ttctcgtgcc cccgcctcct gagtagctgg gattacaggc atgcaccacc    3420
aggcctggct aattttttgta ttttagtaga tgggggttt caccatgttg ccaggttgg     3480 ccttgaactc ctggcctcaa gtgagtgctc tggcctccca agtgctggg attacaggca     3540 tgagccactg cacccagccc caaacccct taacaagca gtggttggca agttatcaag     3600
accatggact ttgaaccaa gttacatctc ttgggtttga atacaggctt catcatttcc     3660
tagctgtaag accttgggca gctgggtacg gctgtgtaat cccagcactt tgggaggctg    3720
aggtgtggga atcacctgag gtcaggagtt caagaccagc ctggccaaca tggtgaaatc    3780
ctgtctctac taaaaataca aaaattagcc aggtgtggtg gcaggcgcct gtagtcccag    3840
ctacttggga gtcgaggca tgagaatcac ttgaacctgg gaggcagagg ttgcagtgag    3900
ctgagatcac gccactgcac tccagcttgg gaaacagagc aagactccgt ctcaaaaaaa    3960
aaaaagaaga cctgcggcaa attacttttt cctacatcct aaggtaattg tgataattaa    4020
gtgaagtaat atgtgtagag cccttagaac tttacaatat ttgtaaaacc cttagaagtt    4080
```

```
ataaaaatta tttaatattt aaataattta atgaatgtac ttaattcatt tagtattatg      4140
tataaatata aaattatttt atatttgtaa agcccttaga accgtgcctg gcacacagta      4200
aagctctgtt tgcaaataat attttggctc accagtagac cactagttca tactgcttga      4260
tgataagcta ttccgcctca ttcgtccttg accccctaaa caggtctatg ccttggttgc      4320
tgggaaggtg tgttggcttt attaacagta atagtgatat gtccttttac caggcaattg      4380
catggaccag tatttatagg gaagtttgag ccctgccgca gaggggttaa gtgatgggaa      4440
aatgcctgcc attttcacat gctgttacaa ccaggcagta aaagtcctca gaagttaaat      4500
tttaagtaat cagactggcc actttccttc ctctgggaat gcagttggga tggagggctc      4560
tgtctctagt tggaaagaag tctgaagtcc cctcctgtgt ggacaccaga caacaggtat      4620
cccagggccc tctagttgac cagcaatact gtggaatgaa gacaccctca agtcacattt      4680
gaaatcattc cggttcttc cagttcagca ccttgactgt tttcctcttc actgggaagg      4740
tgctggcagc ctgacggcct tttaggcttc ttttaagttt ggggcatctg aaacccggcc      4800
aaggtgcggc gggtagtgta ctcattcgaa ggagaatacc cccaattcac tagacgagcc      4860
cctaattggg ggtgcggtgc cgggcgcgct ctttcctccc cctttccacc agcactgccc      4920
tcagttctgc ttctagccac gccctttcgc gttcacgtcc agcgcctgg cgggattgat      4980 ttgaggacga ctggactgcc attgcgcctg cgcagggagc ccaaggcaag agccgctagg      5040
ctgccctgcc cgaagggctc aactgtcagt gagcctgcgc aggaggccaa taggctgcca      5100
atactccttg gactccccgc cagggccctg ctgtcagtgc gcctgcgcgc gggtccggcg      5160
ccgaggttct tgactgctgt gccggacgcc aggtgtagcc atgcagcgag ccgattccga      5220
gcagccctcc aagcgtcccc gttgcgatga cagcccgaga accccctcaa acacccttc      5280 cgcagaggca gactggtccc cgggcctgga actccatccc gactacaaga catggggtcc      5340
ggagcaggtg tgctccttcc tcaggcgcgg tggctttgaa gagccggtgc tgctgaagaa      5400
catccgaggt agcggctccg gagggctga ggggcgaagg gcggcgacct ggggcgcggg      5460
ccaggcgccc tgagggaggg ggcccacga gaggaccgag gccgaggagc gagccctgcg      5520
gcgggaggca cccgggaggg cggacctgcg ctggggcgc cgaggaaagg aagacccgag      5580
gcgggggagg gagccctgcg gcgggggttc ccaggagggc ctgcggcatg ggctcccgg      5640 gactgactcc ccgaggcgga ggaagaagac atggggtcgc ctgggatagg cgattcgtag      5700
gatgggagca ggctcccggg attgaggacc tgggaggggc agtcgtagat tgggatctca      5760
ctctcgtggg tttcttcact aacttgccac cccggcgcgg gacaagcgag actcgggtcc      5820 cttttttta gttagaagga gattttttccc cagaccttgg tgggcggctt gctgtcatcc      5880
aggctcgcgg gacccctccg cgctaaccgc agctccttga acacttgcca catcagagga      5940
tgttctgggg cttttaggtt tcggtttcct ccctgaattg aggcttttcc tgaagggaa       6000 ggaactggct tggttaatct ctgaattccc atcaccttcc ttggcatccc agcagcgccc      6060
gataggcgtg tgttgactgc acttgcagaa catggtaagg aacatgtttt gctctttaaa      6120
agcaggttcc cctccaaaat ctgaaccttg gggttgttca gttgaccact gaatccccag      6180
catgccacag tttggccaca tcccctggag aagtgtttag gttgagtttt aatcatattt      6240
tactgattcg tatccaagca tccatccttg tgaattctac tcaacttttt gtggtgggtg      6300
tgagatttga ctcctgcctt atatcctcta ggtgtccaat aggaaggtga ttctttggtg      6360
gttgggattt gcaaatttag taaattttgt catttgttag gtggggccct gtttggctag      6420
gttggaaact ggggtaggag gaacattagt ggttcaggac ccaaagatag cttgaatggg      6480
```

```
tatgggaaat tgcatttctc cttttttttt tttcttcccc cttttgccct ttcgtttccc    6540
tccactgctg ggatggatta ttactttatt ttctttgact agcaacaagt ggagtgaagt    6600
agttccatat tttctgtctc aaaatgtggt tggctctctg tttcagtggt ttgtagatta    6660
actcgttacc ctccagaatg atgtgtgttc cttaaaccta caacctattg ctatcaaaga    6720
cactatgtgc tttcatttgg taaaaactga ccaactgttc ccaattgctc atgtcttagc    6780
ttctgctttg tcttgaccaa actttattcg gacttctctc ttcccttatg ggcccctcaa    6840
ctcttgctta cccccagatc tgaccaggca ggcactaaag cagtggaata tgcctccctc    6900
tggtcagttt cttttgagaa ccggctgacc acagtaggat gctgtcctgt tgggctacac    6960
tgctcatttt cccttgctcg tccaggttcc tatccaaaga ttctgcttat ttctgcttgc    7020
ccgtccttta tcatataaaa gaagacccct tttctgttgg attctttttt tttttttttt    7080 tttttttga gacagagtct cgctctgtcg ccaggctgga gtgcagtggc gccatctcgg    7140
cccagtgcaa cctctaactg cctggttcaa gctattctcc tgcctcagcc tcccgagtag    7200
ctgggattac aggcatgtgc caccacgccc agctaatttt tttgtatttt tagtagagat    7260
ggggtttcac catgttggcc aggatggtct ccatctcctg aactcgtgat ccgcctgcct    7320
cagcctccca aagtgctggg attacaggcg tgagccaccg cgcccggcct cattttttt    7380 ttttttttaa ttagagacag ggttttgcca tgttggccag gctggtctca aactcttggc    7440
ttcgagtgac catccaccca cctcggcctc ctaaagtgct gggattacaa gtgtgagcca    7500
ccatgcccaa cctctgtttg gttcttgggc ctctgtttga ttattttta aaatttattt    7560 tattatttta tttttttct gagatggagt ctcgctctgt cacgcaggct gaagtgcacc    7620
ggcacaatct cagctcactg caacctctgc ctctcgggtt caagtggttc tcctgcctca    7680
gcctccctag ttgctgggat tacaggtgca cgccaccacg cctggctaat tttgtgtttt    7740
tagtaaagac agggttttcac catgttggcc aggctggtct ccaactcctg tcctcaggtg    7800
atgcatccgc ctctgcctcc caaagtgctg ggattacagg cgtgagccac cgcgcccggc    7860
cggcctatgt gtttgattcc tgagcctctt gcagatatct gatattggag ctttctccct    7920
gtagaaatag tctttcttct tttcttttct ttttttcttt tcttttttt ttttttttga    7980 gacagagtct cgctctgtcg ccaggctgaa atgcagtggt gtgatctcgg ctcactgtaa    8040
cctctgcctc ccgggttcaa gcaattctcc tgcctcagcc tcctgagtag ctgtgactac    8100
aggtgcccac caccacacct ggctaatttt tgtattttta gtagagatgg ggtttcacca    8160
tgttggccag gatggtctta atctcttgac ctgatgattc acacgccttg gcctcccaaa    8220
gtgctgggat tacaggtgtg agccaccacg cccgaccagc aatagtcttt cttttctaata   8280 aagtttctct tggccgggca cggtggctca cgcctgtaat cccagcactt tggaaggccg    8340
aagcaggtag atcacctgag gtcaggaatt caagcccagc ctggccaaca tggtgaaaca    8400
ccgtctctac taaaaataca aaaattagcc gggcatggtg gtatgtgcct gtagtcccag    8460
ctacttggga agctgaggca ggagaatcac ttgaacctgg gaggcggagg ttgcagtgag    8520
ccaagatccc gccactgcac tccagcctgg gcgaccgagt gagactccat ctcggaaaag    8580
aaaaaaaaag tctctctttta tctaagtcca tttttttttt aatttgataa gccaagcaca    8640
aggtacagtg tccctttttct cattatggaa tacagcctca caagaagtct gaaataagtt    8700
actacactca acacatttta ccgatgatgt atgcgaggtc caaagatgta aagtaacttt    8760
tcagagatca caccactaca aaaagagct agattttta aggttaggtc tttggactct    8820
```

```
agaactcatg tgatctatac cttaacaagt attctcatca aaaccactg gaggcctggc    8880
ccagtggctc atacctataa tcccagcact ttgggaggcc agtgtgggaa gatcacttga    8940
gcccaagaat tcaagaccag cctgggcaac atcaggagac ctcaacttta caaaaaataa    9000
aaataaaaat tagctaggtg cagtggcaca tgcctgtggt cccagctact caggaggctg    9060
aggcaggagg atcgcttgag cccaggaggt caaggctgca gtgagatgtg atcgcaccac    9120
tgcactccaa cctgggcaac aagcaaaacc ctgtctcaaa gaaataaaa gaaatagtc     9180
cagagttctg gaatttgagg tcaggaaaga ttagaattaa ttgtatagaa agagaaagga    9240
aaaaacccaa caacacacac acacacacac acacacacac acacacacac accctcttc    9300
caaatcagag tattgagtgc tttcccagga cacacacaca cacacacaca ctcacacaca    9360
cacacacctc ttccaaatca gagtattgag tgctttccca ggacacacac acacacacac    9420
acacacacac acacacacct cttccaaatc acacacacct cttccaaatc agagtattga    9480
gtgctttccc aggacacaca cacacacaca cacacacaca cacacacaca cacctcttcc    9540
aaatcagagt attgagtgct ttcccaggag gtttgagaaa aatcaacact ttaagcactc    9600
ttgaattcac ggttttaact tgttaattct aagaacaata gacttaggtt tccttccctc    9660
cccaactcaa accttgttaa ttctaagaac aatagactta ggtttccttc cctccccaac    9720
tcaaagctgc tgacctggca aaaccccaac aggtagtcgg gtttcacttt cctttttgca    9780
actggttttt cttggaacta atttacacaa ataattttga aattttcacg tgatttatca    9840
aaaaatgctt cttggtttag ttatttaatt aaaattaagt ctttacaagt agcagatcaa    9900
aaaagtggta cttggcacaa tccattgcct gcagtgggta ctcacttatg tggatctggg    9960
taaatgttgg tgtatccaaa ttgaaagaaa atgaaaagca tatgttgtat acattgaatt   10020
tgtcttttt cttccataga aaatgaaatc acaggcgcat tactgccttg tcttgatgag   10080
tctcgttttg aaaatcttgg agtaaggtaa gaatgaagaa ataaattcac gttataacca   10140
aacacacttt atccatcttt cagggacaaa gcccaaaatc tctgatataa actgtcctca   10200
ttttaaatct atgaagtgct ttaaaacagc agaatccctt gcctgctggt tttgtttgtt   10260
catttgtttt ttgagatagt ctcttgttca cccaggctgg agtatctcgg ctcactgcaa   10320
cctctgcctc ccggcttcaa gttattctcc tgcctcagcc tcctgagtag ctaggattac   10380
aggtgcccac caccatgccc cactaatttt ttttcggttt ttttttttt tgagacagag   10440
tctcgctctg tctcccaggc tggagtgcag tggcgtgatc ttggctcact gcaagctccg   10500
cctcccgggt tcatgccatt ctcctgcctc agcctcccga gtagctggga ctacaggcgc   10560
ctgccaccac gcctggctac ttttttgtat tttttggtag acacagggtt tcaccatgtt   10620
agccaggatg tgtcaatct cctgacctcg tgatctgccc gcctcagcct cccagagtgc   10680
tggaattacc gcgcccggct gccccactga tttttgtact tttagtagag atggggtttc   10740
accatgttgg ccagactggt cttgaactct ggcctcaag tgatccgctt gcctcggcct   10800
cccaaagtgc tgagattaca ggtgtgagcc accgcgactg ccacctgct gtttgttttc   10860
gctgtacaaa tcctatgttt gctattactg tttattccta ttttagttta tttttaattt   10920
tatttattta tttatttatt gagacagagt ctcactctgt cacccagact ggagtgcaat   10980
ggtgcgatcc cggctcactg aaccccctgg gttcaagcca ttctcctgcc tcagcttcct   11040
gagtagctgg gattacaggc atgcaccacc atgcccagct aagttttgta tttttagtag   11100
agacagggtt tcaccatgtt ggccaggctg gtctcgaact cctgacctaa ggtggtctgg   11160
agttctgacc taaggtgggc caaggtctgc ccaccttggc ctcccaaagt gctgagatta   11220
```

```
caggcataag ccaccgtgtg tggccttatt cctattttaa ataatgttgc agacaaatct    11280
tcatcaagtt tgtagtgacc aacttttttac tctcaagttc agaataattg aattatacac   11340
actgggaaat acataagaac caatagggaa aaaaatgtta gtaagaaaat caaggctaca    11400
cccctatctt gagcatattt ctaggttttc ctaaagattg gaatatgccc tggtattaga    11460
tttaaagaca ctatgcaaaa caggcacttt ttagttgtat aatttgggag aagtcattta    11520
acccttcagt ttctgtacct gtaaaatgga taacaataat gagatgatgt acataaagtg    11580
ttgaagcata tgattaacgc ttagtaaatt ttatagatag tgatacagaa aattaaaaaa    11640
ttagccgggt actgtgcatg cacctgtagt cccacctaca ctcaggaggc tgaagcagga    11700
agatcccttg agcccaggag ttcaaggttg cagtgatcta tgataagctc ctgcactcca    11760
gcttgggcag cagaataaga ccctgtctca gataggtagg taggtagata gatacatata    11820
tacatacata catacatagt tacatagatc catctctgtg tatggctgta ggttctaggg    11880
tctagattag agtggggctc ctttaatgat ctcagtagag gatctggtgc ttaaatactt    11940
cttttttttg aagcggagtt ttgcttttgt tgcccaggct ggagtgcaat ggcacgatct    12000
cgtcttacct caaccttcac ctcccaggtt caagtgattc tcctgcctca gcctcccgag    12060
tagctgggat tacaggcatg cgccaccatg cccagctaat tttgtatttt tagtagagac    12120
ggggtttctc catgttagtc aggctggtct cgaactcccg acctcaggtg atccacccac    12180
ctcgtcctcc caaagtgctg ggattatagg cgcgagccac tgcgaccggc cttaaatact    12240
tcttaaaatg aagattttgt ttctgttaga aaattggcaa cagtggggaa atatggcctt    12300
ctcttctgaa atttttagtta catgttgttt gtggtaacag taaccaaaga atcaaaacaa    12360
aggattatac tgaattactt cctgtgctgt tgcttagtaa ttgataacag aagtacattg    12420
tgaaacaaga tcactgtaga acatttaact gacttccagt aaatatcctt tggatcagaa    12480
tctccaggga cctcatctta gccctttctt tttttttttt tttttgagac gaagtctcac    12540
tctgttgccc aggctggagt tcaagttcag tggtgttcaa gtgattctcc tgcctcagcc    12600
tcctaagtag ctgggactac tggcatgtgc caccatgccc ggttaatttt ttgtattttt    12660
agtagagacg gggtttcatc gtgttagcca ggatggtctc aatctcctga ccttgtgatc    12720
tgcccgcctc aggcctccca agttctttt tttttttttt ttttttgaga tggagtcttg    12780
ctctgtcact caggctggag gcagtggcg tgatctcggc tcactgcaac ctccacctcc    12840
cagattcaag tgattctacc acctcagcct cctgagtagc tgggactaca ggtgtgtgcc    12900
accatgcccg gctaatttt tgtattttag tagagacagg gtttcactat gttggccagg    12960
gtggtcttga actcccgacc tcatgatctg cctgcctcag cctcccaaag tgctgggatt    13020
acaggcgtga gccactgtcc ccggcatgac tctttcataa ccacatttca gccctctcag    13080
tcctctcaaa gtccccttta ctacttgttt cttgtacata atagttgctt actatttgac    13140
ctgaatggaa tttgttctaa tacagtcttt cttttcaagg gagccatgtg catgtttgtg    13200
gacccaagtg ctattgattc attcagtgaa tatttttgga aagctcacta tgtactagga    13260
attcttccat gaatttgggg cacatgagtg aacaaaacag acaaaggaac actatattgc    13320
agtgttccaa aaggaacact atattgcacg tctctgtgcc ccacctcata actcaaattc    13380
tgtaggactc cttagagctg tattgttctg tataataaca actagcttca cgtttaaatt    13440
aattagaagt aaaattaagta aaaaattcct cagttacact agccatattt caagtactta    13500
gtagtcacta tggctaacgg ctactgtgtt ggacagagca gatatagaac atttccatca    13560
```

```
tcgcagaaag ttctactaga cagtgctgcc ttacaggttg ccagtgggat tagccctacc   13620
caccactcca tccagttgct cacagtagta ccaatgcaat caacttgtta atggaccttt   13680
gtactgtttt tacctaattt cctattttac cctccctaga ccccccaatc cctgtgccca   13740
gagttcaccc caagattaat tacttgcaag ctcttatcct ggaccctgct ttctagggag   13800
aatccagctt agacaagcac tcctagtagg ccctcaattt tatgaacaac cattgattta   13860
taaaggtttt tttaacaagt aagaaacagg ccaggcgtgg tggctcaggc ctttaatccc   13920
agcactttgg gaggccgagg cgggcggatc acgaggtcag gagatcgaga ccatcctggc   13980
taacatggtg aaaccctgtc tctactaaaa atacaaaaac aaaaaagaaa ttagctgggc   14040
atggtggcgg gcggctgtag tcccagctac tcgggaggct gaggcgggag aatggcgtga   14100
acccgggagg tggagcttgc agtgagccga gatcacgtca ctgcactcca gcctgggcaa   14160
cagagtaaga ctccatttca aaaaaaaaaa gaagttagat agaaacattg tcacgttaaa   14220
tatacatgtc aattgtaaga agcattaaat ttcagaaatg ttggaacaca ggaataaaat   14280
tctttcataa tctagatatc ctggcccatg acttctttaa atctttattt aatgccatgt   14340
cctttgctaa acaaaacaac cccctggttt tgggtggttt tatatactct aatcagtgat   14400
tttggttttg ttttgttttg ttttgagtt ggagttttgc tcttgttgcc caggctggag   14460
tgcaatggcg ccatctcggc tcaccgcaat ctccgcctcc cgggttcaag caattctcct   14520
gcctcagcct cccgagtagc tgggattaca ggcatgcgcc accaccacgc ctggctaatt   14580
ttgtattttt agaagagacg gggtttctcc atgttagtca ggcttgtctc gagctcccaa   14640
cctcaggtga tccacccacc tcggcctccc aaagtgctgg gattacaggt gtgagccact   14700
gcgcccggcc gattttgggg tttaagcga tgaataccaa atgtcagttt aggaaaatat   14760
taagtggtca cggggttagt ttaggtttga tattttatgc tatgactccg gttttgctca   14820
actatgtgac tccccttaaa ctaagtccac ctataagtac ttctgaaagc ctggctttac   14880
actgtgcttg ttatgtcaaa ctgatgagga ggataggga ataggaaaac acgaaatttg   14940
ctgctttaat ttatcagctg taataatgct tctgtgtatc ccaagatatt attcttaagt   15000
gttcttatta ccatgggttc agtgtgtacc atagaggcca atgtagtgcc tctgactccc   15060
agtctatgta tgacttgtag aaagatactt tttttttcaat ctggttatct agtagatcag   15120 taaaacccctt tgcctgcact ctctgttgac acccagccag gagggaggat gatatgctgg   15180
gcccaactag taattgtaaa tgaagcagga taatgaatca caggacttcg agctgctcaa   15240
atttaattcc cattatgtat tttcttgaaa ctggagcatt gtgagggagt actgacaatg   15300
gaaaatgaat ataaataaag ttaaagcctt catatgtatt tcattcatgc ttgagtcata   15360
cctggtgctc ataaatcaat ccaggattat gagggtagat gttgacttca gtttggttaa   15420
aaggaagtac agtttgagca ttgagtagac atggagatgt ggagttttc aagtcttaaa   15480 tttaccaaga gagaggaggg tcaaggacag aaggctgtgg gaggcctata ttgattcagc   15540
aggagagttc cctatcttaa cagcaaagga aggagagagt ttctaggagg ggtatgtttg   15600
aattattgat tgttccttcc aatctaactt ctgttagtgt agataatata agtttatta   15660 tgtctactat atactgcagg gattattatt aagcaaataa tgatagactt gcttatccta   15720
ttgtaatttt agttccttgg gggagaggaa gaagctgctt agttatatcc agcgattggt   15780
tcaaatccac gttgatacaa tgaaggtaag aggatctgag tttgttatgt ttttgaata   15840 taaagtgata taactcaatt atgtaaaatt cattttgaag agaataggag gaaatctgct   15900
tctcagtgat agaattgtga gtagtggatc ttttctaaac tttctgcact ttctaaaatg   15960
```

```
agcacagagt atttaaatca gaagaagaac taaaatatgt ttaagcatac agaaaagcat    16020
aagtagacca ctacccaact tgtcaaatat taatattttg cctaatttgc ttcaagtctg    16080 ttattttag agcaaaatat tagaaactat tgaagacctc ctttgtacat tctttttttt    16140
ttaatgaaat gtggtcttgc tctgtcatct aggctggagt acagtggtgc aatctcagct    16200
cactccaacc tccgtctccc tggctcaagt gatccttcca tctcagccac cccagtagct    16260
tggactatgg gtgcatgcca ccacacctgg ctaattttg tatttttat aaagacgggg    16320 tcttcctgtg ttgctcaggc tggtctcaaa ctcctgggct caagagattg acctgccttg    16380
gcctcccaaa gtgctaagat tacagatgtg agccccacg cctggccctg tttctattta    16440
ttatgtttct atccttttct ccctagaagt aataagcatc ttcctgaatt tgatgtttat    16500
cattgtcatg aatggttttt actcttattg catatttatg tatatccata aacaatgtat    16560
agtattgttt tacatatttt taaactttat ttttttgaga cagagcctgg ccttttttt    16620 ttttttttcc tcttttgag atgtaatctc tctctgtcac ccaggttggg gctcagtggc    16680
actatcttgt ctcactgcaa cctctgcctc tcaggatcaa gtgattctcc tgcctcagcc    16740
tcccaagtag ctgggattac aggcatacac caccacaccc ggctaatgtt tttgcatttt    16800
tagtagagtt ggggtttcat catgttggcc aggctggtgt caaactcctg acctcaagtg    16860
atccacccac ctcgtcctgc caaagtgctg ggactacagg catgagccac tgcgcccagc    16920
cagaatgtgc attttcaca agctcttcag agtgattcta aaaccatact tgatgaaatg    16980
tttcttgttt tgttagtgac aggaaataga ccttatttac tcttttgaca ttcctaggtt    17040
aagaaaactt agtttcagac ctgggagaag atgtaggata tcttctttt ttgtactttt    17100 ttgcccgatc atcatttgca tttttcactt tttttaaaaa atagatgtaa tgtatagtat    17160
ttgagttatt tcagatccct ctctataaga atacatattt taattttgct tttgcaagtt    17220
atagacttct tttctttctt tcttttttg agatggagtc ttgctctgtt gtctaggctg    17280
gagtgcagtg gcacaatctg gcttactgca acctctgcct cccagtttca agtgattctt    17340
ttgtctcagc ctcccaggta gctgggacta caggtgcaca ccaccatgcc cagctagttt    17400
ttgtattttt tttagtaaag acagggttcc gccatattgg tcaggctggt ctcgaactcc    17460
tgacctcatg tgatccgtct gccttggcct cccaaagtgt tgggattaca ggcatgagcc    17520
aacacgtctg gcctacccgg ttattttctt tttcttttct tttcttttt ttttttttt    17580 tttttttttt gagagggagt ctcgctctgt tgcccaggct ggagtgcagt ggcatggtat    17640
cagctcactg caacctctgc ctcccagatt caagcagttc tcctgcctca gcctcctgag    17700
tagctgggat tacaggcacc tgccaccacg cccagttaat tttttttttt ttttttttt    17760 tttttttg tatttttagt agaggcaagg tttcaccagg ttggccaggc tggtcttgaa    17820
ctcctgacct catgatctgc ccaccttggc ctcccaaagt gctgggatta caggcgtgag    17880
ccaccagccc gttctaggct tattttctat tgaaaatcac atctgaaaaa atttaatgaa    17940 cattttggt tcaactatat aataatgttt tgttgttgtt ttgttttgtt ttgttttga    18000 gatggagtct tgctctgtct cccaggctgg agtgcagtgg tgcaatctcg gctcactgca    18060
acttccaaat cccaggttca agtgattctc ctgcctcagc ctaaatcagc ttcctgagta    18120
gctgggacta caggcgcatg ccaccatgcc cagctaattt tttgtatttt tagtagagat    18180
ggggtttcac cgcgttagct aggatggtct cgatctcctg acctcataat ccacccgcct    18240
cagcctctca aagtgctggg attacaggca cgtgccaccg tgcctgtccc tgttttgttg    18300
```

```
ttttgagagg gagtttcact cggttgccca ggctggagtg cagtggcgtg atctcagctc    18360
actgcaacct ccgcctcccg ggttcaagca attctcctgc ctcagcctcc tgagtagctg    18420
ggattaccag tgcatgccac cacacccggc taattttttgt attttttagta gagacggggt   18480
ttcaccatgt tggccaggct ggcctcgaac tcctgacctc gtgatctgcc tgcctcggcc    18540
ttccaaagtt ttgggattac aggcatgagc caccgtgccc agccaataat atattttga    18600
ggtaatattt aaggcagtca gtggtttcaa ttgcccactt ttattctttc tattttttctg   18660
taaaaagaac attgttggct gggtatggtg gctcacaccc gtaatcccag cactttggga    18720
gactgaggta ggtggatcac ttgagcccct aagttcaaag accagcctgg gcaacatggt    18780
gaaactccat ctacaaacaa tagaaaacaa tagaaaaatt agctgggtgt ggtagtgcac    18840
acctgtagtc ccagctactt gggaagctga taggaaaa tcacctgaac ctggggaggt     18900
ggaggcttca gtgagccatg atcacgccgc tgcactccag cctgggcaac agagtgagac    18960
cctgtctcaa aaaaaaaaa aaacaaacca acattgttta acctcattta taaattataa    19020
atgacagttg ttggaaatag attttcaaac tactgaatca cggcttagta atgaaatcaa    19080
taccttaaat gaatttaact tcatcagcaa tgcagttcaa caagaattga cctagtttgc    19140
tactcagttg cagacctcaa ggatttctac cctaatttca tacctaccta acttgatact    19200
taaaacataa atgctttatt gagatataat tcacaagttg tatgattcac tcattttag    19260
tatgcaagac agtgcttttt agaaagttca cagtgttgtt caatcacaca caatttgatt   19320
tgagttgtaa gagctcttta tatgttctgg atgtaaatcc ttatgggaga tatgatacac    19380
aaatatttt tcccagtctg tgggttgtct ttttactttt ttgatggtgt tctttggatc     19440
acaaagtttt taagttttta tgtaatccaa tttatatttt ttttgttcat ttgtgtcttg    19500
tacttttagt gtcatattta agaaaccatt gccgaaccca aggtcaccat ggtttgttct    19560
tgacacagtg ttctttatgc taaatttagt tcagttggcc tctgaagctg agattgtgta    19620
atggtgaaga gggagtgcag tgtttgacat aatgaggact aattttttcaa atgtatcaat   19680
gaatctttt ttttttttttt tttgagatag agtctcactc tgttgcccaa gctggagtgc    19740
agtggcacaa tctcagctca ctgcaacctt tgcctcctgg gttcaagcga ttctcctgcc    19800
tcagcctcct gagtagctgg gataacagac gcccaccacc acgcccagct aattttttgta   19860
tttttagtag agacgggatt tcatcatgtt ggtcaggctg gtcgtgaact cctgatctca    19920
ggtgatccac ccgccttggc ctcccaaagt gctggcatta caagcatgag ccaccatgcc    19980
ctgccagaaa ccccatctct accaaaaaaa gaaaaattag ccaggcgtgg tatagttcca    20040
gctacttggg aggctgaggt gggaggatcg cttgaacttg ggaggcagag gttacaatga    20100
gccctgattg tactccagct tatgtgatag agctagactc tgtctcaaaa aacaaacaaa    20160
caaaaaagac agttattaca acctgaaaaa tttacagtga aggcttttag gtccttaaat    20220
ggtttaaaag tagattttag ccaggcgcgg tggctcatgc ctgtaattcc agcacttcgg    20280
gaggctgagg cgggcggaca cgaggtcagc ctgggcaata tagcaagact tgtctccac    20340
aaagaataaa aataaattag ctaggaatgg tggtacatgc ctgtagtccc agctatttgg    20400
gaggctgagg caggaggatc cctggagcct aggagtttga ggctacagta agctatgatt    20460
gtgcctgtga atagccaacg cactgcagcc tggtgagaaa gcgagaccct atctctaaga    20520
aaacaaaac aaaagaaca cacacacata aacacattgt tcagctgtac aaaattattt     20580
tcttgctttt tttcttcttt ttttgagaca gagtttctct ctgtcgccca ggctgaagtg    20640
ttgtggcaca atagtaggtt actgcagcct tgatcccctg gggctcaagg gatcttccta    20700
```

```
cctcagcctc tagagtaccc gggactacag atgtgcgcca ctgcattttt gtttttaaag   20760
atggggtctc actatgttgc ctagactagt ctcaaactct tggcctccca aagtgctggg   20820
attacagatg tgagcacctg cactcggacc tgcatgattt cttatctata tggtagagga   20880
atttccatct ttctttcttt ccctgcctcc cttctttctt ttctgtttta atgatgagtg   20940
ctgtatagat acatttagaa aaaaaaaaat ttaggccggg cacggtggct cacgcctgta   21000
atcccaacac tttgggaggc cgaggtgggc ggatcacttg aggtcaggag ttcgcggcca   21060
gcctggccaa catagtgaaa ccccatctct actcaaaata caaaaattag ctgggcatag   21120
tggcacaccc ctgtagtccc agctactcag gaggctgagg caggagaata gcttgaactt   21180
gggaggcaga ggttgcagtg agctgagatc gtgccactgc actccagcct gggtaacaca   21240
gtgagactct gtctcaaaaa aaaaaaaaaa aattagacat aatacctata gtgatatggg   21300
ttacatgatg tggatgaatg tgtttaaatc gaaatgaata tgcatgttta acttgaatac   21360
aagacaaact tattaaagac taagtcatat acataataaa aaatcaaaat ccttattttt   21420
ctgttattca catccattag gaagaagtaa aatatactca aatccaatat acttgatctg   21480
tctggtagtg atacctaaat aaggtaatga tgttaacatc ttgtcatttc cgttagtatt   21540
tttacttgaa aaatcaaata gctttgactt tgcactataa ttaggaatgg ctgcacacaa   21600
atttcagttg gacttacatg tcgttatttg tattaattaa acataatttt ctaggtaatt   21660
aatgatccta tccatggcca cattgagctc caccctctcc tcgtccgaat cattgataca   21720
cctcaatttc aacgtcttcg atacatcaaa cagctgggag gtggttacta tgttttccca   21780
ggagcttcac acaatcgatt tgagcatagt ctagggtaag aagggaatgg ggtggggaac   21840
ttgcagtttt taagtatttt ctctgtctca tgaaatagtt atcttaggcc aggcatggtg   21900
gctcacacct ataatcccag cactttggga ggcagaggtg ggtggatcac atgaggtcag   21960
gagttcaaga ccagcctggc caacattgtg aaaccccatc tttactacaa atacaaaatt   22020
agccagacat gattgtgcgc acctgtaatc ctagctactc aggaggctga ggcaggagga   22080
tcacttgaac ccaggaggtt ggtggttgca gtgagctgag attgcaccat cgcactccag   22140
cctaggcaac aagagcaaaa ccccatctca aaaaaaaaaa aaaaagaaa gaaaagaaa   22200 acaggaaaaa aagaaatag ttgtcttaat cttttagaga ataaatagtt ttacaaaatg   22260
atgataatgt ccttatttta ttgatgagaa aattgaggct tttttttttt tttttttttt   22320 tttttgaga cagagtctct ttcactaggc tggagtgcag tggcgtaatc ttggctcact   22380
gcaacttcga cctcccaggt tcaagcagtt ctgtacctca gcctcctgag cagctgggat   22440
tacaggcgcc caccaccaca cccggctaat tttagtaatt ttagtagaga cggggtttca   22500
ccatcttggc caggctggtc ttgatctcct gaccttgtga gccacctgcc tcggcctccc   22560
aaagtactgg gattacaggt atgagccact gtgcccagcc ccaaaattga ggctttttat   22620
ttaccttgtt gcaattttatt tattttatgt attcttaacc acctcagatc tttcctggaa   22680
aaataatgaa agtatctata gacaggtcag ttggatttgt ttttaaatat taattaaaag   22740
ctaacagggg ctgggtgtgg tggctcacac ctgtaatccc agcacttttt ttttttttga   22800
gatggagtct cactccgtcg cccaggctgg agtgcaatgg cacgatctca gctcactgca   22860
acctctgcct ccagggttca agtgattctc ctgcctcagt ctcccaagta gctgggatta   22920
caggtgccca ccaccacgcc tggctaattt ttgtattttt tagtagagac agggtttcac   22980
cacgttggcc agggtggtct tgatttcttg acctcgtgat ccgcccgcct cggcctctca   23040
```

```
aaatgctgag attacaggca tgagccaccg tgcccggcca atctcagcac tttgggaggc    23100
cggggcaggc ggatcacttg agatcatgag ttcgagacca gcctgagcaa catggtgaaa    23160
ccccgtctct agtaaaaata caaaaattag caaggcgtgg tggcgcacgc tgcagctact    23220
tgggaggctg aggcaggaga atagcttgaa cccgggaggc caaggttgca gtgaactgag    23280
atagcaccat tgcactccag cctgggtgac agagtgagaa tcagtctcaa aataaataaa    23340
taaataaata aaagctaatg ggtcggttgc tgatacaact aattatgtat atttgattat    23400 ttaattttc tgtattctct atttactctg gtacagagtt gctctttcaa accagatcat    23460
tttcttacct gtcaggaaat gcgtaagtta aaaaagcatt cataatctta gagaaggcga    23520
tgcctctgtt acatacaact aagctgagac gttggtctgc atttccatta tgcagtgtag    23580
agccaggagg aagtggacag ggaagaatag acagtctttg agattttcat gaagtactca    23640
cagtatatta ctttggtttt ctgtttgtgt agaagcattt ttagttaggc acaacatgtg    23700
tctatactca aatgttcatt catcaacaaa tatttatcga accttactaa gccctaccaa    23760
accacaaaaa gataacaatc gcctctgtcc tcatgtagct cagagttcag gggaaaagaa    23820
tttaggaatg gctcagatgg aagtgctgga agtgcattta agtacttcat ctccaattat    23880
gttgtaaaca ttacaaagcc agatattcct actttaaaaa aaaactgtgg taaaatacac    23940
agaatagaaa atacatagtc ttaagtgttt tttaagtgta cagtttagta gggttaaatg    24000
cattcacatt gtgcaaccaa tcgattgcca aaactcttat catcttacaa aaccaaactt    24060
gccaaaactc ttatcatctt acaaaaccaa acttgccaaa actcttatca tcttacaaaa    24120
ccaaacttgc cgggtgcagt ggctcacacc tggaatccca gcactttggg aggctgaggc    24180
cagtggatca cctgaggtca ggagttcaag atcagcctgg gcaacatggc gaaaccccgt    24240
ctctactaaa aatacaaaac cagccgggca tggtggagtg tacctgtaat cccagctact    24300
cctgaggttg cagtgagctg agatcaggcc agtgcactcc agcctgggca acacagcgag    24360
actccatctc aaaaaaaaaa aaaaaaaaac acgaaactgt atacgtatta aacaactctt    24420
catgtctccc cccgcaaccc cccgcaaccc cctagtaact accattctac tttttttttt    24480
tttttttttt tggagacgga gtttcgctct tgttgcccag gctggagtgc aatggcgcaa    24540
tctcggctca ccacaacctc cgcctcctcg gttcaagtga ttctcctgcc tcagccttcc    24600
aagtagctgg gattacagcc ttccaagcag ccttccaagt agctgcctca gcttccaag    24660 tagctgggat tacagccttc caagtagctg gcacctgcca ccacgcccag ctaattttgt    24720 attttagta gagatggagt ttcaccacat tggccaggct gttcttgaac tcccgacctc    24780
aggtgatctg cccacctcag cctcccaaag tgctgggatt acaggcataa gccaccgcac    24840
ccggccctct tttttttgtt tatgaatttg gctactctag gtacctcatc ttagtgaaat    24900
catataatat ttgtcttttt gtcactggct tatttcactt agcataattt cctcaaagtt    24960
catctatgtt gtagcatgtg tcagtatttc tttcctttt tattttttat ttttatttt    25020 taaattattt tttatttcct ttttaaggtt gaataatatt ttatcatatg tatctaccac    25080
attttgttta tacattcatt tgttgatgga tacctgttgc ttttacctct tggctatttt    25140
gagtagtgct gctatgaaca tgtctgtaca aatatattct cttctttttt tgggggggag    25200
ggtggtgggg acggaatctt gctctgttgc ccaggctgga gtgcaatggc aagatctcgg    25260
ctcactgcaa cctgtacctc ttgggttcaa gcaattctcc tgcctcagcc tcccaaatag    25320
ctgggattac aggtacctgc caccatgctg agctaatttt tgtattttttt agtagagatg    25380 gggcttcaac atgttggcca ggctggtctc gaacccctga cctcaagtga tctgcccgcc    25440
```

-continued

```
tcagcctccc aaagtgctgg gattacaggc gtgagcccct gagcccagcc aatcttttca    25500
agacctactt tcgttattgt gggtgtatac ccagaagtga aattgctaaa tcactgtggt    25560
aattccgttt ttaattttttg tggagcaccc atactgtttt ccatggcagc tacaccataa    25620
tacatcccca ctaacagtgc acaggcttcc aacttcttca catcatgtcc aacacttgtt    25680
attttctggt tttcttttttt taatagtagc tatcctaagg ggtgtgaagt ggtatctcac    25740
tgtggttttg atgtgcattc ctctaatgat tggtgatatt gagccagagg tcctgctttt    25800
gggattccgt ttgtgtgtgt tcctgcctag ttctgaaata tactgttcag taaagttgcc    25860
ctaaaggtat gttagaatgt ttaaggaaac atactgaagt tcttgaggac cagaactatc    25920
actcctcttg caaacagaaa agtgactttt tgtgtttttg ctctgcaggg tggggtatct    25980
agcaggatgt ctagttcacg cactgggtga aaaacaacca gagctgcaga taagtgaacg    26040
agatgttctc tgtgttcaga ttgctggact ttgtcatgat ctcggtaagc tgtacaaaga    26100
gacaaagttg ttatgtaaaa tcataacata tgttacctct cttttgacgtt aaaaaatcag    26160 atcaaccaag agaatatgga aattgtattt taattcttca gttgatgtta gtataaatgt    26220
actgttgctt cttcctagaa tgattcataa gtagaaaaca ttgctatttt attttcttgg    26280
caactttcag tgaatttctc atgttaaaca tctttgctaa agtggttttt ttgttgttgt    26340 ttttttttttg agacagagtt ttgctctgtt gcccacgctg gagtgagtgg ctcattatcg    26400
gttcactgca acctccgctt cctggtttca agcaattctc gtgcctcagc ctcccgagta    26460
gctgggatta caggcatgca ccaccatatc cagctaattt ttgtattttt agcagagacg    26520
gggtttcacc atgttggcca ggctggtctc gaactcctga cctcaggtga tccaccagcc    26580
tcagcctccc aaagtgctgg gattacaggc atgagccacc gtgcccggcc atcatgttta    26640
ctacaggtta tatgaaaggg cttttttgcta gtgagttttt cttactactg cttttaggat    26700
gatatgtgaa tttattttt cttttatcct tcttatgctt attttttttt ttttttttgg    26760 tcttttttttt tcttcctttt tgtggagaac aggatctcgc tatattgccc aggcaggtct    26820
cgaactccta ggctcaagct atcctcccgc ctctcctccc tgagagctgg gattacaggt    26880
gtaagccacc gcgcctggcc ttgtccttct tatcaaataa aatcaccatt tttccttcgg    26940
ttatttggtg aaatccattt ttttttcatat ttataatctc taatctgccc aagtggatta    27000
acacatttag agaactcctt gtcttttctg atccatgtga ggtcttaggc cactttaatc    27060
caagcaaaag aatataatcc ttttcctgtg acaaagagaa aggggactgt cccatttatt    27120
tttttatttt tgagatggag tcttgctctg tcacacagat tggagtgcag ttggcactat    27180
cttggctcac tgcaacctcc gcctcctggg ttcaagtgat tcttctgcct cagcctcccg    27240
agtagcgcct ggctaattttt tttctatttt tagtagagat gcagtttcat catgttgttg    27300
aaactggtct cgaactcctg acctcaagtg attcacctcc cttggcctcc caaagtgttg    27360
ggaatacagg cataagtcac cacgttgggc cgggactgtt ccttttaaat catgggggtt    27420
tttacctcta tccttatagt ttattcctac ttattcaggg actctgagag tttgtgtgta    27480
ccctcagggc aggggaaggg aggtgcatgc cactgtttgg atagccagat acttaaagca    27540
agtaggcact ctttttatgt cccccggaga cttacaaaga accaataccca gcccctagat    27600 gataaatttg atggattctt ggtattttga gggagaatca ttgggaaacc tttgccagtc    27660
cccaggagcc tgagcactgc attagcgagc ctttatgtgt agcctgtgac ttgcaaagca    27720
gggccaaggc tagtctaggt agacttccct ctccagttaa gtggctcact tcttttttttt    27780
```

```
tttttttcag atggagtctc gctctgttgc ccaggctgga gtgcaatggt acgatcttgg   27840
ctcaccacaa cctccacctc ccaggttcaa gccattctcc tgcctcagcc tcccaagtag   27900
ctgggactac aggcacatgc caccatgccc agctaattat tatagtttta gtagagatga   27960
ggtttcacca tattggtcag gctggtctca aactcctgac ctcaggtgat ccacccgcct   28020
cagcctccca aagtgctgag attacaggca tgagccacca cacccggcca agatagatt    28080 tttttaagct tgagagttat aagagaaatt ctaattttt cttcctgcac cccagtggat    28140 tttcttttt ttttttcccg agacagaatc tcgctctgtt gcccaggctg gagtgcagtg    28200
gcgcaatctc ggctcactgc aacctccgcc tcccgggttc aagcgattct cctgcctcag   28260
cctcctgagt aggtagtatt acaggcgcct gccaccacac ccgcctaatt tttgtatttt   28320
tagtagaaac agggtttcac catcttagcc aggcttgtct tgaactcctg acctcgtgat   28380
ctacccgcct cggcctccca aagtgctggg attacaggca tgagccaccg cgcccagccc   28440
cttttttttt cttttgagat ggagtcttgc tctgtcaccc aggctggggt gtagtggtgt   28500
gatcttggct cactgcaagc tccgcttccc aggttcacgc cattcctg tctcagcctc     28560 ccgagtagct gggactacag gtgcccgcca ccaagcccgg ctaatttttt gtattttag    28620 tagagacagg ttttacca tgttggccgg gctggtctcg aactcctgac tcaaagtgat     28680 ccaccacct cagcctccca aagtgctggg attacaggca tgagccacca cacctggccc    28740
tagtggattt tcttgaaact gctattttaa tccagatatt ttcaatctga agatttcaaa    28800
aagttttggg cattaacatt ctttttagtt acacagaatt gtccatttat caagccctgt   28860
gtggtggtgc atgcttgtag tcccagctat tcaggtggct gaggcaggag gatgacttga   28920
ggtcaggagt ccaaggctgc agtgcataat gatcatgctt gtgaatagcc actgcactcc   28980
agcctgaaca acatagcaag actctgtctc ttcaaaaaac aacaaaaact gcccttttat    29040
cagatttatg taaaacctgg tgactggaga ctgctcgatg gagagcttac ttttccatgt   29100
ttctgcttcc tgttctcctg ttttagaaat aggaagaaag ggtttgtccc ttttgtgat    29160 tgtatttta gattattaat ttcttttgct attcaagtta aactaaaaag attaagaat     29220 tcagtttggc tgagtgtggt ggctcacgcc tgtaatccca gcactttggg aggctgagac   29280
gggcggatca cctgaggtcg ggagttcgag accagcctga ccaacgtaga gaaactccat   29340
ctctactaaa aatacaaaat tagctggatg tggttgcaca cgcctgtaat cccagctact   29400
cggtagcctg aggcaggaga atcgcttgaa cccagggggc ggagattgtg ttgagccaag   29460
attgtaccac tacactccag cctgggcaac aagagcgaaa ctccgtctca aaaaaaaaa    29520 aaaaaaaag gaaaaagttt tgttggttt acagatgttt ttcttgttct aaggctgctt     29580
ttgtttttaa ggtcatgggc catttttctca catgtttgat ggacgattta ttccacttgc   29640
tcgcccggag gtgaaatgga cggtatgtat tcatacagtc aatagtcaat aaaaagaaag   29700
actatttaag caggttattt agttaattta tctgtttggt tccactactg tgttataaaa   29760
tacttcccca ttacagtgtc cagggtgctt tcattcacat atatatat atgcttttgt     29820 ttggttctca cagtagtctg taaggaagtt atcgttatct ccctttttac aaataaagga    29880
acttgaaact cttggatgtg tattgatgca tcaaaaatca caaagccgtt aaatactgga   29940
atcagcaata caaaaccagt tgccagttta atactccttc tgctccattg tactactgta    30000
taataaaagg ccaactccag ttttgacaca tttggtatga ccacgaacta acttaccagc   30060
caagtcatat atattaaatg aatcatttta aaattaggca tttgcaggtg gctgtcccat    30120
attttggaat caatttttga gaagtaaaat taggttggtt tttactacac tgtatttctg   30180
```

```
gaacgggaat agaaaaagga tattaatata tattgaaaac ttcttacatg tcaaccactt   30240
tttttttctc tctctctttt tttgaggtat agttcacata caataagttg tccagatctt   30300
aagttcagtg agttttgaca ggcgtataca tccatatgac tattacccag tcaggatata   30360
gaacattttc atcttcctga aaaattccca tgtgcttttt cctagtcaat tctcactccc   30420
cctcacccca ccatcacctt ctgatttta caaacataaa tgaattttgt tgttcttaga   30480
cttgattaag cagaatcata taggaggtcc tattttatgc cttgctttat ttactcaaca   30540
taatggtttt gagatttgtt catgttatgt gcctcagtag ttgatccttt tttttatcgc   30600
ctacgtagtg tggcattatg caaataagtc acaatttgtt tacccttttct tgttttgttg   30660 gaatttggat tgttttcagg ttttggttgt tataaataag gttgtcgtgc atattatcgt   30720 acaagattttt ggtagaaata cattttctat gttgttgtag tgtggaaagt taattacatt   30780
tttaaaacaa gaaatacatt cagcagaaat acattatttt ataaaaataa aaatagataa   30840
aataaagaaa tacattttca tttcacttag gtaaataccg aggagctaga attgctgggt   30900
catatggtag atatgtattt aattctataa gaaactacca gagttttcca atgcggttgt   30960 accatttttac actcccatca gcaacatact ggagttccag ttgttttaca gcctcatcaa   31020
catttgacct ttcaaattag cccttctaat gagtgtcaaa tggtatttca tggtttgatt   31080
ttctaatgta tgttgaatac tatttcctgt actttgtact ttgttattga tatatcttct   31140
tctgcaaaga actctcaaca ttttactcgt ttaaaaagtt tgattgcttg ctctttgatt   31200
actgagttgt aggaattctt tatgtatata tatggttagg tatatgtatt gtgaatatttt   31260 ttccccagtg tctggcttgg ccaattcatt ttttcatggt gccttttgaa aaacagacgt   31320 tttcaattttt gatgaagtac tctggttctg caagccagta aaatgggtag tttctcacca   31380 gttttttctgt cctggggcct gcccttaggc aaaaaaccat aaaaccggaa tgtcacccag   31440
cacctctccc ttctaagtat tgaggtctaa catccacttg gttttggtct ctctccagga   31500
ccttcaggga gttgtccaga gcttatagtt gtttttcttct gcagttgatc taataggatc   31560
ttctcaatca ttaccaaatc tattcctta agcatttgc ctttcacatt taaatcctta    31620
gctcgtgtac aatttatttt tgtgtaagta tatgggagaa atctttttt ttctttttt    31680 ttttttttga gatggagtct cactctgttg cccaggctgg agtgcagtgg tgcgatcttg   31740
gctcactgca acctccacct cctgggttca agcgagtctc ctgcctcagc ctcctgaata   31800
gctgggatta caggcatgtg ctaccacacc tggctgactt ttgtatttt agtagagatg   31860 gctttcacca tgttggttag gctggtctcg aactcctgat ctcatgatcc acccacatcg   31920
gcctcccaaa gcgctgggat tacagacgtg agccaccgtg cccggccgag aaatctaatt   31980
ttttaatagt tcatcctatc cccactgact gtaataccaa ccccaacatt tattaacttc   32040
ccatatatga tgaatcattc tgcattctgt tctgtttcca cacttgttac ttggggaaga   32100
aaaaaaaaga agaaagaaa tttttatctg agaaatatga gcccctttac attatcaggc   32160
ccagagaggc attgaaatag aacagcaatc atgtcacgcc cccttgagct aaataattat   32220
tatctcttga agccagctgt tatgtgggat gccaggtaac cataaaatgc catatatcct   32280
gtacttcata atatgtagcc aatcactaac taatgttatt tctgtaagcc agtgaacatt   32340
cctgactaac aacttttgtt atcacctcct ctttgtgatc acctcctcct cctgatttat   32400
gctcttttct ttttttttct tttctctccc ttctgtctct gtctctcttt ttctctttct   32460
cactttcttt ctttctcatt ctttctcttt ttcccttcct tccttccttt ccttccttc    32520
```

```
tttcccttcc ttcccttctt tccttcctt ttctttcccc ttccccttc cctcctttcc    32580 cctcccctcc cctcaacagg atcttgcttt gtcacccagg gtggagtgca gtggtgcaaa    32640
catggcttac tgcaacctcg acttccaagg ctcaagcaat tctcccactt catcctccag    32700
agtagctggg actacaggca cacactacca tgcccagcta attttttata tttttttgtag   32760 agggagt                                                              32767
```

<210> SEQ ID NO 20
<211> LENGTH: 10
<212> TYPE: PRT
<213> ORGANISM: Artificial Sequence
<220> FEATURE:
<223> OTHER INFORMATION: Region of similarity between P51BP4_596 and
      RNA methyltransferase
<220> FEATURE:
<221> NAME/KEY: Xaa
<222> LOCATION: (8)..(8)
<223> OTHER INFORMATION: Xaa denotes a region of non-similarity

<400> SEQUENCE: 20

```
Ser Glu Asn Thr Lys Ile Ser Xaa Val Lys
1               5                  10
```

<210> SEQ ID NO 21
<211> LENGTH: 10
<212> TYPE: PRT
<213> ORGANISM: Artificial Sequence
<220> FEATURE:
<223> OTHER INFORMATION: Region of similarity between P51BP4_596 and
      wingless-type MMTV integration site family, member 7B
<220> FEATURE:
<221> NAME/KEY: Xaa
<222> LOCATION: (8)..(8)
<223> OTHER INFORMATION: Xaa represents a region of non-similarity

<400> SEQUENCE: 21

```
Lys Leu Ala Gly Arg Gly Gly Xaa Cys Leu
1               5                  10
```

<210> SEQ ID NO 22
<211> LENGTH: 17
<212> TYPE: PRT
<213> ORGANISM: Artificial Sequence
<220> FEATURE:
<223> OTHER INFORMATION: Region of similarity between P51BP4_596 and
      Homo sapiens SAM domain and HD domain 1 (SAMHD1), RefSeqGene
      (LRG_281) on chromosome 20

<400> SEQUENCE: 22

```
Asn Thr Lys Ile Ser Arg Val Lys Leu Ala Gly Arg Gly Gly Val Cys
1               5                  10                  15

Leu
```

<210> SEQ ID NO 23
<211> LENGTH: 21
<212> TYPE: PRT
<213> ORGANISM: Artificial Sequence
<220> FEATURE:
<223> OTHER INFORMATION: P51BP4_566

<400> SEQUENCE: 23

```
Gly Ile Ser Leu Leu Leu Val Leu Val Val Ile Val Val Leu Ala Lys
1               5                  10                  15

Pro Leu Asp Pro Leu
            20
```

<210> SEQ ID NO 24
<211> LENGTH: 655
<212> TYPE: PRT
<213> ORGANISM: Homo sapiens

<400> SEQUENCE: 24

Met Gly Thr Ser Pro Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Gln Pro Glu Gln Lys Ala Ser
            35                  40                  45

Asn Leu Ile Gly Thr Tyr Arg His Val Asp Arg Ala Thr Gly Gln Val
        50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
            115                 120                 125

Arg Glu Cys Thr Cys Pro Pro Gly Met Phe Gln Ser Asn Ala Thr Cys
130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
            195                 200                 205

Asn Val Cys Gly Thr Leu Pro Ser Phe Ser Ser Ser Thr Ser Pro Ser
210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
            275                 280                 285

Asn Lys Thr Leu Pro Asn Leu Gln Val Val Asn His Gln Gln Gly Pro
290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Leu Pro Trp
            340                 345                 350

Met Ile Val Leu Phe Leu Leu Leu Val Leu Val Val Ile Val Val Cys
            355                 360                 365

Ser Ile Arg Lys Ser Ser Arg Thr Leu Lys Lys Gly Pro Arg Gln Asp
370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
    450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
        515                 520                 525

Lys Leu Glu Asn Ser Ala Leu Leu Thr Val Glu Pro Ser Pro Gln Asp
    530                 535                 540

Lys Asn Lys Gly Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Phe Leu Asn
        595                 600                 605

Pro Glu Glu Leu Arg Val Ile Glu Glu Ile Pro Gln Ala Glu Asp Lys
    610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Pro Asp Leu Leu
                645                 650                 655

<210> SEQ ID NO 25
<211> LENGTH: 10
<212> TYPE: PRT
<213> ORGANISM: Artificial Sequence
<220> FEATURE:
<223> OTHER INFORMATION: Region of similarity between P51BP4_566 and
      tumor necrosis factor receptor superfamily member 21 precursor

<400> SEQUENCE: 25

Leu Leu Leu Val Leu Val Val Ile Val Val
1               5                   10

<210> SEQ ID NO 26
<211> LENGTH: 18
<212> TYPE: PRT
<213> ORGANISM: Artificial Sequence
<220> FEATURE:
<223> OTHER INFORMATION: P51BP3_283

<400> SEQUENCE: 26

Ser Gly Ala Pro Lys Leu Arg Pro Pro Lys Pro Asp Glu Leu Pro Lys
1               5                   10                  15

Asn Ser

<210> SEQ ID NO 27
<211> LENGTH: 420
<212> TYPE: PRT
<213> ORGANISM: Ochotona princeps

<400> SEQUENCE: 27

```
Met Leu Cys Thr His Ile Gln Asn Asp Pro Ser Ser Gly Glu Ser Arg
1               5                   10                  15

Asp His Ile Ser Glu Ser Ser Gly Thr Ser Asp Arg Ala Gln Arg Asn
            20                  25                  30

Phe Pro Leu Thr Val Ser Leu Gly Lys Ser Trp Thr Val Val Gly Trp
        35                  40                  45

Arg Glu Cys Ala Pro Cys Leu Leu Leu Leu Leu Pro Leu Leu Gly
    50                  55                  60

Ala Ser Val Thr Glu Pro Glu Pro Cys Gln Val Asp Asp Glu Asp Ile
65                  70                  75                  80

Arg Cys Val Cys Asn Phe Ser Asp Pro Gln Pro Asp Trp Ser Ser Ala
                85                  90                  95

Phe Gln Cys Met Pro Ala Val Glu Val Glu Met Trp Gly Gly His
            100                 105                 110

Ser Leu Glu Gln Phe Leu Gly Arg Ile Asp Pro Asn Ala Asp Pro Arg
        115                 120                 125

Gln His Ala Asp Leu Val Lys Ala Leu Arg Leu Arg Arg Leu Thr Val
    130                 135                 140

Gly Ala Ala Arg Val Pro Ala Val Ile Leu Leu Gly Val Leu Arg Met
145                 150                 155                 160

Leu Gly Tyr Ser Arg Leu Lys Glu Leu Arg Phe Arg Asp Ile Glu Val
                165                 170                 175

Thr Gly Pro Met Pro Pro Pro Gln Pro Gln Glu Ala Thr Gly Pro
            180                 185                 190

Ala Leu Ser Thr Leu Glu Leu His Asn Val Ser Trp Pro Thr Gly Gly
        195                 200                 205

Val Trp Leu Ser Glu Leu Gln Lys Trp Leu Lys Pro Gly Leu Lys Gln
    210                 215                 220

Leu Ser Ile Thr Gln Ala His Thr Leu Ala Phe Ser Cys Glu Gln Val
225                 230                 235                 240

Arg Pro Phe Ser Ser Leu Thr Thr Leu Asp Leu Ser Asp Asn Pro Gly
                245                 250                 255

Leu Asp Glu Gly Gly Leu Val Ala Ala Leu Cys Pro His Lys Phe Pro
            260                 265                 270

Ala Leu Gln Gln Leu Leu Leu Arg Asn Ala Gly Met Lys Thr Pro Gln
        275                 280                 285

Gly Val Cys Ala Ala Leu Asp Lys Ala Gly Val Gln Pro His His Leu
    290                 295                 300

Asp Leu Ser His Asn Ser Leu His Thr Asp Val Ser Gly Cys Leu Trp
305                 310                 315                 320

Pro Ser Val Leu Asn Ser Leu Asn Leu Ser Phe Thr Gly Leu Glu Gln
                325                 330                 335

Val Pro Lys Gly Leu Pro Ala Lys Leu Ser Leu Leu Asp Leu Arg Cys
            340                 345                 350

Asn Lys Leu Val Arg Ala Pro Gln Pro Asp Glu Leu Pro Lys Val Gly
        355                 360                 365
```

```
Thr Val Leu Leu Asp Gly Asn Pro Phe Gln Val Pro Gly Ala Ala Lys
        370                 375                 380
Gln Glu Asp Leu Thr Gly Ser Gly Val Leu Pro Ala Cys Ala His Leu
385                 390                 395                 400
Pro Leu Ala Met Gly Val Ser Gly Thr Leu Ala Leu Leu Gln Gly Val
                405                 410                 415
Arg Gly Phe Ala
        420

<210> SEQ ID NO 28
<211> LENGTH: 346
<212> TYPE: DNA
<213> ORGANISM: Homo sapiens

<400> SEQUENCE: 28
cggccaggaa attgaaactt ggcgcattgg atatggtccc gcaggggaaa gttgaaaatt      60
tataaccaag cataatatag caaggactac cccctatacc ttctgcataa tgaattaact    120
agaaataact ttgcaaggag agccaaagct aagaccccg aaaccagacg agctacctaa     180
gaacagctaa aagagcacac ccgtctatgt agcaaaatag tgggaagatt tataggtaga    240
ggcgacaaac ctaccgagcc tggtgatagc tggttgtcca agatagaatc ttagttcaac    300
tttaaatttg cccacagaac cctctaaatc cccttgtaaa tttaac                    346

<210> SEQ ID NO 29
<211> LENGTH: 13
<212> TYPE: PRT
<213> ORGANISM: Artificial Sequence
<220> FEATURE:
<223> OTHER INFORMATION: Region of similarity between P51BP3_283 and
      PREDICTED monocyte differentiation antigen CD14
<220> FEATURE:
<221> NAME/KEY: Xaa
<222> LOCATION: (3)..(3)
<223> OTHER INFORMATION: Xaa represents a region of non-similarity
<220> FEATURE:
<221> NAME/KEY: Xaa
<222> LOCATION: (5)..(5)
<223> OTHER INFORMATION: Xaa represents a region of non-similarity
<220> FEATURE:
<221> NAME/KEY: Xaa
<222> LOCATION: (7)..(7)
<223> OTHER INFORMATION: Xaa represents a region of non-similarity

<400> SEQUENCE: 29

Lys Leu Xaa Arg Xaa Pro Xaa Pro Asp Glu Leu Pro Lys
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Region of similarity between P51BP3_283 and
      Homo sapiens hypoxia inducable gene-14
<220> FEATURE:
<221> NAME/KEY: Xaa
<222> LOCATION: (2)..(2)
<223> OTHER INFORMATION: Xaa denotes a region of non-similarity

<400> SEQUENCE: 30

Gly Xaa Pro Lys Leu Arg Pro Pro Lys Pro Asp Glu Leu Pro Lys Asn
1               5                   10                  15

Ser
```

```
<210> SEQ ID NO 31
<211> LENGTH: 130
<212> TYPE: PRT
<213> ORGANISM: Artificial Sequence
<220> FEATURE:
<223> OTHER INFORMATION: P51BP3_47

<400> SEQUENCE: 31

Ser Ala Lys Tyr Lys Glu Thr Arg Leu Lys Glu Lys Glu Asp Ala Leu
1               5                   10                  15

Thr Arg Thr Glu Leu Glu Thr Leu Gln Lys Gln Lys Val Lys Lys
            20                  25                  30

Pro Lys Pro Glu Phe Pro Val Tyr Thr Pro Leu Glu Thr Thr Tyr Ile
            35                  40                  45

Gln Ser Tyr Asp His Gly Thr Ser Ile Glu Glu Ile Glu Glu Gln Met
        50                  55                  60

Asp Asp Trp Leu Glu Asn Arg Asn Arg Thr Gln Lys Lys Gln Ala Pro
65                  70                  75                  80

Glu Trp Thr Glu Glu Asp Leu Ser Gln Leu Thr Arg Ser Met Val Lys
                85                  90                  95

Phe Pro Gly Gly Thr Pro Gly Arg Trp Glu Lys Ile Ala His Glu Leu
            100                 105                 110

Gly Arg Ser Val Thr Asp Val Thr Thr Lys Ala Lys Leu Ala Ala Ala
            115                 120                 125

Leu Glu
    130

<210> SEQ ID NO 32
<211> LENGTH: 554
<212> TYPE: PRT
<213> ORGANISM: Homo sapiens

<400> SEQUENCE: 32

Met Thr Ala Pro Cys Ser Gln Pro Ala Gln Leu Pro Gly Arg Arg Gln
1               5                   10                  15

Leu Gly Leu Val Pro Phe Pro Pro Pro Pro Arg Thr Pro Leu Leu
            20                  25                  30

Trp Leu Leu Leu Leu Leu Ala Ala Val Ala Pro Ala Arg Gly Trp
            35                  40                  45

Glu Ser Gly Asp Leu Glu Leu Phe Asp Leu Val Glu Glu Val Gln Leu
        50                  55                  60

Asn Phe Tyr Gln Phe Leu Gly Val Gln Gln Asp Ala Ser Ser Ala Asp
65                  70                  75                  80

Ile Arg Lys Ala Tyr Arg Lys Leu Ser Leu Thr Leu His Pro Asp Lys
                85                  90                  95

Asn Lys Asp Glu Asn Ala Glu Thr Gln Phe Arg Gln Leu Val Ala Ile
            100                 105                 110

Tyr Glu Val Leu Lys Asp Asp Glu Arg Arg Gln Arg Tyr Asp Asp Ile
            115                 120                 125

Leu Ile Asn Gly Leu Pro Asp Trp Arg Gln Pro Val Phe Tyr Tyr Arg
        130                 135                 140

Arg Val Arg Lys Met Ser Asn Ala Glu Leu Ala Leu Leu Leu Phe Ile
145                 150                 155                 160

Ile Leu Thr Val Gly His Tyr Ala Val Val Trp Ser Ile Tyr Leu Glu
                165                 170                 175

Lys Gln Leu Asp Glu Leu Leu Ser Arg Lys Lys Arg Glu Lys Lys Lys
            180                 185                 190
```

Lys Thr Gly Ser Lys Ser Val Asp Val Ser Lys Leu Gly Ala Ser Glu
            195                 200                 205

Lys Asn Glu Arg Leu Leu Met Lys Pro Gln Trp His Asp Leu Leu Pro
        210                 215                 220

Cys Lys Leu Gly Ile Trp Phe Cys Leu Thr Leu Lys Ala Leu Pro His
225                 230                 235                 240

Leu Ile Gln Asp Ala Gly Gln Phe Tyr Ala Lys Tyr Lys Glu Thr Arg
                245                 250                 255

Leu Lys Glu Lys Glu Asp Ala Leu Thr Arg Thr Glu Leu Glu Thr Leu
            260                 265                 270

Gln Lys Gln Lys Val Lys Lys Pro Lys Pro Glu Phe Pro Val Tyr
        275                 280                 285

Thr Pro Leu Glu Thr Thr Tyr Ile Gln Ser Tyr Asp His Gly Thr Ser
    290                 295                 300

Ile Glu Glu Ile Glu Glu Gln Met Asp Asp Trp Leu Glu Asn Arg Asn
305                 310                 315                 320

Arg Thr Gln Lys Lys Gln Ala Pro Glu Trp Thr Glu Asp Leu Ser
                325                 330                 335

Gln Leu Thr Arg Ser Met Val Lys Phe Pro Gly Gly Thr Pro Gly Arg
            340                 345                 350

Trp Glu Lys Ile Ala His Glu Leu Gly Arg Ser Val Thr Asp Val Thr
        355                 360                 365

Thr Lys Ala Lys Gln Leu Lys Asp Ser Val Thr Cys Ser Pro Gly Met
    370                 375                 380

Val Arg Leu Ser Glu Leu Lys Ser Thr Val Gln Asn Ser Arg Pro Ile
385                 390                 395                 400

Lys Thr Ala Thr Thr Leu Pro Asp Asp Met Ile Thr Gln Arg Glu Asp
                405                 410                 415

Ala Glu Gly Val Ala Ala Glu Glu Gln Glu Gly Asp Ser Gly Glu
            420                 425                 430

Gln Glu Thr Gly Ala Thr Asp Ala Arg Pro Arg Arg Lys Pro Ala
        435                 440                 445

Arg Leu Leu Glu Ala Thr Ala Lys Pro Glu Pro Glu Glu Lys Ser Arg
    450                 455                 460

Ala Lys Arg Gln Lys Asp Phe Asp Ile Ala Glu Gln Asn Glu Ser Ser
465                 470                 475                 480

Asp Glu Glu Ser Leu Arg Lys Glu Arg Ala Arg Ser Ala Glu Glu Pro
                485                 490                 495

Trp Thr Gln Asn Gln Gln Lys Leu Leu Glu Leu Ala Leu Gln Gln Tyr
            500                 505                 510

Pro Arg Gly Ser Ser Asp Arg Trp Asp Lys Ile Ala Arg Cys Val Pro
        515                 520                 525

Ser Lys Ser Lys Glu Asp Cys Ile Ala Arg Tyr Lys Leu Leu Val Glu
    530                 535                 540

Leu Val Gln Lys Lys Lys Gln Ala Lys Ser
545                 550

<210> SEQ ID NO 33
<211> LENGTH: 123
<212> TYPE: PRT
<213> ORGANISM: Artificial Sequence
<220> FEATURE:
<223> OTHER INFORMATION: Region of similarity between P51BP3_47 and dnaJ
      homolog subfamily C member 1 precursor

```
<400> SEQUENCE: 33

Ala Lys Tyr Lys Glu Thr Arg Leu Lys Glu Lys Glu Asp Ala Leu Thr
1               5                   10                  15

Arg Thr Glu Leu Glu Thr Leu Gln Lys Gln Lys Lys Val Lys Lys Pro
            20                  25                  30

Lys Pro Glu Phe Pro Val Tyr Thr Pro Leu Glu Thr Thr Tyr Ile Gln
        35                  40                  45

Ser Tyr Asp His Gly Thr Ser Ile Glu Glu Ile Glu Glu Gln Met Asp
    50                  55                  60

Asp Trp Leu Glu Asn Arg Asn Arg Thr Gln Lys Lys Gln Ala Pro Glu
65                  70                  75                  80

Trp Thr Glu Glu Asp Leu Ser Gln Leu Thr Arg Ser Met Val Lys Phe
                85                  90                  95

Pro Gly Gly Thr Pro Gly Arg Trp Glu Lys Ile Ala His Glu Leu Gly
            100                 105                 110

Arg Ser Val Thr Asp Val Thr Thr Lys Ala Lys
            115                 120

<210> SEQ ID NO 34
<211> LENGTH: 25
<212> TYPE: PRT
<213> ORGANISM: Artificial Sequence
<220> FEATURE:
<223> OTHER INFORMATION: P197BP4_885

<400> SEQUENCE: 34

Ala Lys Phe Pro Pro Pro Pro Glu Arg Arg Ser Gly Cys Thr Ala Leu
1               5                   10                  15

Ala Pro Ser Phe Arg Leu Val Leu Ser
            20                  25

<210> SEQ ID NO 35
<211> LENGTH: 655
<212> TYPE: PRT
<213> ORGANISM: Melopsittacus undulatus

<400> SEQUENCE: 35

Met Glu Gln Thr Cys Asp Asp Ile Asp Glu Met Phe Ser Asn Leu Leu
1               5                   10                  15

Gly Glu Met Asp Met Leu Thr Gln Ser Leu Gly Val Glu Thr Val Gln
            20                  25                  30

Pro Pro Ser Pro Arg Val Ser Asn Asn Glu Phe Ser Phe Thr Val Gly
            35                  40                  45

Phe Lys Asp Leu Asn Glu Ser Leu Asn Ala Leu Glu Asp Lys Asp Leu
    50                  55                  60

Asp Ala Leu Met Ala Asp Leu Val Ala Asp Ile Asn Asp Val Glu Gln
65                  70                  75                  80

Arg Thr Leu Gln Ala Gln Lys Ser Ser Gly Ser Gln Gln Asn Ile Leu
                85                  90                  95

Thr Gln Pro Ser Thr Val Leu Asp Ser Asp Ile Tyr Thr Lys Leu Ser
            100                 105                 110

Pro Ile Thr Gly His Phe Glu Asp Asp Leu Pro Pro Pro Pro Pro Asp
            115                 120                 125

Pro Asp Leu Asp Leu Pro Pro Pro Pro Pro Pro Pro Ala Glu Pro
    130                 135                 140

Leu Thr Gln Glu Glu Arg Glu Ala Gln Ala Lys Ala Asp Lys Ile Lys
145                 150                 155                 160
```

```
Leu Ala Leu Glu Lys Leu Lys Glu Ala Lys Val Lys Leu Val Val
            165                 170                 175

Lys Val His Met Tyr Asp Asn Ser Ser Lys Ser Leu Met Val Asp Glu
            180                 185                 190

Arg Gln Val Thr Arg Asp Val Leu Asp Asn Leu Phe Glu Lys Thr His
            195                 200                 205

Cys Asp Cys Asn Val Asp Trp Cys Leu Tyr Glu Ile Tyr Pro Glu Leu
210                 215                 220

Gln Ile Glu Arg Phe Phe Glu Asp His Glu Asn Val Val Glu Val Leu
225                 230                 235                 240

Ser Asp Trp Thr Arg Asp Thr Val Asn Lys Ile Met Phe Leu Glu Lys
            245                 250                 255

Ser Glu Lys Tyr Ala Leu Phe Lys Asn Pro Gln Asn Phe Tyr Leu Ala
            260                 265                 270

Ser Lys Gly Arg Asn Glu Asn Lys Glu Met Asn Asp Lys Ser Lys Glu
            275                 280                 285

Ala Leu Leu Glu Glu Ser Phe Cys Gly Thr Ser Val Val Val Pro Glu
            290                 295                 300

Leu Glu Gly Ala Leu Tyr Leu Lys Glu Asp Gly Lys Lys Ser Trp Lys
305                 310                 315                 320

Arg Arg Tyr Phe Leu Leu Arg Ala Ser Gly Ile Tyr Tyr Val Pro Lys
            325                 330                 335

Gly Lys Thr Lys Thr Ser Arg Asp Leu Ala Cys Phe Ile Gln Phe Glu
            340                 345                 350

Asn Met Asn Val Tyr Tyr Gly Ser Gln His Lys Val Lys Tyr Lys Ala
            355                 360                 365

Pro Thr Asp His Cys Phe Val Leu Lys His Pro Gln Ile Gln Lys Glu
            370                 375                 380

Ser Gln Tyr Ile Lys Tyr Leu Cys Cys Asp Asp Gln Ala Thr Leu His
385                 390                 395                 400

Gln Trp Val Thr Gly Ile Arg Ile Ala Lys Tyr Gly Lys Leu Leu Tyr
            405                 410                 415

Asp Asn Tyr Lys Cys Ala Val Lys Lys Ala Gly Leu Ser Ser Arg Trp
            420                 425                 430

Thr Asn Gln Gly Ser Val Glu Pro Ala Thr Pro Ala Gly Ser Leu Pro
            435                 440                 445

Ala Gly Ala Val Gln Ser Asn Gly Gln Val Pro Gln Ile Val Cys His
            450                 455                 460

Ala Ser Ala Glu Leu Pro Glu Thr Gln Lys Lys Val Asp Thr Ser Glu
465                 470                 475                 480

Ala Lys Ser Asn Asn Ile Ser Ala Pro Gly Leu Ala Gln Pro Val Met
            485                 490                 495

Arg Pro Gln Lys Phe Gln Ser Lys Arg Asn Ser Leu Gln Pro Pro Pro
            500                 505                 510

Pro Pro Glu Arg Arg Ser Ser Ala Val Ser Ala Ser Pro Ile Leu Pro
            515                 520                 525

Ser Lys Ile Lys Arg Asp Ser Gly Ile Phe Leu Thr Asp Pro Asp Thr
            530                 535                 540

Phe Pro Ala Pro Pro Val Leu Lys Val Asp Phe Pro Pro Pro Pro Pro
545                 550                 555                 560

Ser Asp Phe Cys Glu Pro Pro Asp Phe Val Pro Pro Pro Pro Pro Pro
            565                 570                 575
```

-continued

```
Pro Ser Ser Ser Asn Gly Asp Val Pro Leu Pro Pro Pro Pro
            580                 585                 590

Pro Val Ser Thr Lys Pro Pro Leu Thr Lys Pro Val Pro Leu
        595                 600                 605

Pro Pro Lys Arg Leu Glu Asn Thr Gly Gln Ala Gly Glu Pro Gln Ser
    610                 615                 620

Ala Gly Pro Phe Pro Ile Gly Gly Gly Lys Gln Ala Asp Phe Met
625                 630                 635                 640

Ser Asp Leu Met Lys Val Leu Glu Lys Lys Arg Gly Ser Asn Ser
                645                 650                 655

<210> SEQ ID NO 36
<211> LENGTH: 830
<212> TYPE: DNA
<213> ORGANISM: Homo sapiens

<400> SEQUENCE: 36
cccccccgag cgccgctccg gctgcaccgc gctcgctccg agtttcaggc tcgtgctaag      60
ctagcgccgt cgtcgtctcc cttcagtcgc catcatgatt atctaccggg acctcatcag     120
ccacgatgag atgttctccg acatctacaa gatccgggag atcgcggacg ggttgtgcct     180
ggaggtggag gggaagatgg tcagtaggac agaaggtaac attgatgact cgctcattgg     240
tggaaatgcc tccgctgaag gccccgaggg cgaaggtacc gaaagcacag taatcactgg     300
tgtcgatatt gtcatgaacc atcacctgca ggaaacaagt ttcacaaaag aagcctacaa     360
gaagtacatc aaagattaca tgaaatcaat caagggaaaa cttgaagaac agagaccaga     420
aagagtaaaa cctttatga cagggctgc agaacaaatc aagcacatcc ttgctaattt     480
caaaaactac cagttctta ttggtgaaaa catgaatcca gatggcatgg ttgctctatt     540
ggactaccgt gaggatggtg tgaccccata tatgattttc tttaaggatg gtttagaaat     600
ggaaaaatgt taacaaatgt ggcaattatt ttggatctat cacctgtcat cataactggc     660
ttctgcttgt catccacaca acaccaggac ttaagacaaa tgggactgat gtcatcttga     720
gctcttcatt tatttgact gtgattat tggagtggag gcattgttt taagaaaaac     780 atgtcatgta ggttgtctaa aaataaaatg catttaaact catttgagag                830

<210> SEQ ID NO 37
<211> LENGTH: 8
<212> TYPE: PRT
<213> ORGANISM: Artificial Sequence
<220> FEATURE:
<223> OTHER INFORMATION: Region of similarity between P197BP4_885 and
      PREDICTED: amyloid beta A4 precursor protein-binding family B
      member 1-interacting protein

<400> SEQUENCE: 37

Pro Pro Pro Pro Glu Arg Arg Ser
1               5

<210> SEQ ID NO 38
<211> LENGTH: 15
<212> TYPE: PRT
<213> ORGANISM: Artificial Sequence
<220> FEATURE:
<223> OTHER INFORMATION: Region of similarity between P197BP4_885 and
      Human mRNA for translationally controlled tumor protein

<400> SEQUENCE: 38

Pro Pro Glu Arg Arg Ser Gly Cys Thr Ala Leu Ala Pro Ser Phe
1               5                   10                  15
```

<210> SEQ ID NO 39
<211> LENGTH: 17
<212> TYPE: PRT
<213> ORGANISM: Artificial Sequence
<220> FEATURE:
<223> OTHER INFORMATION: P51BP4_577

<400> SEQUENCE: 39

Ser Gly Lys Thr Ile Leu Gln Glu Leu Arg Arg Leu His His Ile Pro
1               5                   10                  15

Arg

<210> SEQ ID NO 40
<211> LENGTH: 223
<212> TYPE: PRT
<213> ORGANISM: Homo sapiens

<400> SEQUENCE: 40

Met Lys Phe Val Pro Cys Leu Leu Leu Val Thr Leu Ser Cys Leu Gly
1               5                   10                  15

Thr Leu Gly Gln Ala Pro Arg Gln Lys Gln Gly Ser Thr Gly Glu Glu
            20                  25                  30

Phe His Phe Gln Thr Gly Gly Arg Asp Ser Cys Thr Met Arg Pro Ser
        35                  40                  45

Ser Leu Gly Gln Gly Ala Gly Glu Val Trp Leu Arg Val Asp Cys Arg
    50                  55                  60

Asn Thr Asp Gln Thr Tyr Trp Cys Glu Tyr Arg Gly Gln Pro Ser Met
65                  70                  75                  80

Cys Gln Ala Phe Ala Ala Asp Pro Lys Pro Tyr Trp Asn Gln Ala Leu
                85                  90                  95

Gln Glu Leu Arg Arg Leu His His Ala Cys Gln Gly Ala Pro Val Leu
            100                 105                 110

Arg Pro Ser Val Cys Arg Glu Ala Gly Pro Gln Ala His Met Gln Gln
        115                 120                 125

Val Thr Ser Ser Leu Lys Gly Ser Pro Glu Pro Asn Gln Gln Pro Glu
    130                 135                 140

Ala Gly Thr Pro Ser Leu Arg Pro Lys Ala Thr Val Lys Leu Thr Glu
145                 150                 155                 160

Ala Thr Gln Leu Gly Lys Asp Ser Met Glu Glu Leu Gly Lys Ala Lys
                165                 170                 175

Pro Thr Thr Arg Pro Thr Ala Lys Pro Thr Gln Pro Gly Pro Arg Pro
            180                 185                 190

Gly Gly Asn Glu Glu Ala Lys Lys Lys Ala Trp Glu His Cys Trp Lys
        195                 200                 205

Pro Phe Gln Ala Leu Cys Ala Phe Leu Ile Ser Phe Phe Arg Gly
    210                 215                 220

<210> SEQ ID NO 41
<211> LENGTH: 9
<212> TYPE: PRT
<213> ORGANISM: Artificial Sequence
<220> FEATURE:
<223> OTHER INFORMATION: Region of similarity between P51BP4_577 and
      fibroblast growth factor-binding protein 2 precursor

<400> SEQUENCE: 41

Leu Gln Glu Leu Arg Arg Leu His His
1               5

<210> SEQ ID NO 42
<211> LENGTH: 103
<212> TYPE: PRT
<213> ORGANISM: Artificial Sequence
<220> FEATURE:
<223> OTHER INFORMATION: P197BP4_755

<400> SEQUENCE: 42

```
Asn Glu Ala Asn Arg Phe Ser Phe Ile Leu Val Leu Arg Val Cys Tyr
1               5                   10                  15

Asn Phe Leu Phe Leu Trp Ser Leu Glu Gly Ser Cys Leu Ile Glu Arg
            20                  25                  30

Lys Glu Thr Asn Arg Lys Phe Tyr Cys Gln Asp Ile Arg Ala Tyr Asp
        35                  40                  45

Ile Leu Phe Gly Asp Thr Pro Arg Pro Ala Gln Ala Glu Leu Tyr Glu
    50                  55                  60

Ile Leu Asp Ser Phe Thr Glu Lys Tyr Glu Asn Glu Gly Gln Arg Ile
65                  70                  75                  80

Asn Ala Gly Pro Arg Glu Gln Arg Arg Leu Pro Thr Lys Thr Ile Val
                85                  90                  95

Gly Lys Ser Asp Leu Gln Ser
            100
```

<210> SEQ ID NO 43
<211> LENGTH: 227
<212> TYPE: PRT
<213> ORGANISM: Homo sapiens

<400> SEQUENCE: 43

```
Met Val Ser Asp Leu Val Ile Ile Leu Asn Tyr Asp Arg Ala Val Glu
1               5                   10                  15

Ala Phe Ala Lys Gly Gly Asn Leu Thr Leu Gly Gly Asn Leu Thr Val
            20                  25                  30

Ala Val Gly Pro Leu Gly Arg Asn Leu Glu Gly Asn Val Ala Leu Arg
        35                  40                  45

Ser Ser Ala Ala Val Phe Thr Tyr Cys Lys Ser Arg Gly Leu Phe Ala
    50                  55                  60

Gly Val Ser Leu Glu Gly Ser Cys Leu Ile Glu Arg Lys Glu Thr Asn
65                  70                  75                  80

Arg Lys Phe Tyr Cys Gln Asp Ile Arg Ala Tyr Asp Ile Leu Phe Gly
                85                  90                  95

Asp Thr Pro Arg Pro Ala Gln Ala Glu Asp Leu Tyr Glu Ile Leu Asp
            100                 105                 110

Ser Phe Thr Glu Lys Tyr Glu Asn Glu Gly Gln Arg Ile Asn Ala Arg
        115                 120                 125

Lys Ala Ala Arg Glu Gln Arg Lys Ser Ser Ala Lys Glu Leu Pro Pro
    130                 135                 140

Lys Pro Leu Ser Arg Pro Gln Gln Ser Ser Ala Pro Val Gln Leu Asn
145                 150                 155                 160

Ser Gly Ser Gln Ser Asn Leu Asn Gln Pro Ile Glu Val Thr Ala Leu
                165                 170                 175

Tyr Ser Phe Glu Gly Gln Gln Pro Gly Asp Leu Asn Phe Gln Ala Gly
            180                 185                 190

Asp Arg Ile Thr Val Ile Ser Lys Thr Asp Ser His Phe Asp Trp Trp
        195                 200                 205
```

-continued

```
Glu Gly Lys Leu Arg Gly Gln Thr Gly Ile Phe Pro Ala Asn Tyr Val
    210                 215                 220

Thr Met Asn
225

<210> SEQ ID NO 44
<211> LENGTH: 79
<212> TYPE: PRT
<213> ORGANISM: Artificial Sequence
<220> FEATURE:
<223> OTHER INFORMATION: Region of similarity between P197BP4_755 and
      SH3 domain-containing YSC84-like protein 1 isoform 3
<220> FEATURE:
<221> NAME/KEY: Xaa
<222> LOCATION: (40)..(40)
<223> OTHER INFORMATION: Xaa denotes a region of non-similarity
<220> FEATURE:
<221> NAME/KEY: Xaa
<222> LOCATION: (62)..(65)
<223> OTHER INFORMATION: Xaa denotes a region of non-similarity
<220> FEATURE:
<221> NAME/KEY: Xaa
<222> LOCATION: (70)..(73)
<223> OTHER INFORMATION: Xaa denotes a region of non-similarity
<220> FEATURE:
<221> NAME/KEY: Xaa
<222> LOCATION: (75)..(78)
<223> OTHER INFORMATION: Xaa denotes a region of non-similarity

<400> SEQUENCE: 44

Ser Leu Glu Gly Ser Cys Leu Ile Glu Arg Lys Glu Thr Asn Arg Lys
1               5                   10                  15

Phe Tyr Cys Gln Asp Ile Arg Ala Tyr Asp Ile Leu Phe Gly Asp Thr
            20                  25                  30

Pro Arg Pro Ala Gln Ala Glu Xaa Leu Tyr Glu Ile Leu Asp Ser Phe
        35                  40                  45

Thr Glu Lys Tyr Glu Asn Glu Gly Gln Arg Ile Asn Ala Xaa Xaa Xaa
    50                  55                  60

Xaa Arg Glu Gln Arg Xaa Xaa Xaa Xaa Lys Xaa Xaa Xaa Xaa Lys
65                  70                  75

<210> SEQ ID NO 45
<211> LENGTH: 9
<212> TYPE: PRT
<213> ORGANISM: Artificial Sequence
<220> FEATURE:
<223> OTHER INFORMATION: P51BP3_174

<400> SEQUENCE: 45

Ile Gln His Gln His Leu Gly Gln Ile
1               5

<210> SEQ ID NO 46
<211> LENGTH: 105
<212> TYPE: PRT
<213> ORGANISM: Mycobacterium tuberculosis]

<400> SEQUENCE: 46

Met Asp Val Met Asp Lys Ser Cys Val Gln Glu Cys Pro Val Asp Cys
1               5                   10                  15

Ile Tyr Glu Gly Ala Arg Met Leu Tyr Ile Asn Pro Asp Glu Cys Val
            20                  25                  30

Asp Cys Gly Ala Cys Lys Pro Ala Cys Arg Val Glu Ala Ile Tyr Trp
        35                  40                  45

Glu Gly Asp Leu Pro Asp Asp Gln His Gln His Leu Gly Asp Asn Ala
```

```
                    50                  55                  60

Ala Phe Phe His Gln Val Leu Pro Gly Arg Val Ala Pro Leu Gly Ser
 65                  70                  75                  80

Pro Gly Gly Ala Ala Ala Val Gly Pro Ile Gly Val Asp Thr Pro Leu
                 85                  90                  95

Val Ala Ala Ile Pro Val Glu Cys Pro
            100                 105

<210> SEQ ID NO 47
<211> LENGTH: 6
<212> TYPE: PRT
<213> ORGANISM: Artificial Sequence
<220> FEATURE:
<223> OTHER INFORMATION: Region of similarity between P51BP3_174 and
      ferredoxin

<400> SEQUENCE: 47

Gln His Gln His Leu Gly
1               5

<210> SEQ ID NO 48
<211> LENGTH: 160
<212> TYPE: PRT
<213> ORGANISM: Artificial Sequence
<220> FEATURE:
<223> OTHER INFORMATION: P51BP4_610

<400> SEQUENCE: 48

Leu Tyr Asp Pro His Pro Asn Pro Ile Glu Val Arg Asn Tyr Ser Arg
1               5                  10                  15

Leu Lys Pro Gly Tyr Arg Trp Glu Arg Gln Leu Val Phe Arg Ser Lys
                20                  25                  30

Leu Thr Met His Thr Ala Phe Asp Arg Lys Asp Asn Ala His Pro Ala
            35                  40                  45

Glu Val Thr Ala Leu Gly Ile Ser Lys Asp His Ser Arg Ile Leu Val
        50                  55                  60

Gly Asp Ser Arg Gly Arg Val Phe Ser Trp Ser Val Ser Asp Gln Pro
 65                  70                  75                  80

Gly Arg Ser Ala Ala Asp His Trp Val Lys Asp Glu Gly Gly Asp Ser
                85                  90                  95

Cys Ser Gly Cys Ser Val Arg Phe Ser Leu Thr Glu Arg Arg His His
            100                 105                 110

Cys Arg Asn Cys Gly Gln Leu Phe Cys Gln Lys Cys Ser Arg Phe Gln
        115                 120                 125

Ser Glu Ile Lys Arg Leu Lys Ile Ser Pro Val Arg Val Cys Asn
    130                 135                 140

Cys Tyr Tyr Asn Leu Gln His Glu Arg Gly Ser Gly Pro Arg Asn Cys
145                 150                 155                 160

<210> SEQ ID NO 49
<211> LENGTH: 437
<212> TYPE: PRT
<213> ORGANISM: Homo sapiens

<400> SEQUENCE: 49

Pro Lys Leu Val Ile Thr Gly Gly Thr Ser Thr Val Val Cys Val Trp
1               5                  10                  15

Glu Met Gly Thr Ser Lys Glu Lys Ala Lys Val Thr Val Leu Lys Gln
                20                  25                  30
```

```
Ala Leu Leu Gly His Thr Asp Thr Val Thr Cys Ala Thr Ala Ser Leu
         35                  40                  45

Ala Tyr His Ile Ile Val Ser Gly Ser Arg Asp Arg Thr Cys Ile Ile
 50                  55                  60

Trp Asp Leu Asn Lys Leu Ser Phe Leu Thr Gln Leu Arg Gly His Arg
 65                  70                  75                  80

Ala Pro Val Ser Ala Leu Cys Ile Asn Glu Leu Thr Gly Asp Ile Val
                 85                  90                  95

Ser Cys Ala Gly Thr Tyr Ile His Val Trp Ser Ile Asn Gly Asn Pro
             100                 105                 110

Ile Val Ser Val Asn Thr Phe Thr Gly Arg Ser Gln Gln Ile Ile Cys
         115                 120                 125

Cys Cys Met Ser Glu Met Asn Glu Trp Asp Thr Gln Asn Val Ile Val
130                 135                 140

Thr Gly His Ser Asp Gly Val Val Arg Phe Trp Arg Met Glu Phe Leu
145                 150                 155                 160

Gln Val Pro Glu Thr Pro Ala Pro Glu Pro Ala Glu Val Leu Glu Met
                 165                 170                 175

Gln Glu Asp Cys Pro Glu Ala Gln Ile Gly Gln Glu Ala Gln Asp Glu
             180                 185                 190

Asp Ser Ser Asp Ser Glu Ala Asp Glu Gln Ser Ile Ser Gln Asp Pro
         195                 200                 205

Lys Asp Thr Pro Ser Gln Pro Ser Ser Thr Ser His Arg Pro Arg Ala
         210                 215                 220

Ala Ser Cys Arg Ala Thr Ala Ala Trp Cys Thr Asp Ser Gly Ser Asp
225                 230                 235                 240

Asp Ser Arg Arg Trp Ser Asp Gln Leu Ser Leu Asp Glu Lys Asp Gly
                 245                 250                 255

Phe Ile Phe Val Asn Tyr Ser Glu Gly Gln Thr Arg Ala His Leu Gln
             260                 265                 270

Gly Pro Leu Ser His Pro His Pro Asn Pro Ile Glu Val Arg Asn Tyr
         275                 280                 285

Ser Arg Leu Lys Pro Gly Tyr Arg Trp Glu Arg Gln Leu Val Phe Arg
290                 295                 300

Ser Lys Leu Thr Met His Thr Ala Phe Asp Arg Lys Asp Asn Ala His
305                 310                 315                 320

Pro Ala Glu Val Thr Ala Leu Gly Ile Ser Lys Asp His Ser Arg Ile
                 325                 330                 335

Leu Val Gly Asp Ser Arg Gly Arg Val Phe Ser Trp Ser Val Ser Asp
             340                 345                 350

Gln Pro Gly Arg Ser Ala Ala Asp His Trp Val Lys Asp Glu Gly Gly
         355                 360                 365

Asp Ser Cys Ser Gly Cys Ser Val Arg Phe Ser Leu Thr Glu Arg Arg
         370                 375                 380

His His Cys Arg Asn Cys Gly Gln Leu Phe Cys Gln Lys Cys Ser Arg
385                 390                 395                 400

Phe Gln Ser Glu Ile Lys Arg Leu Lys Ile Ser Ser Pro Val Arg Val
                 405                 410                 415

Cys Gln Asn Cys Tyr Tyr Asn Leu Gln His Glu Arg Gly Ser Glu Asp
             420                 425                 430

Gly Pro Arg Asn Cys
         435
```

-continued

```
<210> SEQ ID NO 50
<211> LENGTH: 163
<212> TYPE: PRT
<213> ORGANISM: Artificial Sequence
<220> FEATURE:
<223> OTHER INFORMATION: Region of similarity between P51BP4_610 WDFY3
      protein, partial
<220> FEATURE:
<221> NAME/KEY: Xaa
<222> LOCATION: (2)..(2)
<223> OTHER INFORMATION: Xaa denotes a region of non-similarity
<220> FEATURE:
<221> NAME/KEY: Xaa
<222> LOCATION: (33)..(34)
<223> OTHER INFORMATION: Xaa denotes a region of non-similarity
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: Xaa
<222> LOCATION: (57)..(58)
<223> OTHER INFORMATION: Xaa denotes a region of non-similarity
<220> FEATURE:
<221> NAME/KEY: misc_feature
<222> LOCATION: (157)..(158)
<223> OTHER INFORMATION: Xaa can be any naturally occurring amino acid

<400> SEQUENCE: 50

Leu Xaa Pro His Pro Asn Pro Ile Glu Val Arg Asn Tyr Ser Arg Leu
1               5                   10                  15

Lys Pro Gly Tyr Arg Trp Glu Arg Gln Leu Val Phe Arg Ser Lys Leu
            20                  25                  30

Thr Met Xaa Xaa His Thr Ala Phe Asp Arg Lys Asp Asn Ala His Pro
        35                  40                  45

Ala Glu Val Thr Ala Leu Gly Ile Ser Lys Asp His Ser Arg Ile Leu
    50                  55                  60

Val Gly Asp Ser Arg Gly Arg Val Phe Ser Trp Ser Val Ser Asp Gln
65                  70                  75                  80

Pro Gly Arg Ser Ala Ala Asp His Trp Val Lys Asp Glu Gly Gly Asp
                85                  90                  95

Ser Cys Ser Gly Cys Ser Val Arg Phe Ser Leu Thr Glu Arg Arg His
            100                 105                 110

His Cys Arg Asn Cys Gly Gln Leu Phe Cys Gln Lys Cys Ser Arg Phe
        115                 120                 125

Gln Ser Glu Ile Lys Arg Leu Lys Ile Ser Ser Pro Val Arg Val Cys
    130                 135                 140

Asn Cys Tyr Tyr Asn Leu Gln His Glu Arg Gly Ser Xaa Xaa Gly Pro
145                 150                 155                 160

Arg Asn Cys

<210> SEQ ID NO 51
<211> LENGTH: 27
<212> TYPE: PRT
<213> ORGANISM: Artificial Sequence
<220> FEATURE:
<223> OTHER INFORMATION: P51BP3_266

<400> SEQUENCE: 51

Val Asp Lys Ser Val Leu Leu Ser Leu Gly Arg Lys Lys Tyr Gly Ala
1               5                   10                  15

Val Gly Ser Leu Ser Gln Ser Thr Gly Gly His
            20                  25
```

-continued

<210> SEQ ID NO 52
<211> LENGTH: 961
<212> TYPE: PRT
<213> ORGANISM: Mycobacterium tuberculosis]

<400> SEQUENCE: 52

Met Val Pro Gly Glu Val His Met Ser Asp Thr Pro Ser Gly Pro His
1               5                   10                  15

Pro Ile Ile Pro Arg Thr Ile Arg Leu Ala Ala Ile Pro Ile Leu Leu
            20                  25                  30

Cys Trp Leu Gly Phe Thr Val Phe Val Ser Val Ala Val Pro Pro Leu
        35                  40                  45

Glu Ala Ile Gly Glu Thr Arg Ala Val Ala Val Ala Pro Asp Asp Ala
    50                  55                  60

Gln Ser Met Arg Ala Met Arg Arg Ala Gly Lys Val Phe Asn Glu Phe
65                  70                  75                  80

Asp Ser Asn Ser Ile Ala Met Val Val Leu Glu Ser Asp Gln Pro Leu
                85                  90                  95

Gly Glu Lys Ala His Arg Tyr Tyr Asp His Leu Val Asp Thr Leu Val
            100                 105                 110

Leu Asp Gln Ser His Ile Gln His Ile Gln Asp Phe Trp Arg Asp Pro
        115                 120                 125

Leu Thr Ala Ala Gly Ala Val Ser Ala Asp Gly Lys Ala Ala Tyr Val
    130                 135                 140

Gln Leu Tyr Leu Ala Gly Asn Met Gly Glu Ala Leu Ala Asn Glu Ser
145                 150                 155                 160

Val Glu Ala Val Arg Lys Ile Val Ala Asn Ser Thr Pro Pro Glu Gly
                165                 170                 175

Ile Arg Thr Tyr Val Thr Gly Pro Ala Ala Leu Phe Ala Asp Gln Ile
            180                 185                 190

Ala Ala Gly Asp Arg Ser Met Lys Leu Ile Thr Gly Leu Thr Phe Ala
        195                 200                 205

Val Ile Thr Val Leu Leu Leu Val Tyr Arg Ser Ile Ala Thr Thr
    210                 215                 220

Leu Leu Ile Leu Pro Met Val Phe Ile Gly Leu Gly Ala Thr Arg Gly
225                 230                 235                 240

Thr Ile Ala Phe Leu Gly Tyr His Gly Met Val Gly Leu Ser Thr Phe
                245                 250                 255

Val Val Asn Ile Leu Thr Ala Leu Ala Ile Ala Ala Gly Thr Asp Tyr
            260                 265                 270

Ala Ile Phe Leu Val Gly Arg Tyr Gln Glu Ala Arg His Ile Gly Gln
        275                 280                 285

Asn Arg Glu Ala Ser Phe Tyr Thr Met Tyr Arg Gly Thr Ala Asn Val
    290                 295                 300

Ile Leu Gly Ser Gly Leu Thr Ile Ala Gly Ala Thr Tyr Cys Leu Ser
305                 310                 315                 320

Phe Ala Arg Leu Thr Leu Phe His Thr Met Gly Pro Pro Leu Ala Ile
                325                 330                 335

Gly Met Leu Val Ser Val Ala Ala Leu Thr Leu Ala Pro Ala Ile
            340                 345                 350

Ile Ala Ile Ala Gly Arg Phe Gly Leu Leu Asp Pro Lys Arg Arg Leu
        355                 360                 365

Lys Thr Arg Gly Trp Arg Arg Val Gly Thr Ala Val Val Arg Trp Pro
    370                 375                 380

```
Gly Pro Ile Leu Ala Thr Ser Val Ala Leu Ala Val Gly Leu Leu
385                 390                 395                 400

Ala Leu Pro Gly Tyr Arg Pro Gly Tyr Asn Asp Arg Tyr Tyr Leu Arg
                405                 410                 415

Ala Gly Thr Pro Val Asn Arg Gly Tyr Ala Ala Ala Asp Arg His Phe
            420                 425                 430

Gly Pro Ala Arg Met Asn Pro Glu Met Leu Leu Val Glu Ser Asp Gln
        435                 440                 445

Asp Met Arg Asn Pro Ala Gly Met Leu Val Ile Asp Lys Ile Ala Lys
    450                 455                 460

Glu Val Leu His Val Ser Gly Val Glu Arg Val Gln Ala Ile Thr Arg
465                 470                 475                 480

Pro Gln Ala Val Pro Leu Glu His Ala Ser Ile Pro Phe Gln Ile Ser
                485                 490                 495

Met Met Gly Ala Thr Gln Thr Met Ser Leu Pro Tyr Met Arg Glu Arg
            500                 505                 510

Met Ala Asp Met Leu Thr Met Ser Asp Glu Met Leu Val Ala Ile Asn
        515                 520                 525

Ser Met Glu Gln Met Leu Asp Leu Val Gln Gln Leu Asn Asp Val Thr
    530                 535                 540

His Glu Met Ala Ala Thr Thr Arg Glu Ile Lys Ala Thr Thr Ser Glu
545                 550                 555                 560

Leu Arg Asp His Leu Ala Asp Ile Asp Asp Phe Val Arg Pro Leu Arg
                565                 570                 575

Ser Tyr Phe Tyr Trp Glu His His Cys Phe Asp Ile Pro Leu Cys Ser
            580                 585                 590

Ala Thr Arg Ser Leu Phe Asp Thr Leu Asp Gly Val Asp Thr Leu Thr
        595                 600                 605

Asp Gln Leu Arg Ala Leu Thr Asp Asp Met Asn Lys Met Glu Ala Leu
    610                 615                 620

Thr Pro Gln Phe Leu Ala Leu Leu Pro Pro Met Ile Thr Thr Met Lys
625                 630                 635                 640

Thr Met Arg Thr Met Met Leu Thr Met Arg Ser Thr Ile Ser Gly Val
                645                 650                 655

Gln Asp Gln Met Ala Asp Met Gln Asp His Ala Thr Ala Met Gly Gln
            660                 665                 670

Ala Phe Asp Thr Ala Lys Ser Gly Asp Ser Phe Tyr Leu Pro Pro Glu
        675                 680                 685

Ala Phe Asp Asn Ala Glu Phe Gln Gln Gly Met Lys Leu Phe Leu Ser
    690                 695                 700

Pro Asn Gly Lys Ala Val Arg Phe Val Ile Ser His Glu Ser Asp Pro
705                 710                 715                 720

Ala Ser Thr Glu Gly Ile Asp Arg Ile Glu Ala Ile Arg Ala Ala Thr
                725                 730                 735

Lys Asp Ala Ile Lys Ala Thr Pro Leu Gln Gly Ala Lys Ile Tyr Ile
            740                 745                 750

Gly Gly Thr Ala Ala Thr Tyr Gln Asp Ile Arg Asp Gly Thr Lys Tyr
        755                 760                 765

Asp Ile Leu Ile Val Gly Ile Ala Ala Val Cys Leu Val Phe Ile Val
    770                 775                 780

Met Leu Met Ile Thr Gln Ser Leu Ile Ala Ser Leu Val Ile Val Gly
785                 790                 795                 800

Thr Val Leu Leu Ser Leu Gly Thr Ala Phe Gly Leu Ser Val Leu Ile
```

```
              805                 810                 815
Trp Gln His Phe Val Gly Leu Gln Val His Trp Thr Ile Val Ala Met
            820                 825                 830

Ser Val Ile Val Leu Leu Ala Val Gly Ser Asp Tyr Asn Leu Leu Leu
            835                 840                 845

Val Ser Arg Phe Lys Glu Glu Val Gly Ala Gly Leu Lys Thr Gly Ile
        850                 855                 860

Ile Arg Ala Met Ala Gly Thr Gly Ala Val Thr Ser Ala Gly Leu
865                 870                 875                 880

Val Phe Ala Phe Thr Met Ala Ser Met Ala Val Ser Glu Leu Arg Val
                885                 890                 895

Ile Gly Gln Val Gly Thr Thr Ile Gly Leu Gly Leu Leu Phe Asp Thr
            900                 905                 910

Leu Val Val Arg Ser Phe Met Thr Pro Ser Ile Ala Ala Leu Leu Gly
            915                 920                 925

Arg Trp Phe Trp Trp Pro Asn Met Ile His Ser Arg Pro Thr Val Pro
        930                 935                 940

Glu Ala His Thr Arg Gln Gly Ala Arg Arg Ile Gln Pro His Leu His
945                 950                 955                 960

Arg

<210> SEQ ID NO 53
<211> LENGTH: 6
<212> TYPE: PRT
<213> ORGANISM: Artificial Sequence
<220> FEATURE:
<223> OTHER INFORMATION: Region of similarity between P51BP3_266 and
      membrane protein

<400> SEQUENCE: 53

Val Leu Leu Ser Leu Gly
1               5

<210> SEQ ID NO 54
<211> LENGTH: 177
<212> TYPE: PRT
<213> ORGANISM: Artificial Sequence
<220> FEATURE:
<223> OTHER INFORMATION: P51BP3_166

<400> SEQUENCE: 54

Ser Ala Ser Thr Thr Glu Pro Asp Phe Gln Lys Asp Ile Leu Ile Ala
1               5                  10                  15

Cys Arg Leu Asn Gln Lys Lys Gly Ala Tyr Asp Ile Phe Leu Asn Ala
            20                  25                  30

Lys Glu Gln Asn Ile Val Phe Asn Ala Glu Thr Tyr Ser Asn Leu Ile
        35                  40                  45

Lys Leu Leu Met Ser Glu Asp Tyr Phe Thr Gln Ala Met Glu Val Lys
    50                  55                  60

Ala Phe Ala Glu Thr His Ile Lys Gly Phe Thr Leu Asn Asp Ala Ala
65                  70                  75                  80

Asn Ser Arg Leu Ile Ile Thr Gln Val Arg Arg Asp Tyr Leu Lys Glu
                85                  90                  95

Ala Val Thr Thr Leu Lys Thr Val Leu Asp Gln Gln Gln Thr Pro Ser
            100                 105                 110

Arg Leu Ala Val Thr Arg Val Ile Gln Ala Leu Ala Met Lys Gly Asp
        115                 120                 125
```

```
Val Glu Asn Ile Glu Val Val Gln Lys Met Leu Asn Gly Leu Glu Asp
    130                 135                 140

Ser Ile Gly Leu Ser Lys Met Val Phe Ile Asn Asn Ile Ala Leu Ala
145                 150                 155                 160

Gln Ile Lys Asn Asn Ile Asp Ala Ala Lys Leu Ala Ala Ala Leu
                165                 170                 175

Glu

<210> SEQ ID NO 55
<211> LENGTH: 1273
<212> TYPE: PRT
<213> ORGANISM: Artificial Sequence
<220> FEATURE:
<223> OTHER INFORMATION: Leucine-rich PPR-motif containing protein

<400> SEQUENCE: 55

Met Pro Cys Phe Tyr Leu Arg Ser Cys Gly Ser Leu Pro Glu Leu
1               5                   10                  15

Lys Leu Glu Glu Arg Thr Glu Phe Ala His Arg Ile Trp Asp Thr Leu
                20                  25                  30

Gln Lys Leu Gly Ala Val Tyr Asp Val Ser His Tyr Asn Ala Leu Leu
            35                  40                  45

Lys Val Tyr Leu Gln Asn Glu Tyr Lys Phe Ser Pro Thr Asp Phe Leu
    50                  55                  60

Ala Lys Met Glu Glu Ala Asn Ile Gln Pro Asn Arg Val Thr Tyr Gln
65                  70                  75                  80

Arg Leu Ile Ala Ser Tyr Cys Asn Val Gly Asp Ile Glu Gly Ala Ser
                85                  90                  95

Lys Ile Leu Gly Phe Met Lys Thr Lys Asp Leu Pro Val Thr Glu Ala
            100                 105                 110

Val Phe Ser Ala Leu Val Thr Gly His Ala Arg Ala Gly Asp Met Glu
    115                 120                 125

Asn Ala Glu Asn Ile Leu Thr Val Met Arg Asp Ala Gly Ile Glu Pro
    130                 135                 140

Gly Pro Asp Thr Tyr Leu Ala Leu Leu Asn Ala Tyr Ala Glu Lys Gly
145                 150                 155                 160

Asp Ile Asp His Val Lys Gln Thr Leu Glu Lys Val Glu Lys Phe Glu
                165                 170                 175

Leu His Leu Met Asp Arg Asp Leu Leu Gln Ile Ile Phe Ser Phe Ser
            180                 185                 190

Lys Ala Gly Tyr Leu Ser Met Ser Gln Lys Phe Trp Lys Lys Phe Thr
        195                 200                 205

Cys Glu Arg Arg Tyr Ile Pro Asp Ala Met Asn Leu Ile Leu Leu Leu
    210                 215                 220

Val Thr Glu Lys Leu Glu Asp Val Ala Leu Gln Ile Leu Leu Ala Cys
225                 230                 235                 240

Pro Val Ser Lys Glu Asp Gly Pro Ser Val Phe Gly Ser Phe Leu
                245                 250                 255

Gln His Cys Val Thr Met Asn Thr Pro Val Glu Lys Leu Thr Asp Tyr
            260                 265                 270

Cys Lys Lys Leu Lys Glu Val Gln Met His Ser Phe Pro Leu Gln Phe
        275                 280                 285

Thr Leu His Cys Ala Leu Leu Ala Asn Lys Thr Asp Leu Ala Lys Ala
    290                 295                 300

Leu Met Lys Ala Val Lys Glu Glu Gly Phe Pro Ile Arg Pro His Tyr
```

-continued

```
              305                 310                 315                 320
         Phe Trp Pro Leu Leu Val Gly Arg Arg Lys Glu Lys Asn Val Gln Gly
                         325                 330                 335

Ile Ile Glu Ile Leu Lys Gly Met Gln Glu Leu Gly Val His Pro Asp
                         340                 345                 350

Gln Glu Thr Tyr Thr Asp Tyr Val Ile Pro Cys Phe Asp Ser Val Asn
                         355                 360                 365

Ser Ala Arg Ala Ile Leu Gln Glu Asn Gly Cys Leu Ser Asp Ser Asp
                 370                 375                 380

Met Phe Ser Gln Ala Gly Leu Arg Ser Glu Ala Ala Asn Gly Asn Leu
         385                 390                 395                 400

Asp Phe Val Leu Ser Phe Leu Lys Ser Asn Thr Leu Pro Ile Ser Leu
                         405                 410                 415

Gln Ser Ile Arg Ser Ser Leu Leu Gly Phe Arg Arg Ser Met Asn
                         420                 425                 430

Ile Asn Val Trp Ser Glu Ile Thr Glu Leu Leu Tyr Lys Asp Gly Arg
                         435                 440                 445

Tyr Cys Gln Glu Pro Arg Gly Pro Thr Glu Ala Val Gly Asn Phe Leu
                 450                 455                 460

Tyr Asn Leu Ile Asp Ser Met Ser Asp Ser Glu Val Gln Ala Lys Glu
         465                 470                 475                 480

Glu His Leu Arg Gln Tyr Phe His Gln Leu Glu Lys Met Asn Val Lys
                         485                 490                 495

Ile Pro Glu Asn Ile Tyr Arg Gly Ile Arg Asn Leu Leu Glu Ser Tyr
                         500                 505                 510

His Val Pro Glu Leu Ile Lys Asp Ala His Leu Leu Val Glu Arg Lys
                 515                 520                 525

Asn Leu Asp Phe Gln Lys Thr Val Gln Leu Thr Ser Ser Glu Leu Glu
                 530                 535                 540

Ser Thr Leu Glu Thr Leu Lys Ala Glu Asn Gln Pro Ile Arg Asp Val
         545                 550                 555                 560

Leu Lys Gln Leu Ile Leu Val Leu Cys Ser Glu Glu Asn Met Gln Lys
                         565                 570                 575

Ala Leu Glu Leu Lys Ala Lys Tyr Glu Ser Asp Met Val Thr Gly Gly
                         580                 585                 590

Tyr Ala Ala Leu Ile Asn Leu Cys Cys Arg His Asp Lys Val Glu Asp
                 595                 600                 605

Ala Leu Asn Leu Lys Glu Glu Phe Asp Arg Leu Asp Ser Ser Ala Val
                 610                 615                 620

Leu Asp Thr Gly Asn Tyr Leu Gly Leu Val Arg Val Leu Ala Lys His
         625                 630                 635                 640

Gly Lys Leu Gln Asp Ala Ile Lys Ile Leu Lys Glu Met Lys Glu Lys
                         645                 650                 655

Asp Val Leu Ile Lys Asp Thr Thr Ala Leu Ser Phe Phe His Met Leu
                         660                 665                 670

Asn Gly Ala Ala Leu Arg Gly Glu Ile Glu Thr Val Lys Gln Leu His
                 675                 680                 685

Glu Ala Ile Val Thr Leu Gly Leu Ala Glu Pro Ser Thr Asn Ile Ser
                 690                 695                 700

Phe Pro Leu Val Thr Val His Leu Glu Lys Gly Asp Leu Ser Thr Ala
         705                 710                 715                 720

Leu Glu Val Ala Ile Asp Cys Tyr Glu Lys Tyr Lys Val Leu Pro Arg
                         725                 730                 735
```

```
Ile His Asp Val Leu Cys Lys Leu Val Glu Lys Gly Glu Thr Asp Leu
            740                 745                 750

Ile Gln Lys Ala Met Asp Phe Val Ser Gln Glu Gln Gly Glu Met Val
            755                 760                 765

Met Leu Tyr Asp Leu Phe Phe Ala Phe Leu Gln Thr Gly Asn Tyr Lys
770                 775                 780

Glu Ala Lys Lys Ile Ile Glu Thr Pro Gly Ile Arg Ala Arg Ser Ala
785                 790                 795                 800

Arg Leu Gln Trp Phe Cys Asp Arg Cys Val Ala Asn Asn Gln Val Glu
                805                 810                 815

Thr Leu Glu Lys Leu Val Glu Leu Thr Gln Lys Leu Phe Glu Cys Asp
            820                 825                 830

Arg Asp Gln Met Tyr Tyr Asn Leu Leu Lys Leu Tyr Lys Ile Asn Gly
            835                 840                 845

Asp Trp Gln Arg Ala Asp Ala Val Trp Asn Lys Ile Gln Glu Glu Asn
850                 855                 860

Val Ile Pro Arg Glu Lys Thr Leu Arg Leu Leu Ala Glu Ile Leu Arg
865                 870                 875                 880

Glu Gly Asn Gln Glu Val Pro Phe Asp Val Pro Glu Leu Trp Tyr Glu
                885                 890                 895

Asp Glu Lys His Ser Leu Asn Ser Ser Ser Ala Ser Thr Thr Glu Pro
            900                 905                 910

Asp Phe Gln Lys Asp Ile Leu Ile Ala Cys Arg Leu Asn Gln Lys Lys
            915                 920                 925

Gly Ala Tyr Asp Ile Phe Leu Asn Ala Lys Glu Gln Asn Ile Val Phe
930                 935                 940

Asn Ala Glu Thr Tyr Ser Asn Leu Ile Lys Leu Leu Met Ser Glu Asp
945                 950                 955                 960

Tyr Phe Thr Gln Ala Met Glu Val Lys Ala Phe Ala Glu Thr His Ile
                965                 970                 975

Lys Gly Phe Thr Leu Asn Asp Ala Ala Asn Ser Arg Leu Ile Ile Thr
            980                 985                 990

Gln Val Arg Arg Asp Tyr Leu Lys Glu Ala Val Thr Thr Leu Lys Thr
            995                 1000                1005

Val Leu Asp Gln Gln Gln Thr Pro Ser Arg Leu Ala Val Thr Arg
    1010                1015                1020

Val Ile Gln Ala Leu Ala Met Lys Gly Asp Val Glu Asn Ile Glu
    1025                1030                1035

Val Val Gln Lys Met Leu Asn Gly Leu Glu Asp Ser Ile Gly Leu
    1040                1045                1050

Ser Lys Met Val Phe Ile Asn Ile Ala Leu Ala Gln Ile Lys
    1055                1060                1065

Asn Asn Asn Ile Asp Ala Ala Ile Glu Asn Ile Glu Asn Met Leu
    1070                1075                1080

Thr Ser Glu Asn Lys Val Ile Glu Pro Gln Tyr Phe Gly Leu Ala
    1085                1090                1095

Tyr Leu Phe Arg Lys Val Ile Glu Glu Gln Leu Glu Pro Ala Val
    1100                1105                1110

Glu Lys Ile Ser Ile Met Ala Glu Arg Leu Ala Asn Gln Phe Ala
    1115                1120                1125

Ile Tyr Lys Pro Val Thr Asp Phe Phe Leu Gln Leu Val Asp Ala
    1130                1135                1140
```

```
Gly Lys Val Asp Asp Ala Arg Ala Leu Leu Gln Arg Cys Gly Ala
    1145                1150                1155

Ile Ala Glu Gln Thr Pro Ile Leu Leu Leu Phe Leu Leu Arg Asn
    1160                1165                1170

Ser Arg Lys Gln Gly Lys Ala Ser Thr Val Lys Ser Val Leu Glu
    1175                1180                1185

Leu Ile Pro Glu Leu Asn Glu Lys Glu Ala Tyr Asn Ser Leu
    1190                1195                1200

Met Lys Ser Tyr Val Ser Glu Lys Asp Val Thr Ser Ala Lys Ala
    1205                1210                1215

Leu Tyr Glu His Leu Thr Ala Lys Asn Thr Lys Leu Asp Asp Leu
    1220                1225                1230

Phe Leu Lys Arg Tyr Ala Ser Leu Leu Lys Tyr Ala Gly Glu Pro
    1235                1240                1245

Val Pro Phe Ile Glu Pro Pro Glu Ser Phe Glu Phe Tyr Ala Gln
    1250                1255                1260

Gln Leu Arg Lys Leu Arg Glu Asn Ser Ser
    1265                1270

<210> SEQ ID NO 56
<211> LENGTH: 170
<212> TYPE: PRT
<213> ORGANISM: Artificial Sequence
<220> FEATURE:
<223> OTHER INFORMATION: Region of similarity between P51BP3_166 and
      Leucine-rich PPR-motif containing protein

<400> SEQUENCE: 56

Ser Ala Ser Thr Thr Glu Pro Asp Phe Gln Lys Asp Ile Leu Ile Ala
1                   5                   10                  15

Cys Arg Leu Asn Gln Lys Lys Gly Ala Tyr Asp Ile Phe Leu Asn Ala
            20                  25                  30

Lys Glu Gln Asn Ile Val Phe Asn Ala Glu Thr Tyr Ser Asn Leu Ile
        35                  40                  45

Lys Leu Leu Met Ser Glu Asp Tyr Phe Thr Gln Ala Met Glu Val Lys
    50                  55                  60

Ala Phe Ala Glu Thr His Ile Lys Gly Phe Thr Leu Asn Asp Ala Ala
65                  70                  75                  80

Asn Ser Arg Leu Ile Ile Thr Gln Val Arg Arg Asp Tyr Leu Lys Glu
                85                  90                  95

Ala Val Thr Thr Leu Lys Thr Val Leu Asp Gln Gln Gln Thr Pro Ser
            100                 105                 110

Arg Leu Ala Val Thr Arg Val Ile Gln Ala Leu Ala Met Lys Gly Asp
        115                 120                 125

Val Glu Asn Ile Glu Val Val Gln Lys Met Leu Asn Gly Leu Glu Asp
    130                 135                 140

Ser Ile Gly Leu Ser Lys Met Val Phe Ile Asn Asn Ile Ala Leu Ala
145                 150                 155                 160

Gln Ile Lys Asn Asn Asn Ile Asp Ala Ala
                165                 170

<210> SEQ ID NO 57
<211> LENGTH: 49
<212> TYPE: PRT
<213> ORGANISM: Artificial Sequence
<220> FEATURE:
<223> OTHER INFORMATION: P51BP4_704
```

```
<400> SEQUENCE: 57

Asp Ala Ser Pro Leu Pro Glu Thr Thr Glu Asn Val Val Cys Ala
1               5                   10                  15

Leu Gly Leu Thr Val Gly Leu Val Gly Ile Ile Ile Gly Thr Ile Phe
            20                  25                  30

Ile Ile Lys Gly Val Arg Lys Ser Asn Ala Ala Glu Arg Arg Gly Pro
        35                  40                  45

Leu

<210> SEQ ID NO 58
<211> LENGTH: 50
<212> TYPE: PRT
<213> ORGANISM: Homo sapiens

<400> SEQUENCE: 58

Phe Asp Ala Pro Ser Pro Leu Pro Glu Thr Thr Glu Asn Val Val Cys
1               5                   10                  15

Ala Leu Gly Leu Thr Val Gly Leu Val Gly Ile Ile Ile Gly Thr Ile
            20                  25                  30

Phe Ile Ile Lys Gly Leu Arg Lys Ser Asn Ala Ala Glu Arg Arg Gly
        35                  40                  45

Pro Leu
    50

<210> SEQ ID NO 59
<211> LENGTH: 49
<212> TYPE: PRT
<213> ORGANISM: Artificial Sequence
<220> FEATURE:
<223> OTHER INFORMATION: Region of similarity between P51BP4_704 and
      HLA-DR alpha
<220> FEATURE:
<221> NAME/KEY: Xaa
<222> LOCATION: (37)..(37)
<223> OTHER INFORMATION: Xaa denotes a region of non-similarity

<400> SEQUENCE: 59

Asp Ala Ser Pro Leu Pro Glu Thr Thr Glu Asn Val Val Cys Ala
1               5                   10                  15

Leu Gly Leu Thr Val Gly Leu Val Gly Ile Ile Ile Gly Thr Ile Phe
            20                  25                  30

Ile Ile Lys Gly Xaa Arg Lys Ser Asn Ala Ala Glu Arg Arg Gly Pro
        35                  40                  45

Leu

<210> SEQ ID NO 60
<211> LENGTH: 17
<212> TYPE: PRT
<213> ORGANISM: Artificial Sequence
<220> FEATURE:
<223> OTHER INFORMATION: P197BP4_763

<400> SEQUENCE: 60

Asp Leu Ser Ser Glu Val Ala Thr His Gln Pro Ile Ile Ala Cys Leu
1               5                   10                  15

Pro

<210> SEQ ID NO 61
<211> LENGTH: 651
<212> TYPE: PRT
<213> ORGANISM: Mycobacterium tuberculosis]
```

<400> SEQUENCE: 61

```
Met Ser Leu Ala Pro Leu Ala Tyr Thr Leu Phe Gln Arg Thr Met Arg
1               5                   10                  15

His Asp Pro Ser Asp Thr His Trp Leu Gly Arg Asp Arg Phe Val Leu
            20                  25                  30

Ser Ala Gly His Ser Ser Leu Thr Leu Tyr Ile Gln Leu Tyr Leu Gly
        35                  40                  45

Gly Phe Gly Leu Glu Leu Ser Asp Ile Glu Ser Leu Arg Thr Trp Gly
    50                  55                  60

Ser Lys Thr Pro Gly His Pro Glu Phe Arg His Thr Pro Gly Val Glu
65                  70                  75                  80

Ile Thr Thr Gly Pro Leu Gly Gln Gly Leu Ala Ser Ala Val Gly Met
                85                  90                  95

Ala Met Ala Ser Arg Tyr Glu Arg Gly Leu Phe Asp Pro Asp Ala Glu
            100                 105                 110

Pro Gly Ala Ser Pro Phe Asp His Tyr Ile Tyr Val Ile Ala Ser Asp
        115                 120                 125

Gly Asp Ile Glu Glu Gly Val Thr Ser Glu Ala Ser Ser Leu Ala Ala
    130                 135                 140

Val Gln Gln Leu Gly Asn Leu Ile Val Phe Tyr Asp Arg Asn Gln Ile
145                 150                 155                 160

Ser Ile Glu Asp Asp Thr Asn Ile Ala Leu Cys Glu Asp Thr Ala Ala
                165                 170                 175

Arg Tyr Arg Ala Tyr Gly Trp His Val Gln Glu Val Glu Gly Gly Glu
            180                 185                 190

Asn Val Val Gly Ile Glu Glu Ala Ile Ala Asn Ala Gln Ala Val Thr
        195                 200                 205

Asp Arg Pro Ser Phe Ile Ala Leu Arg Thr Val Ile Gly Tyr Pro Ala
    210                 215                 220

Pro Asn Leu Met Asp Thr Gly Lys Ala His Gly Ala Ala Leu Gly Asp
225                 230                 235                 240

Asp Glu Val Ala Ala Val Lys Lys Ile Val Gly Phe Asp Pro Asp Lys
                245                 250                 255

Thr Phe Gln Val Arg Glu Asp Val Leu Thr His Thr Arg Gly Leu Val
            260                 265                 270

Ala Arg Gly Lys Gln Ala His Glu Arg Trp Gln Leu Glu Phe Asp Ala
        275                 280                 285

Trp Ala Arg Arg Glu Pro Glu Arg Lys Ala Leu Leu Asp Arg Leu Leu
    290                 295                 300

Ala Gln Lys Leu Pro Asp Gly Trp Asp Ala Asp Leu Pro His Trp Glu
305                 310                 315                 320

Pro Gly Ser Lys Ala Leu Ala Thr Arg Ala Ala Ser Gly Ala Val Leu
                325                 330                 335

Ser Ala Leu Gly Pro Lys Leu Pro Glu Leu Trp Gly Gly Ser Ala Asp
            340                 345                 350

Leu Ala Gly Ser Asn Asn Thr Thr Ile Lys Gly Ala Asp Ser Phe Gly
        355                 360                 365

Pro Pro Ser Ile Ser Thr Lys Glu Tyr Thr Ala His Trp Tyr Gly Arg
    370                 375                 380

Thr Leu His Phe Gly Val Arg Glu His Ala Met Gly Ala Ile Leu Ser
385                 390                 395                 400

Gly Ile Val Leu His Gly Pro Thr Arg Ala Tyr Gly Gly Thr Phe Leu
```

```
                405                 410                 415
Gln Phe Ser Asp Tyr Met Arg Pro Ala Val Arg Leu Ala Ala Leu Met
            420                 425                 430

Asp Ile Asp Thr Ile Tyr Val Trp Thr His Asp Ser Ile Gly Leu Gly
        435                 440                 445

Glu Asp Gly Pro Thr His Gln Pro Ile Glu His Leu Ser Ala Leu Arg
    450                 455                 460

Ala Ile Pro Arg Leu Ser Val Val Arg Pro Ala Asp Ala Asn Glu Thr
465                 470                 475                 480

Ala Tyr Ala Trp Arg Thr Ile Leu Ala Arg Arg Asn Gly Ser Gly Pro
                485                 490                 495

Val Gly Leu Ile Leu Thr Arg Gln Gly Val Pro Val Leu Asp Gly Thr
            500                 505                 510

Asp Ala Glu Gly Val Ala Arg Gly Gly Tyr Val Leu Ser Asp Ala Gly
        515                 520                 525

Gly Leu Gln Pro Gly Glu Glu Pro Asp Val Ile Leu Ile Ala Thr Gly
    530                 535                 540

Ser Glu Val Gln Leu Ala Val Ala Ala Gln Thr Leu Leu Ala Asp Asn
545                 550                 555                 560

Asp Ile Leu Ala Arg Val Val Ser Met Pro Cys Leu Glu Trp Phe Glu
                565                 570                 575

Ala Gln Pro Tyr Glu Tyr Arg Asp Ala Val Leu Pro Pro Thr Val Ser
            580                 585                 590

Ala Arg Val Ala Val Glu Ala Gly Val Ala Gln Cys Trp His Gln Leu
        595                 600                 605

Val Gly Asp Thr Gly Glu Ile Val Ser Ile Glu His Tyr Gly Glu Ser
    610                 615                 620

Ala Asp His Lys Thr Leu Phe Arg Glu Tyr Gly Phe Thr Ala Glu Ala
625                 630                 635                 640

Val Ala Ala Ala Glu Arg Ala Leu Asp Asn
                645                 650

<210> SEQ ID NO 62
<211> LENGTH: 5
<212> TYPE: PRT
<213> ORGANISM: Artificial Sequence
<220> FEATURE:
<223> OTHER INFORMATION: Region of similarity between P197BP4_763 and
      transketolase

<400> SEQUENCE: 62

Thr His Gln Pro Ile
1               5

<210> SEQ ID NO 63
<211> LENGTH: 13
<212> TYPE: PRT
<213> ORGANISM: Artificial Sequence
<220> FEATURE:
<223> OTHER INFORMATION: P51BP4_563

<400> SEQUENCE: 63

Leu Gln Ala Cys Phe Pro Gln Ile Leu Arg Gly Ser Leu
1               5                   10

<210> SEQ ID NO 64
<211> LENGTH: 575
<212> TYPE: PRT
<213> ORGANISM: Mycobacterium tuberculosis
```

<400> SEQUENCE: 64

```
Met Pro Gln Thr Thr Asp Glu Ala Ala Ser Val Ser Thr Val Ala Asp
1               5                   10                  15

Ile Lys Pro Arg Ser Arg Asp Val Thr Asp Gly Leu Glu Lys Ala Ala
            20                  25                  30

Ala Arg Gly Met Leu Arg Ala Val Gly Met Asp Asp Glu Asp Phe Ala
        35                  40                  45

Lys Pro Gln Ile Gly Val Ala Ser Ser Trp Asn Glu Ile Thr Pro Cys
    50                  55                  60

Asn Leu Ser Leu Asp Arg Leu Ala Asn Ala Val Lys Glu Gly Val Phe
65                  70                  75                  80

Ser Ala Gly Gly Tyr Pro Leu Glu Phe Gly Thr Ile Ser Val Ser Asp
                85                  90                  95

Gly Ile Ser Met Gly His Glu Gly Met His Phe Ser Leu Val Ser Arg
            100                 105                 110

Glu Val Ile Ala Asp Ser Val Glu Val Val Met Gln Ala Glu Arg Leu
        115                 120                 125

Asp Gly Ser Val Leu Leu Ala Gly Cys Asp Lys Ser Leu Pro Gly Met
130                 135                 140

Leu Met Ala Ala Ala Arg Leu Asp Leu Ala Ala Val Phe Leu Tyr Ala
145                 150                 155                 160

Gly Ser Ile Leu Pro Gly Arg Ala Lys Leu Ser Asp Gly Ser Glu Arg
                165                 170                 175

Asp Val Thr Ile Ile Asp Ala Phe Glu Ala Val Gly Ala Cys Ser Arg
            180                 185                 190

Gly Leu Met Ser Arg Ala Asp Val Asp Ala Ile Glu Arg Ala Ile Cys
        195                 200                 205

Pro Gly Glu Gly Ala Cys Gly Gly Met Tyr Thr Ala Asn Thr Met Ala
210                 215                 220

Ser Ala Ala Glu Ala Leu Gly Met Ser Leu Pro Gly Ser Ala Ala Pro
225                 230                 235                 240

Pro Ala Thr Asp Arg Arg Arg Asp Gly Phe Ala Arg Arg Ser Gly Gln
                245                 250                 255

Ala Val Val Glu Leu Leu Arg Arg Gly Ile Thr Ala Arg Asp Ile Leu
            260                 265                 270

Thr Lys Glu Ala Phe Glu Asn Ala Ile Ala Val Val Met Ala Phe Gly
        275                 280                 285

Gly Ser Thr Asn Ala Val Leu His Leu Leu Ala Ile Ala His Glu Ala
290                 295                 300

Asn Val Ala Leu Ser Leu Gln Asp Phe Ser Arg Ile Gly Ser Gly Val
305                 310                 315                 320

Pro His Leu Ala Asp Val Lys Pro Phe Gly Arg His Val Met Ser Asp
                325                 330                 335

Val Asp His Ile Gly Gly Val Pro Val Val Met Lys Ala Leu Leu Asp
            340                 345                 350

Ala Gly Leu Leu His Gly Asp Cys Leu Thr Val Thr Gly His Thr Met
        355                 360                 365

Ala Glu Asn Leu Ala Ala Ile Thr Pro Pro Asp Pro Asp Gly Lys Val
370                 375                 380

Leu Arg Ala Leu Ala Asn Pro Ile His Pro Ser Gly Gly Ile Thr Ile
385                 390                 395                 400

Leu His Gly Ser Leu Ala Pro Glu Gly Ala Val Val Lys Thr Ala Gly
```

```
                405                 410                 415
Phe Asp Ser Asp Val Phe Glu Gly Thr Ala Arg Val Phe Asp Gly Glu
            420                 425                 430

Arg Ala Ala Leu Asp Ala Leu Glu Asp Gly Thr Ile Thr Val Gly Asp
        435                 440                 445

Ala Val Val Ile Arg Tyr Glu Gly Pro Lys Gly Pro Gly Met Arg
    450                 455                 460

Glu Met Leu Ala Ile Thr Gly Ala Ile Lys Gly Ala Gly Leu Gly Lys
465                 470                 475                 480

Asp Ile Leu Leu Leu Thr Asp Gly Arg Phe Ser Gly Gly Thr Thr Gly
                485                 490                 495

Leu Cys Val Gly His Ile Ala Pro Glu Ala Val Asp Gly Gly Pro Ile
            500                 505                 510

Ala Leu Leu Arg Asn Gly Asp Arg Ile Arg Leu Asp Val Ala Gly Arg
        515                 520                 525

Val Leu Asp Val Leu Ala Asp Pro Ala Glu Phe Ala Ser Arg Gln Gln
    530                 535                 540

Asp Phe Ser Pro Pro Pro Arg Tyr Thr Thr Gly Val Leu Ser Lys
545                 550                 555                 560

Tyr Val Lys Leu Val Ser Ser Ala Ala Val Gly Ala Val Cys Gly
                565                 570                 575

<210> SEQ ID NO 65
<211> LENGTH: 7
<212> TYPE: PRT
<213> ORGANISM: Artificial Sequence
<220> FEATURE:
<223> OTHER INFORMATION: Region of similarity between P51BP4_563
      dihydroxy-acid dehydratase
<220> FEATURE:
<221> NAME/KEY: Xaa
<222> LOCATION: (3)..(3)
<223> OTHER INFORMATION: Xaa denotes a region of non-similarity

<400> SEQUENCE: 65

Ile Leu Xaa Gly Ser Leu Ala
1               5

<210> SEQ ID NO 66
<211> LENGTH: 16
<212> TYPE: PRT
<213> ORGANISM: Artificial Sequence
<220> FEATURE:
<223> OTHER INFORMATION: P51BP3_113

<400> SEQUENCE: 66

Ala Gly Ile Ser Arg Glu Leu Val Asp Lys Leu Ala Ala Ala Leu Glu
1               5                   10                  15

<210> SEQ ID NO 67
<211> LENGTH: 174
<212> TYPE: PRT
<213> ORGANISM: Artificial Sequence
<220> FEATURE:
<223> OTHER INFORMATION: Chain A, Mycobacterium Tuberculosis
      Bacterioferritin, Bfra

<400> SEQUENCE: 67

Met Gly Met Gln Gly Asp Pro Asp Val Leu Arg Leu Leu Asn Glu Gln
1               5                   10                  15

Leu Thr Ser Glu Leu Thr Ala Ile Asn Gln Tyr Phe Leu His Ser Lys
            20                  25                  30
```

```
Met Gln Asp Asn Trp Gly Phe Thr Glu Leu Ala Ala His Thr Arg Ala
            35                  40                  45

Glu Ser Phe Asp Glu Met Arg His Ala Glu Glu Ile Thr Asp Arg Ile
 50                  55                  60

Leu Leu Leu Asp Gly Leu Pro Asn Tyr Gln Arg Ile Gly Ser Leu Arg
 65                  70                  75                  80

Ile Gly Gln Thr Leu Arg Glu Gln Phe Glu Ala Asp Leu Ala Ile Glu
                 85                  90                  95

Tyr Asp Val Leu Asn Arg Leu Lys Pro Gly Ile Val Met Cys Arg Glu
                100                 105                 110

Lys Gln Asp Thr Thr Ser Ala Val Leu Leu Glu Lys Ile Val Ala Asp
                115                 120                 125

Glu Glu His Ile Asp Tyr Leu Glu Thr Gln Leu Glu Leu Met Asp
            130                 135                 140

Lys Leu Gly Glu Glu Leu Tyr Ser Ala Gln Cys Val Ser Arg Pro Pro
145                 150                 155                 160

Thr Lys Leu Ala Ala Ala Leu Glu His His His His His His
                165                 170
```

```
<210> SEQ ID NO 68
<211> LENGTH: 7
<212> TYPE: PRT
<213> ORGANISM: Artificial Sequence
<220> FEATURE:
<223> OTHER INFORMATION: Region of similarity between P51BP3_113 and
      Chain A, Mycobacterium Tuberculosis Bacterioferritin, Bfra

<400> SEQUENCE: 68

Lys Leu Ala Ala Ala Leu Glu
 1               5

<210> SEQ ID NO 69
<211> LENGTH: 209
<212> TYPE: PRT
<213> ORGANISM: Artificial Sequence
<220> FEATURE:
<223> OTHER INFORMATION: P51BP3_200
<220> FEATURE:
<221> NAME/KEY: misc_feature
<222> LOCATION: (190)..(190)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid

<400> SEQUENCE: 69

Ser Ser Ser Thr Pro Leu Ser Asn Gly Pro Leu Asn Gly Asp Val Asp
 1               5                  10                  15

Tyr Phe Gly Gln Gln Phe Asp Gln Ile Ser Asn Arg Thr Gly Lys Gln
                20                  25                  30

Glu Ala Gln Ala Gly Pro Trp Pro Phe Ser Ser Ser Gln Thr Gln Pro
            35                  40                  45

Ala Val Arg Thr Gln Asn Gly Val Ser Glu Arg Glu Gln Asn Gly Phe
 50                  55                  60

Ser Val Lys Ser Ser Pro Asn Pro Phe Val Gly Ser Pro Pro Lys Gly
 65                  70                  75                  80

Leu Ser Ile Gln Asn Gly Val Lys Gln Asp Leu Glu Ser Ser Val Gln
                 85                  90                  95

Ser Ser Pro His Asp Ser Ile Ala Ile Pro Pro Pro Gln Ser Thr
```

```
                    100                 105                 110
Lys Pro Gly Arg Gly Arg Thr Ala Lys Ser Ser Ala Asn Asp Leu
            115                 120                 125

Leu Ala Ser Asp Ile Phe Ala Pro Val Ser Glu Pro Ser Gly Gln
130                 135                 140

Ala Ser Pro Thr Gly Gln Pro Thr Ala Leu Gln Pro Asn Pro Leu Asp
145                 150                 155                 160

Leu Phe Lys Thr Ser Ala Pro Ala Pro Val Gly Pro Leu Val Gly Leu
                165                 170                 175

Gly Gly Val Thr Val Thr Leu Pro Gln Ala Gly Pro Trp Xaa Thr Ala
                180                 185                 190

Ser Leu Val Phe Asn Gln Ser Pro Ser Trp Xaa Leu Ala Ala Ala Leu
                195                 200                 205

Glu

<210> SEQ ID NO 70
<211> LENGTH: 749
<212> TYPE: PRT
<213> ORGANISM: Homo sapiens

<400> SEQUENCE: 70

Met Ser Asn Glu Val Glu Thr Ser Ala Thr Asn Gly Gln Pro Asp Gln
1               5                   10                  15

Gln Ala Ala Pro Lys Ala Pro Ser Lys Lys Glu Lys Lys Lys Gly Pro
                20                  25                  30

Glu Lys Thr Asp Glu Tyr Leu Leu Ala Arg Phe Lys Gly Asp Gly Val
            35                  40                  45

Lys Tyr Lys Ala Lys Leu Ile Gly Ile Asp Asp Val Pro Asp Ala Arg
50                  55                  60

Gly Asp Lys Met Ser Gln Asp Ser Met Met Lys Leu Lys Gly Met Ala
65                  70                  75                  80

Ala Ala Gly Arg Ser Gln Gly Gln His Lys Gln Arg Ile Trp Val Asn
                85                  90                  95

Ile Ser Leu Ser Gly Ile Lys Ile Ile Asp Glu Lys Thr Gly Val Ile
                100                 105                 110

Glu His Glu His Pro Val Asn Lys Ile Ser Phe Ile Ala Arg Asp Val
            115                 120                 125

Thr Asp Asn Arg Ala Phe Gly Tyr Val Cys Gly Gly Glu Gly Gln His
130                 135                 140

Gln Phe Phe Ala Ile Lys Thr Gly Gln Gln Ala Glu Pro Leu Val Val
145                 150                 155                 160

Asp Leu Lys Asp Leu Phe Gln Val Ile Tyr Asn Val Lys Lys Lys Glu
                165                 170                 175

Glu Glu Lys Lys Lys Ile Glu Glu Ala Ser Lys Ala Val Glu Asn Gly
                180                 185                 190

Ser Glu Ala Leu Met Ile Leu Asp Asp Gln Thr Asn Lys Leu Lys Ser
                195                 200                 205

Glu Ser Lys Asp Ile Leu Leu Val Asp Leu Asn Ser Glu Ile Asp Thr
            210                 215                 220

Asn Gln Asn Ser Leu Arg Glu Asn Pro Phe Leu Thr Asn Gly Ile Thr
225                 230                 235                 240

Ser Cys Ser Leu Pro Arg Pro Thr Pro Gln Ala Ser Phe Leu Pro Glu
                245                 250                 255

Asn Ala Phe Ser Ala Asn Leu Asn Phe Phe Pro Thr Pro Asn Pro Asp
```

-continued

```
                260                 265                 270
Pro Phe Arg Asp Asp Pro Phe Thr Gln Pro Asp Gln Ser Thr Pro Ser
            275                 280                 285
Ser Phe Asp Ser Leu Lys Ser Pro Asp Gln Lys Glu Asn Ser Ser
            290                 295                 300
Ser Ser Ser Thr Pro Leu Ser Asn Gly Pro Leu Asn Gly Asp Val Asp
305                 310                 315                 320
Tyr Phe Gly Gln Gln Phe Asp Gln Ile Ser Asn Arg Thr Gly Lys Gln
                325                 330                 335
Glu Ala Gln Ala Gly Pro Trp Pro Phe Ser Ser Gln Thr Gln Pro
            340                 345                 350
Ala Val Arg Thr Gln Asn Gly Val Ser Glu Arg Glu Gln Asn Gly Phe
            355                 360                 365
Ser Val Lys Ser Ser Pro Asn Pro Phe Val Gly Ser Pro Pro Lys Gly
            370                 375                 380
Leu Ser Ile Gln Asn Gly Val Lys Gln Asp Leu Glu Ser Ser Val Gln
385                 390                 395                 400
Ser Ser Pro His Asp Ser Ile Ala Ile Ile Pro Pro Gln Ser Thr
                405                 410                 415
Lys Pro Gly Arg Gly Arg Arg Thr Ala Lys Ser Ser Ala Asn Asp Leu
            420                 425                 430
Leu Ala Ser Asp Ile Phe Ala Pro Pro Val Ser Glu Pro Ser Gly Gln
            435                 440                 445
Ala Ser Pro Thr Gly Gln Pro Thr Ala Leu Gln Pro Asn Pro Leu Asp
            450                 455                 460
Leu Phe Lys Thr Ser Ala Pro Ala Pro Val Gly Pro Leu Val Gly Leu
465                 470                 475                 480
Gly Gly Val Thr Val Thr Leu Pro Gln Ala Gly Pro Trp Asn Thr Ala
                485                 490                 495
Ser Leu Val Phe Asn Gln Ser Pro Ser Met Ala Pro Gly Ala Met Met
                500                 505                 510
Gly Gly Gln Pro Ser Gly Phe Ser Gln Pro Val Ile Phe Gly Thr Ser
            515                 520                 525
Pro Ala Val Ser Gly Trp Asn Gln Pro Ser Pro Phe Ala Ala Ser Thr
            530                 535                 540
Pro Pro Pro Val Pro Val Val Trp Gly Pro Ser Ala Ser Val Ala Pro
545                 550                 555                 560
Asn Ala Trp Ser Thr Thr Ser Pro Leu Gly Asn Pro Phe Gln Ser Asn
                565                 570                 575
Ile Phe Pro Ala Pro Ala Val Ser Thr Gln Pro Pro Ser Met His Ser
            580                 585                 590
Ser Leu Leu Val Thr Pro Pro Gln Pro Pro Arg Ala Gly Pro Pro
            595                 600                 605
Lys Asp Ile Ser Ser Asp Ala Phe Thr Ala Leu Asp Pro Leu Gly Asp
            610                 615                 620
Lys Glu Ile Lys Asp Val Lys Glu Met Phe Lys Asp Phe Gln Leu Arg
625                 630                 635                 640
Gln Pro Pro Ala Val Pro Ala Arg Lys Gly Glu Gln Thr Ser Ser Gly
                645                 650                 655
Thr Leu Ser Ala Phe Ala Ser Tyr Phe Asn Ser Lys Val Gly Ile Pro
                660                 665                 670
Gln Glu Asn Ala Asp His Asp Asp Phe Asp Ala Asn Gln Leu Leu Asn
            675                 680                 685
```

```
Lys Ile Asn Glu Pro Pro Lys Pro Ala Pro Arg Gln Val Ser Leu Pro
        690                 695                 700

Val Thr Lys Ser Thr Asp Asn Ala Phe Glu Asn Pro Phe Phe Lys Asp
705                 710                 715                 720

Ser Phe Gly Ser Ser Gln Ala Ser Val Ala Ser Ser Gln Pro Val Ser
                725                 730                 735

Ser Glu Met Tyr Arg Asp Pro Phe Gly Asn Pro Phe Ala
            740                 745

<210> SEQ ID NO 71
<211> LENGTH: 201
<212> TYPE: PRT
<213> ORGANISM: Artificial Sequence
<220> FEATURE:
<223> OTHER INFORMATION: Region of similarity between P51BP3_200 and
      Disabled homolog 2 isoform 2
<220> FEATURE:
<221> NAME/KEY: misc_feature
<222> LOCATION: (190)..(190)
<223> OTHER INFORMATION: Xaa can be any naturally occurring amino acid

<400> SEQUENCE: 71

Ser Ser Ser Thr Pro Leu Ser Asn Gly Pro Leu Asn Gly Asp Val Asp
1               5                   10                  15

Tyr Phe Gly Gln Gln Phe Asp Gln Ile Ser Asn Arg Thr Gly Lys Gln
            20                  25                  30

Glu Ala Gln Ala Gly Pro Trp Pro Phe Ser Ser Ser Gln Thr Gln Pro
        35                  40                  45

Ala Val Arg Thr Gln Asn Gly Val Ser Glu Arg Glu Gln Asn Gly Phe
50                  55                  60

Ser Val Lys Ser Ser Pro Asn Pro Phe Val Gly Ser Pro Pro Lys Gly
65                  70                  75                  80

Leu Ser Ile Gln Asn Gly Val Lys Gln Asp Leu Glu Ser Ser Val Gln
                85                  90                  95

Ser Ser Pro His Asp Ser Ile Ala Ile Ile Pro Pro Gln Ser Thr
            100                 105                 110

Lys Pro Gly Arg Gly Arg Arg Thr Ala Lys Ser Ser Ala Asn Asp Leu
            115                 120                 125

Leu Ala Ser Asp Ile Phe Ala Pro Pro Val Ser Glu Pro Ser Gly Gln
130                 135                 140

Ala Ser Pro Thr Gly Gln Pro Thr Ala Leu Gln Pro Asn Pro Leu Asp
145                 150                 155                 160

Leu Phe Lys Thr Ser Ala Pro Ala Pro Val Gly Pro Leu Val Gly Leu
                165                 170                 175

Gly Gly Val Thr Val Thr Leu Pro Gln Ala Gly Pro Trp Xaa Thr Ala
            180                 185                 190

Ser Leu Val Phe Asn Gln Ser Pro Ser
            195                 200

<210> SEQ ID NO 72
<211> LENGTH: 122
<212> TYPE: PRT
<213> ORGANISM: Artificial Sequence
<220> FEATURE:
<223> OTHER INFORMATION: P51BP4_622

<400> SEQUENCE: 72

Ala Ala Ala Ala Met Asp Val Phe Leu Met Ile Arg Arg His Lys Thr
1               5                   10                  15
```

-continued

Thr Ile Phe Thr Asp Ala Lys Glu Ser Ser Thr Val Phe Glu Leu Lys
                20                  25                  30

Arg Ile Val Glu Gly Ile Leu Lys Arg Pro Pro Asp Glu Gln Arg Leu
             35                  40                  45

Tyr Lys Asp Asp Gln Leu Leu Asp Asp Gly Lys Thr Leu Gly Glu Cys
 50                  55                  60

Gly Phe Thr Ser Gln Thr Ala Arg Pro Gln Ala Pro Ala Thr Val Gly
 65                  70                  75                  80

Leu Ala Phe Arg Ala Asp Asp Thr Phe Glu Ala Leu Cys Ile Glu Pro
                 85                  90                  95

Phe Ser Ser Pro Pro Glu Leu Pro Asp Val Met Lys Pro Gln Asp Ser
                100                 105                 110

Gly Ser Ser Ala Asn Glu Gln Ala Val Gln
            115                 120

<210> SEQ ID NO 73
<211> LENGTH: 118
<212> TYPE: PRT
<213> ORGANISM: Homo sapiens

<400> SEQUENCE: 73

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
             35                  40                  45

Gln Leu Leu Asp Asp Gly Lys Thr Leu Gly Glu Cys Gly Phe Thr Ser
 50                  55                  60

Gln Thr Ala Arg Pro Gln Ala Pro Ala Thr Val Gly Leu Ala Phe Arg
 65                  70                  75                  80

Ala Asp Asp Thr Phe Glu Ala Leu Cys Ile Glu Pro Phe Ser Ser Pro
                 85                  90                  95

Pro Glu Leu Pro Asp Val Met Lys Pro Gln Asp Ser Gly Ser Ser Ala
                100                 105                 110

Asn Glu Gln Ala Val Gln
            115

<210> SEQ ID NO 74
<211> LENGTH: 60
<212> TYPE: PRT
<213> ORGANISM: Artificial Sequence
<220> FEATURE:
<223> OTHER INFORMATION: Region of similarity between P51BP4_622 and
      transcription elongation factor B polypeptide 2 isoform a

<400> SEQUENCE: 74

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
             35                  40                  45

Gln Leu Leu Asp Asp Gly Lys Thr Leu Gly Glu Cys
 50                  55                  60

<210> SEQ ID NO 75

```
<211> LENGTH: 21
<212> TYPE: DNA
<213> ORGANISM: Artificial Sequence
<220> FEATURE:
<223> OTHER INFORMATION: T7 phage forward primer

<400> SEQUENCE: 75
gttctatccg caacgttatg g                                              21

<210> SEQ ID NO 76
<211> LENGTH: 22
<212> TYPE: DNA
<213> ORGANISM: Artificial Sequence
<220> FEATURE:
<223> OTHER INFORMATION: T7 phage Reverse primer

<400> SEQUENCE: 76
ggaggaaagt cgtttttgg gg                                              22

<210> SEQ ID NO 77
<211> LENGTH: 21
<212> TYPE: DNA
<213> ORGANISM: Artificial Sequence
<220> FEATURE:
<223> OTHER INFORMATION: T7 phage sequence primer

<400> SEQUENCE: 77
tgctaaggac aacgttatcg g                                              21
```